United States Patent
DeMong et al.

(10) Patent No.: US 9,718,818 B2
(45) Date of Patent: Aug. 1, 2017

(54) COMPOUNDS INHIBITING LEUCINE-RICH REPEAT KINASE ENZYME ACTIVITY

(71) Applicants: MERCK SHARP & DOHME CORP., Rahway, NJ (US); Duane DeMong, Kenilworth, NJ (US); Thomas J. Greshock, West Point, PA (US); Ronald K. Chang, West Point, PA (US); Xing Dai, Kenilworth, NJ (US); Hong Liu, Kenilworth, NJ (US); John A. McCauley, West Point, PA (US); Wei Li, Kenilworth, NJ (US); Kallol Basu, Kenilworth, NJ (US); Jack D. Scott, Kenilworth, NJ (US); Michael Miller, Kenilworth, NJ (US)

(72) Inventors: Duane DeMong, Somerset, NJ (US); Thomas J. Greshock, Collegeville, PA (US); Ronald K. Chang, Oreland, PA (US); Xing Dai, Cranford, NJ (US); Hong Liu, Hillsborough, NJ (US); John A. McCauley, Maple Glen, PA (US); Wei Li, Belle Mead, NJ (US); Kallol Basu, Piscataway, NJ (US); Jack D. Scott, Scotch Plains, NJ (US); Michael Miller, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/912,761

(22) PCT Filed: Aug. 18, 2014

(86) PCT No.: PCT/US2014/051401
§ 371 (c)(1),
(2) Date: Feb. 18, 2016

(87) PCT Pub. No.: WO2015/026683
PCT Pub. Date: Feb. 26, 2015

(65) Prior Publication Data
US 2016/0200722 A1    Jul. 14, 2016

Related U.S. Application Data

(60) Provisional application No. 61/868,622, filed on Aug. 22, 2013.

(51) Int. Cl.
*A61K 31/44* (2006.01)
*C07D 471/04* (2006.01)
*C07D 498/04* (2006.01)
*C07D 519/00* (2006.01)
*C07D 487/04* (2006.01)

(52) U.S. Cl.
CPC ......... *C07D 471/04* (2013.01); *C07D 487/04* (2013.01); *C07D 498/04* (2013.01); *C07D 519/00* (2013.01)

(58) Field of Classification Search
USPC .......................................... 514/303; 546/119
See application file for complete search history.

(56) References Cited

U.S. PATENT DOCUMENTS

| | | | |
|---|---|---|---|
| 2010/0317646 A1* | 12/2010 | Mciver | ............... C07D 471/04 514/210.18 |
| 2012/0329780 A1 | 12/2012 | Thormann et al. | |
| 2012/0329785 A1 | 12/2012 | Thormann et al. | |
| 2013/0039906 A1* | 2/2013 | Do | ....................... C07D 471/04 424/133.1 |

FOREIGN PATENT DOCUMENTS

| | | |
|---|---|---|
| WO | 2006058074 A1 | 6/2006 |
| WO | 2010017046 A1 | 2/2010 |
| WO | 2010083145 A1 | 7/2010 |
| WO | 2011141756 | 11/2011 |
| WO | WO2012058193 | 5/2012 |
| WO | WO2012118679 | 9/2012 |
| WO | WO2012143144 | 10/2012 |
| WO | 2012135631 A1 | 2/2013 |
| WO | 2013024002 A1 | 2/2013 |
| WO | 2014134774 | 9/2014 |
| WO | 2014137719 A1 | 9/2014 |
| WO | 2014137725 A1 | 9/2014 |
| WO | WO2014137728 | 9/2014 |
| WO | 2015073344 A1 | 5/2015 |

OTHER PUBLICATIONS

Do et al. CAS: 158:331199, 2013.*

* cited by examiner

*Primary Examiner* — Rei-Tsang Shiao
(74) *Attorney, Agent, or Firm* — Keith D. MacMillan; John C. Todaro

(57) ABSTRACT

The present invention is directed to azaindazole compounds which are potent inhibitors of LRRK2 kinase and useful in the treatment or prevention of diseases in which the LRRK2 kinase is involved, such as Parkinson's Disease. The invention is also directed to pharmaceutical compositions comprising these compounds and the use of these compounds and compositions in the prevention or treatment of such diseases in which LRRK-2 kinase is involved.

9 Claims, No Drawings

COMPOUNDS INHIBITING LEUCINE-RICH REPEAT KINASE ENZYME ACTIVITY

BACKGROUND OF THE INVENTION

Parkinson's disease (PD) is a common neurodegenerative disease caused by progressive loss of mid-brain dopaminergic neurons leading to abnormal motor symptoms such as bradykinesia, rigidity and resting tremor. Many PD patients also experience a variety of non-motor symptoms including cognitive dysfunction, autonomic dysfunction, emotional changes and sleep disruption. The combined motor and non-motor symptoms of Parkinson's disease severely impact patient quality of life.

While the majority of PD cases are idiopathic, there are several genetic determinants such as mutations in SNCA, Parkin, PINK1, DJ-1 and LRRK2. Linkage analysis studies have demonstrated that multiple missense mutations in the Leucine-Rich Repeat Kinase 2 (LRRK2) gene lead to an autosomal late onset form of PD. LRRK2 is a 286 kDa cytoplasmic protein containing kinase and GTPase domains as well as multiple protein-protein interaction domains. See for example, Aasly et al., Annals of Neurology, Vol. 57(5), May 2005, pp. 762-765; Adams et al., Brain, Vol. 128, 2005, pp. 2777-85; Gilks et al., Lancet, Vol. 365, Jan. 29, 2005, pp. 415-416, Nichols et al., Lancet, Vol. 365, Jan. 29, 2005, pp. 410-412, and U. Kumari and E. Tan, FEBS journal 276 (2009) pp. 6455-6463.

In vitro biochemical studies have demonstrated that LRRK2 proteins harboring the PD associated proteins generally confer increased kinase activity and decreased GTP hydrolysis compared to the wild type protein (Guo et al., Experimental Cell Research, Vol, 313, 2007, pp. 3658-3670) thereby suggesting that small molecule LRRK2 kinase inhibitors may be able to block aberrant LRRK2-dependent signaling in PD. In support of this notion, it has been reported that inhibitors of LRRK2 are protective in models of PD (Lee et al., Nature Medicine, Vol 16, 2010, pp. 998-1000).

LRRK2 protein has also been demonstrated to be associated with Lewy bodies, a pathological hallmark of PD as well as other neurodegenerative diseases such as Lewy body dementia (Zhu et al., Molecular Neurodegeneration, Vol 30, 2006, pp. 1-17) thereby suggesting that LRRK2 may be associated with the pathogenesis of these diseases.

A growing body of evidence also suggests a role for LRRK2 in immune cell function in the brain with LRRK2 inhibition demonstrated to attenuate microglial inflammatory responses (Moehle et al., The Journal of Neuroscience Vol 32, 2012, pp. 1602-1611). Neuroinflammation is a hallmark of a number of neurodegenerative diseases such as PD and Alzheimer's disease, thereby suggesting that LRRK2 inhibitors may have utility in the treatment of neuroinflammation in these disorders.

Genome-wide association studies also highlight LRRK2 in the modification of susceptibility to the chronic autoimmune Crohn's disease and leprosy (Zhang et al., The New England Jopuranl of Medicine, Vol 361, 2009, pp. 2609-2618; Umeno et al., Inflammatory Bowel Disease Vol 17, 2011, pp. 2407-2415). LRRK2 is also associated with certain types of cancer, e.g. melanoma as well as renal and thyroid carcinomas (Saunders-Pullman et al., Movement Disorders, Vol 25, 2010, pp. 2536-2541; Looyenga, et al., Proceedings of the National Academy of Sciences, USA, Vol 108, 2011, pp. 1439-1444).

Accordingly, compounds and compositions effective at modulating LRRK2 activity may provide a treatment for neurodegenerative diseases such as Parkinson's disease, Lewy body dementia, neuroinflammation, and for disease such as Crohn's disease, leprosy and cancer.

SUMMARY OF THE INVENTION

The present invention is directed to azaindazole compounds which are potent inhibitors of LRRK2 kinase and may be useful in the treatment or prevention of diseases in which the LRRK2 kinase is involved, such as Parkinson's Disease. The invention is also directed to pharmaceutical compositions comprising these compounds and the use of these compounds and compositions in the prevention or treatment of such diseases in which LRRK-2 kinase is involved.

DETAILED DESCRIPTION OF THE INVENTION

The present invention is directed to compounds of Formula I:

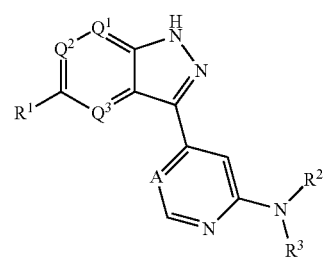

I or a pharmaceutically acceptable salt thereof, wherein:
wherein $R^1$ is selected from the group consisting of:
  a) hydrogen,
  b) halo,
  c) cyano,
  d) hydroxyl,
  e) $C_{2-6}$ alkenyl, which is optionally substituted with one to three substitutents independently selected from the group consisting of halo, cyano and $R^5$;
  f) $OC_{2-6}$ alkenyl, which is optionally substituted with one to three substitutents independently selected from the group consisting of halo, cyano and $R^5$;
  g) $R^5$,
  h) $OR^5$,
  i) $R^7$,
  j) $S(O)_m R^5$,
  k) $S(O)_m R^7$,
  l) $(C=O)R^7$,
  m) $(C=O)R^5$,
  n) $(C=O)OR^5$,
  o) $NR^c R^d$ and p) 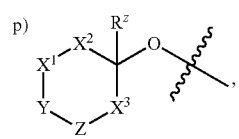, $X^1$, $X^2$ and $X^3$ are each independently selected from the group consisting of a bond or $CR^eR^f$;

Y is O, $CR^aR^b$ or $NR^c$;

Z is O, $CR^aR^b$ or $NR^c$;

$R_z$ is selected from the group consisting of hydrogen and $C_{1-3}$ alkyl, which is optionally substituted with one to three substituents independently selected from the group consisting of halo, hydroxyl, cyano, $NH(C_{1-3}$ alkyl), $N(C_{1-3}$ alkyl)$_2$, $OC_{1-6}$ alkyl and $C_{3-8}$ cycloalkyl;

$Q^1$ is CH or N;

$Q^2$ is CH or N;

$Q^3$ is CH or N;

provided that at least one of $Q^1$, $Q^2$ or $Q^3$ must be N;

A is CH or N;

$R^2$ is selected from the group consisting of hydrogen and $C_{1-6}$ alkyl, which is optionally substituted with one to three substitutents independently selected from the group consisting of:
  a) halo,
  b) cyano,
  c) $R^5$,
  d) $R^7$,
  e) $OR^5$ and
  f) $NR^cR^d$;

$R^3$ is selected from the group consisting of:
  a) hydrogen,
  b) $C_{1-6}$ alkyl, which is optionally substituted with one to three substitutents independently selected from the group consisting of halo, cyano, $OR^5$ and $NR^cR^d$,
  c) $C_{3-8}$ cycloalkyl, which is optionally substituted with one to three substitutents independently selected from the group consisting of halo, cyano, $OR^5$ and $NR^cR^d$,
  d) heterocyclyl, which is optionally substituted with one to three substitutents independently selected from the group consisting of halo, cyano, oxo, $R^5$, $OR^5$ and $NR_cR^d$,
  e) heteroaryl, which is optionally substituted with one to three substitutents independently selected from the group consisting of halo, cyano, oxo, $R^5$, $OR^5$ and $NR^cR^d$;
  f) $C_{4-8}$ cycloalkenyl, which is optionally substituted with one to three substitutents independently selected from the group consisting of halo, cyano, $OR^5$ and $NR^cR^d$,
  g) (C=O)$R^7$,
  h) (C=O)$R^5$,
  i) $S(O)_mR^5$ and
  j) $S(O)_mR^7$;

or $R^2$ and $R^3$ can be taken together with the atoms to which they are attached to form a 3 to 8 membered heterocyclic or heteroaryl ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
  a) halo,
  b) oxo,
  c) cyano,
  d) $OR^5$,
  e) $NR^cR^d$,
  f) $SO_3H$,
  g) $S(O)_mR^5$,
  h) $S(O)_mR^7$,
  i) $R^5$,
  j) $R^6$,
  k) $R^7$,
  l) (C=O)$R^5$,
  m) (C=O)$OR^5$,
  n) (C=O)$R^7$ and
  o) (C=O)$NR^cR^d$;

$R^5$ is selected from the group consisting of hydrogen and $C_{1-6}$ alkyl, which is optionally substituted with one to three substituents independently selected from the group consisting of:
  a) halo,
  b) hydroxyl,
  c) $OC_{1-6}$ alkyl,
  d) $NR^cR^d$,
  e) (C=O)$NR^cR^d$,
  $S(O)_mR^8$,
  g) $S(O)_mR^7$,
  h) $R^7$ and
  i) $OR^7$;

$R^6$ is $C_{1-6}$ alkyl, which is optionally substituted with one to three substituents independently selected from the group consisting of halo and hydroxyl;

or $R^5$ and $R^6$ can be taken together with the atoms to which they are attached to form a 4 to 8 membered heterocyclic, 3 to 8 membered carbocyclic, aryl or heteroaryl ring, wherein said heterocyclic and heteroaryl rings may contain from one to three heteroatoms selected from N, O and S, wherein said heterocyclic, carbocyclic, aryl and heteroaryl rings are optionally substituted with one to three substituents independently selected from the group consisting of:
  a) halo,
  b) oxo,
  c) cyano,
  d) hydroxyl,
  e) $C_{1-3}$ alkyl, which is optionally substituted with one to three halo,
  f) $C_{3-8}$ cycloalkyl,
  g) $OC_{1-3}$ alkyl, which is optionally substituted with one to three halo, and
  h) $OC_{3-8}$ cycloalkyl;

$R^7$ is selected from the group consisting of $C_{4-8}$ heterocyclyl, $C_{3-8}$ cycloalkyl, $C_{4-8}$ cycloalkenyl, aryl and heteroaryl, wherein said heterocyclyl, cycloalkyl, cycloalkenyl, aryl and heteroaryl groups are optionally substituted with one to three substituents independently selected from the group consisting of:
  a) halo,
  b) cyano,
  c) hydroxyl,
  d) oxo,
  e) $C_{1-3}$ alkyl, which is optionally substituted with one to four substituents independently selected from the group consisting of hydroxyl, halo, cyano, heterocyclyl, $OC_{1-3}$ alkyl and $NR^cR^d$,
  f) $OC_{1-3}$ alkyl, which is optionally substituted with one to four substituents independently selected from the group consisting of hydroxyl, halo, cyano, heterocyclyl, $OC_{1-3}$ alkyl, $NR^cR^d$, aryl and heteroaryl,
  g) $C_{3-8}$ cycloalkyl, which is optionally substituted with one to four substituents independently selected from the group consisting of hydroxyl, halo, cyano, heterocyclyl, $OC_{1-3}$ alkyl and $NR^cR^d$,
  h) aryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$,
  i) heteroaryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$, j) heterocyclyl, which is optionally substituted with one to four substituents independently selected from the group consisting of hydroxyl, halo, cyano, $OC_{1-3}$ alkyl and $NR^cR^d$, k) $C_{4-8}$ cycloalkenyl, which is optionally substituted with one to four substituents independently selected from the group consisting of hydroxyl, halo, cyano, heterocyclyl, $OC_{1-3}$ alkyl and $NR^cR^d$;

$R^8$ is hydrogen or $C_{1-6}$ alkyl, which is optionally substituted with one to three substituents independently selected from the group consisting of:
  a) halo,
  b) cyano,
  c) hydroxyl,
  d) $OC_{1-3}$ alkyl, which is optionally substituted with one to four substituents independently selected from the group consisting of hydroxyl, halo and $NR^cR^d$, and
  e) $C_{3-8}$ cycloalkyl;

$R^a$ is selected from the group consisting of hydrogen and $C_{1-6}$ alkyl;

$R^b$ is selected from the group consisting of hydrogen and $C_{1-6}$ alkyl;

$R^c$ is selected from the group consisting of:
  a) hydrogen,
  b) $C_{1-3}$ alkyl, which is optionally substituted with one to three substituents independently selected from the group consisting of halo, hydroxyl, cyano, heteroaryl, aryl, $NH(C_{1-3}$ alkyl), $N(C_{1-3}$ alkyl)$_2$, $OC_{1-6}$ alkyl and $C_{3-8}$ cycloalkyl;

$R^d$ is selected from the group consisting of:
  a) hydrogen,
  b) $C_{3-8}$ cycloalkyl,
  c) $C_{3-6}$ heterocyclyl,
  d) $C_{1-3}$ alkyl,
  e) $(C=O)C_{1-3}$ alkyl,
  f) aryl and
  g) heteroaryl;

wherein said cycloalkyl, heterocyclyl, alkyl, aryl and heteroaryl groups are each optionally substituted with one to three substituents independently selected from the group consisting of halo, hydroxyl, cyano, $R^8$, $SO_2R^8$, $OC_{1-6}$ alkyl and $C_{3-8}$ cycloalkyl; or $R^c$ and $R^d$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of halo, cyano, hydroxyl, $C_{1-3}$ alkyl and $OC_{1-3}$ alkyl;

$R^e$ is selected from the group consisting of hydrogen and $C_{1-3}$ alkyl;

$R^f$ is selected from the group consisting of hydrogen and $C_{1-3}$ alkyl;

m is an integer from zero to two.

In a class of the invention, $X^1$ is a bond. In another class of the invention, $X^1$ is $CR^eR^f$.

In a class of the invention, $X^2$ is a bond. In another class of the invention, $X^2$ is $CR^eR^f$.

In a class of the invention, $X^3$ is a bond. In another class of the invention, $X^3$ is $CR^eR^f$.

In a class of the invention, Y is O. In another class of the invention, Y is $CR^aR^b$. In another class of the invention, Y is $NR^c$.

In a class of the invention, Z is O. In another class of the invention, Z is $CR^aR^b$. In another class of the invention, Z is $NR^c$.

In a class of the invention, $Q^1$ is CH. In another class of the invention, $Q^1$ is N.

In a class of the invention, $Q^2$ is CH. In another class of the invention, $Q^2$ is N.

In a class of the invention, $Q^3$ is CH. In another class of the invention, $Q^3$ is N.

In a class of the invention, A is CH. In another class of the invention, A is N.

In a class of the invention, $R^1$ is selected from the group consisting of $R^5$, $OR^5$, $R^7$ and

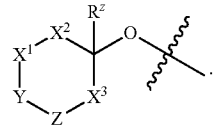

In a subclass of the invention, $R^1$ is selected from the group consisting of $OR^5$ and

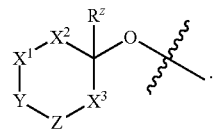

In a further subclass of the invention, $R^1$ is selected from the group consisting of: $OC_{1-3}$ alkyl, aryl and heteroaryl, wherein said aryl and heteroaryl groups are optionally substituted with one to three substituents independently selected from the group consisting of halo, hydroxyl, $C_{1-3}$ alkyl and $OC_{1-3}$ alkyl.

In a class of the invention, $R^2$ and $R^3$ are taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
  a) halo,
  b) oxo,
  c) cyano,
  d) $OR^5$,
  e) $NR^cR^d$,
  f) $SO_3H$
  g) $S(O)_mR^5$,
  h) $S(O)_mR^7$,
  i) $R^5$,
  j) $R^6$,
  k) $R^7$,
  l) $(C=O)R^5$,
  m) $(C=O)OR^5$,
  n) $(C=O)R^7$ and
  o) $(C=O)NR^cR^d$.

In a subclass of the invention, $R^2$ and $R^3$ can be taken together with the atoms to which they are attached to form a 6 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:

a) halo,
b) oxo,
c) $OR^5$,
d) $NR^cR^d$,
e) $S(O)_mR^5$,
f) $S(O)_mR^7$,
g) $R^6$,
h) $R^7$,
i) $(C=O)R^5$,
j) $(C=O)OR^5$ and
k) $(C=O)R^7$.

In a further subclass of the invention, $R^2$ and $R^3$ can be taken together with the atoms to which they are attached to form a morpholinyl group, which is optionally substituted with $C_{1-6}$ alkyl or $C_{1-6}$ alkylhydroxyl. In a further subclass of the invention, $R^2$ and $R^3$ can be taken together with the atoms to which they are attached to form a piperazinyl group, which is optionally substituted with $C_{1-6}$ alkyl or $SO_2$—$C_{1-6}$ alkyl-. In a further subclass of the invention, $R^2$ and $R^3$ can be taken together with the atoms to which they are attached to form a piperazinone group.

In a class of the invention, $R^5$ is selected from the group consisting of hydrogen or $C_{1-6}$ alkyl, which is optionally substituted with one to three substituents independently selected from the group consisting of: halo, hydroxyl, $S(O)_m$ $R^8$ and $R^7$.

In a class of the invention, $R^7$ is $C_{4-8}$ heterocyclyl.
In a class of the invention, $R^a$ is hydrogen.
In a class of the invention, $R^b$ is hydrogen.
In a class of the invention, $R^c$ is hydrogen.
In a class of the invention, $R^d$ is hydrogen.
In a class of the invention, $R^e$ is hydrogen.
In a class of the invention, $R^f$ is hydrogen.

Reference to the preferred classes and subclasses set forth above is meant to include all combinations of particular and preferred groups unless stated otherwise.

Specific embodiments of the present invention include, but are not limited to the compounds identified herein as Examples A1 to AB1, or pharmaceutically acceptable salts thereof.

The invention also encompasses a pharmaceutical composition which comprises an inert carrier and the compound of Formula I, or a pharmaceutically acceptable salt thereof.

The invention may also encompass a method of treating Parkinson's Disease in a mammalian patient in need of such treatment, which comprises administering to the patient a therapeutically effective amount of the compound of Formula I, or a pharmaceutically acceptable salt thereof.

The invention may also encompass the use of a compound of Formula I, or a pharmaceutically acceptable salt thereof, and a pharmaceutically acceptable carrier, for the manufacture of a medicament for the treatment of Parkinson's Disease.

The invention is also directed to medicaments or pharmaceutical compositions which may be useful for treating diseases or disorders in which LRRK2 is involved, such as Parkinson's Disease, which comprise a compound of Formula I, or a pharmaceutically acceptable salt thereof, and a pharmaceutically acceptable carrier.

The invention is also directed to the use of a compound of Formula I which may be useful for treating diseases or disorders in which LRRK2 is involved, such as Parkinson's Disease.

The invention is further directed to a method for the manufacture of a medicament or a composition which may be useful for treating diseases or disorders in which LRRK2 is involved, such as Parkinson's Disease, comprising combining a compound of Formula I with one or more pharmaceutically acceptable carriers.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Unless a specific stereochemistry is indicated, the present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Tautomers of compounds defined in Formula I are also included within the scope of the present invention. For example, compounds including carbonyl —$CH_2C(O)$— groups (keto forms) may undergo tautomerism to form hydroxyl —CH═C(OH)— groups (enol forms). Both keto and enol forms are included within the scope of the present invention.

When any variable (e.g. $R^5$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be understood as meaning that the group in question is either unsubstituted or may be substituted with one or more substituents.

As used herein, "alkyl" is intended to mean linear or branched structures having no carbon-to-carbon double or triple bonds. Thus, $C_{1-4}$ alkyl is defined to identify the group as having 1, 2, 3 or 4 carbons in a linear or branched arrangement, such that $C_{1-4}$ alkyl specifically includes, but is not limited to, methyl, ethyl, n-propyl, iso-propyl, n-butyl, iso-butyl and tert-butyl.

As appreciated by those of skill in the art, "halo" or "halogen" as used herein is intended to include chloro (Cl), fluoro (F), bromo (Br) and iodo (I).

The term "cycloalkyl" shall mean cyclic rings of alkanes of three to eight total carbon atoms, unless otherwise indicated, or any number within this range (i.e., cyclopropyl, cyclobutyl, cyclopentyl, cyclohexyl, cycloheptyl, methyl-cyclopropyl, 2,2-dimethyl-cyclobutyl, 2-ethyl-cyclopentyl or cyclooctyl) and also includes bicyclic or fused spirocyclic compounds.

The term "cycloalkenyl" shall mean cyclic rings of four to eight total carbon atoms, unless otherwise indicated, or any number within this range where one or two degrees of unsaturation are present. Non-limiting examples of said cycloalkenyl groups are: cyclohexenyl, cyclopentenyl, cyclooctadienyl.

The term "carbocycle" shall mean cyclic rings of three to eight total carbon atoms, unless otherwise indicated, or any number within this range, where zero, one or two degrees of unsaturation are present and where said "carbocycle" can be bicyclic or fused spirocyclic in nature. Non-limiting examples of said carbocyclyl groups are: cyclohexenyl, cyclopentenyl, cyclooctadienyl, cyclohexyl or cyclopropyl.

If no number of carbon atoms is specified, the term "alkenyl" refers to a non-aromatic hydrocarbon radical, straight or branched, containing from 2 to 10 carbon atoms and at least 1 carbon to carbon double bond. Preferably 1 carbon to carbon double bond is present, and up to 4 non-aromatic carbon-carbon double bonds may be present. Thus, "C2-C6 alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

The term "heteroaryl", as used herein, represents a stable monocyclic, bicyclic or tricyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "heterocycle" or "heterocyclyl" as used herein is intended to mean a 5- to 10-membered nonaromatic ring, unless otherwise specified, containing from 1 to 4 heteroatoms selected from the group consisting of O, N, S, SO, or $SO_2$ and includes bicyclic groups. The heterocyclyl group also includes rings that possess one or two degrees of unsaturation. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl, azetidinyl and the like. If the heterocycle contains a nitrogen, it is understood that the corresponding N-oxides thereof are also emcompassed by this definition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Salts in the solid form may exist in more than one crystal structure, and may also be in the form of hydrates. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Salts derived from inorganic bases include aluminum, ammonium, calcium, copper, ferric, ferrous, lithium, magnesium, manganic salts, manganous, potassium, sodium, zinc, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. Similarly, the salts of the acidic compounds are formed by reactions with the appropriate inorganic or organic base. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which may be selected from the group consisting of the compounds disclosed in the following Examples and pharmaceutically acceptable salts thereof and individual diastereomers thereof.

The subject compounds are useful in a method of inhibition of LRRK2 receptors in a patient such as a mammal in need of such antagonism comprising the administration of an effective amount of the compound. The present invention is directed to the use of the compounds disclosed herein as inhibitors of LRRK2 receptors. In addition to primates, especially humans, a variety of other mammals can be treated according to the method of the present invention.

Another embodiment of the present invention is directed to a method for the treatment, control, amelioration, or reduction of risk of a disease or disorder in which the LRRK2 kinase is involved in a patient that comprises administering to the patient a therapeutically effective amount of a compound that is an inhibitor of LRRK2 kinase.

The present invention is further directed to a method for the manufacture of a medicament for inhibition of LRRK2 receptors activity in humans and animals comprising combining a compound of the present invention with a pharmaceutical carrier or diluent.

The subject treated in the present methods is generally a mammal, for example a human being, male or female, in whom inhibition of LRRK2 kinase activity is desired. The term "therapeutically effective amount" means the amount of the subject compound that will elicit the biological or medical response of a tissue, system, animal or human that is being sought by the researcher, veterinarian, medical doctor or other clinician.

The terms "treating" or "treatment" of a disease as used herein includes: inhibiting the disease, i.e., arresting or reducing the development of the disease or its clinical symptoms; or relieving the disease, i.e., causing regression of the disease or its clinical symptoms. The term "preventing" or "prevention" of a disease as used herein includes: causing the clinical symptoms of the disease not to develop in a mammal that may be exposed to or predisposed to the disease but does not yet experience or display symptoms of the disease, and the like.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The ability of the compounds of the present invention to act as LRRK2 kinase inhibitors may make them useful pharmacological agents for disorders that involve LRRK2 kinase in humans and animals, but particularly in humans.

In another embodiment the invention provides a method of inhibiting LRRK2 Kinase activity (this is to say, inhibiting the kinase activity associated with Leucine-Rich Repeat Kinase 2 [LRRK2], a multidomain protein containing kinase and GTPase enzymatic activities) in a patient in need of therapy for a condition amenable to treatment by such kinase activity inhibition, for example, treatment or prevention of neurologic damage associated with Parkinson's disease, for example, improvement in dopaminergic tone and in providing symptomatic benefit, for example, in treating, alleviating, ameliorating, or managing motor and non-motor symptoms of Parkinson's disease, and other conditions that may be treated or prevented by inhibition of LRRK2 kinase. Of particular importance is the acute or prophylactic treatment of Parkinson's Disease.

The subject compounds may be further useful in a method for the prevention, treatment, control, amelioration, or reduction of risk of the diseases, disorders and conditions noted herein.

The subject compounds may be further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with one or more additional therapeutic agents, for example: L-DOPA; dopaminergic agonists such as quinpirole, ropinirole, pramipexole, pergolide and bromocriptine; MAO-B inhibitors such as rasagiline, deprenyl and selegiline; DOPA decarboxylase inhibitors such as carbidopa and benserazide; and COMT inhibitors such as tolcapone and entacapone; or potential therapies such as an adenosine A2a antagonists, metabotropic glutamate receptor 4 modulators, or growth factors such as brain derived neurotrophic factor (BDNF), and a pharmaceutically acceptable carrier.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require inhibition of LRRK2 kinase activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of Parkinson's Disease, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

General Schemes:

A general procedure for the preparation of $R^7$ substituted compounds such as 1.7 is shown in Scheme 1. Treatment of a suitable compound such as 1.1 with iodine/KOH and the like in a solvent such as MeCN and the like will provide compound 1.2. The indazole can be protected with SEM-Cl and the like to provide the protected indazole 1.3. The iodo group in 1.3 can be subjected to palladium-mediated cross coupling with a boronic acid such as 1.4 and the like to provide compounds such as 1.5. The chloride in 1.5 can be converted into an $R^7$ substituted compound such as 1.6 via palladium-mediated cross coupling between a compound 1.5 and a suitable boronic acid or ester $R^7B(OR)_2$. Removal of the SEM group to afford compounds 1.7 can be accomplished via a number of methods such as heating in the presence of TBAF in THF, treatment with a mixture of 4N HCl in 1,4-dioxane and MeOH, or a two-step procedure involving initial treatment with TFA in $CH_2Cl_2$, followed by treatment with ammonium hydroxide in MeOH and $CH_2Cl_2$.

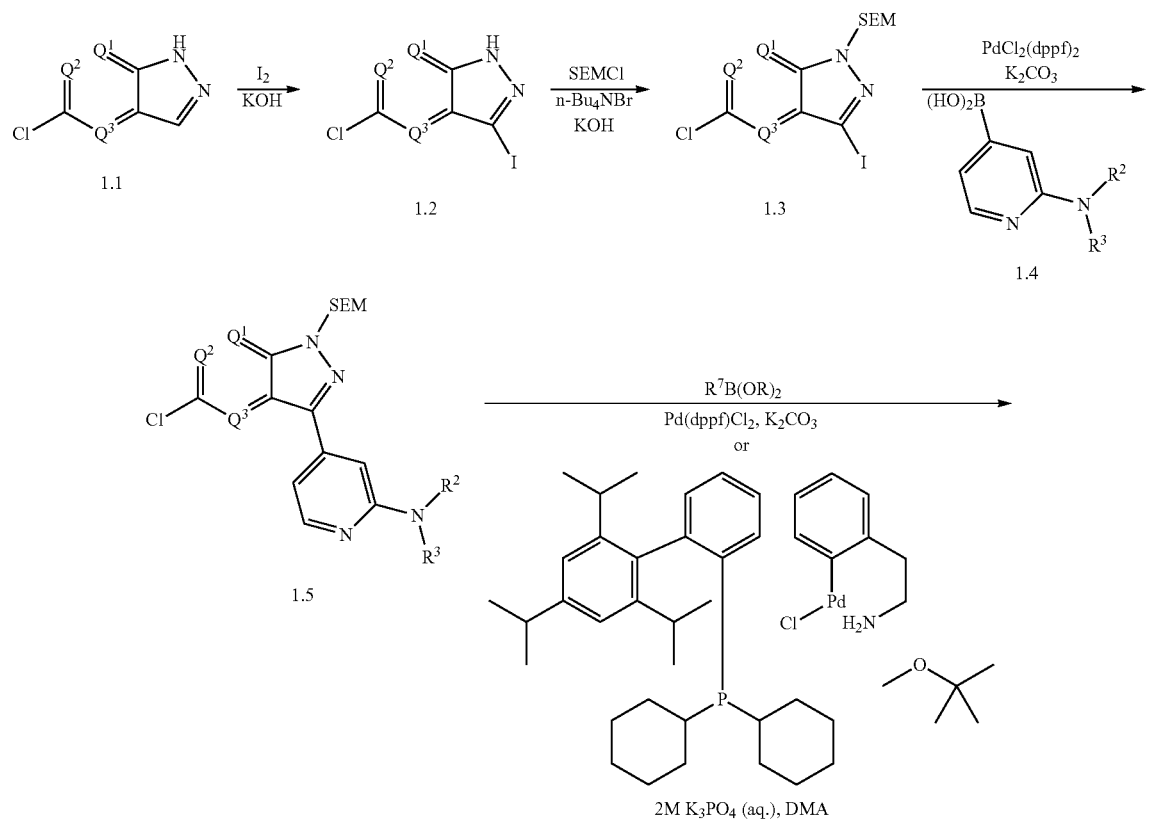

-continued

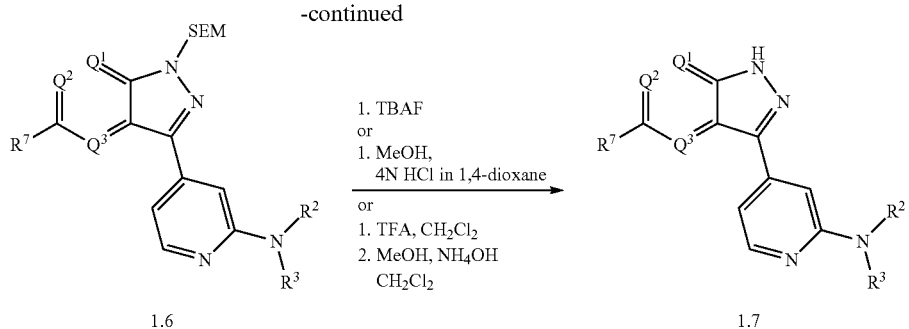

1. TBAF
or
1. MeOH,
   4N HCl in 1,4-dioxane
or
1. TFA, CH$_2$Cl$_2$
2. MeOH, NH$_4$OH
   CH$_2$Cl$_2$ Scheme 2 demonstrates an alternative approach to intermediates such as 1.5. Compound 1.3 can be converted into the fluoropyridine 2.2 using an appropriate palladium catalyst and boronic acid (2.1) and the like. The fluoro-pyridine 2.2 can be converted into the amino-pyridine 1.5 using the appropriate amine (HN(R$^2$)R$^3$) and a base such as triethylamine and the like in a solvent such as DMSO and the like. Compounds 1.5 can be converted into examples such as 1.7 via methods previously described in Scheme 1.

-continued

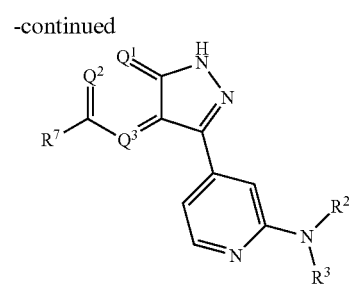

Treatment of 1.2 with NIS followed by TrCl and sodium hydride and the like will provide 3.1 (Scheme 3). Compounds 3.1 can be converted into the pyridyl substituted compound 3.2 via palladium-mediated cross-coupling with a suitable boronic acid 1.4 or analogous boronate. The chloride 3.2 can be converted into the alcohol 3.3 via treatment with Pd$_2$(dba)$_3$, RuPhos, aq. KOH and 1,4-dioxane and the like. The alcohol 3.3 can be converted into compounds such as 3.5 by first alkylating the alcohol with R$^5$—I and Ag$_2$O, followed by removal of the trityl protecting group with methods such as triethylsilane/TFA and the like. Alternatively, the trityl group can be removed with aqueous HCl and the like in a solvent such as ethanol and the like or aqueous TFA and the like with a solvent such as dichloromethane and the like.

Scheme 2

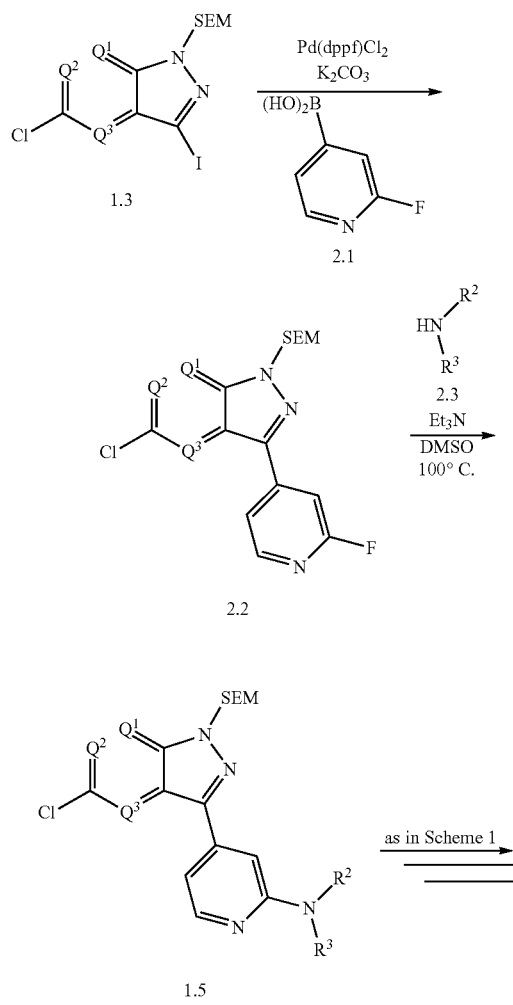

Scheme 3

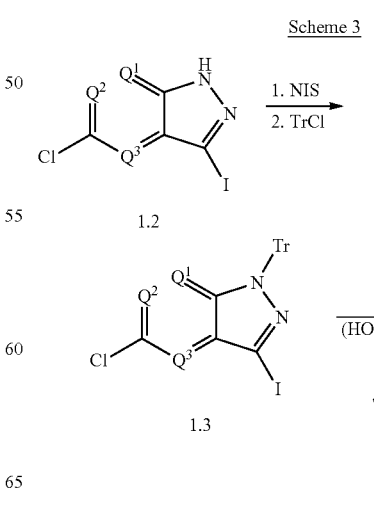

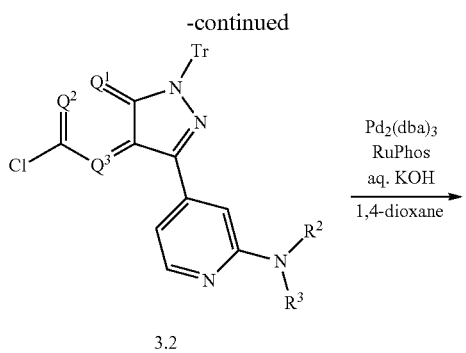

3.2

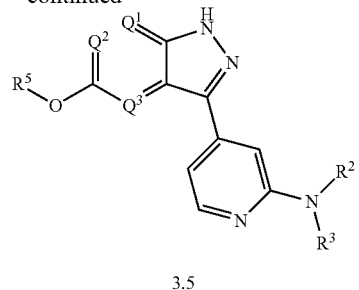

3.5

An additional approach to compounds such as 4.11 is outlined in Scheme 4. Alkylation of 4.1a with a combination of $R^5$—I and silver carbonate and the like will provide compounds 4.2. Alternatively, treatment of a combination of an appropriate alcohol $R^5$—OH and compound 4.1b with rac-BiNAP, $Pd(dba)_2$ and $Cs_2CO_3$ in refluxing toluene will afford compounds 4.2. The nitro derivative 4.2 can be treated with Pd/C in the presence of $HCOONH_4$ to produce the amine 4.3. The amine 4.3 can be acetylated to provide 4.4. The acetamide 4.4 can be treated with iso-amyl nitrate in the presence of $Ac_2O$/KOAc and the like to provide the N-acyl azaindazole 4.5. Compounds such as 4.5 can be treated with ammonia and the like to produce azaindazoles 4.6. The azaindazole 4.6 can be treated with iodine and KOH and the like to provide compounds 4.7. The azaindazole nitrogen can be protected with trityl chloride and a base such as NaH and the like to provide 4.8. Compound 4.8 can be converted into 4.10 via cross coupling using the appropriate boronic acid (4.9) and the like and an appropriate palladium catalyst. The chloro-pyridine 4.10 can be converted into examples such as 4.11 using the appropriate amine ($HN(R^2)R^3$), palladium catalyst, and ligand followed by deprotection of the trityl group using standard conditions.

Scheme 4

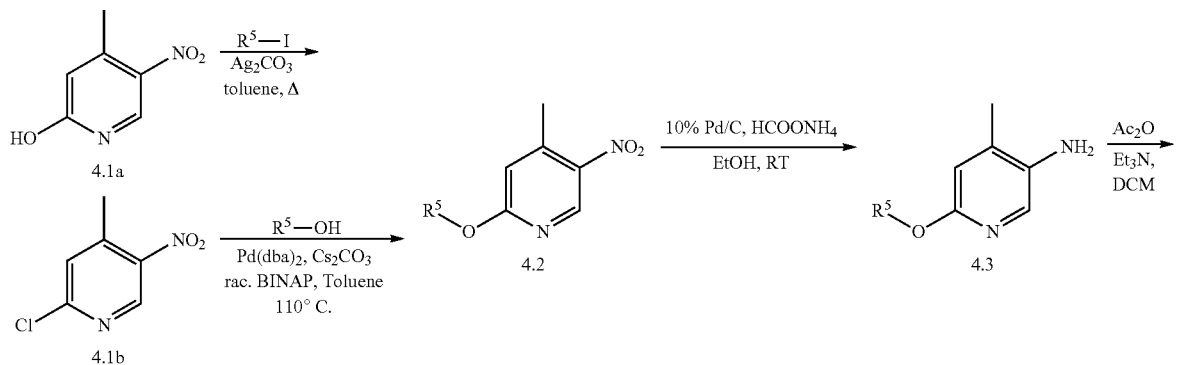

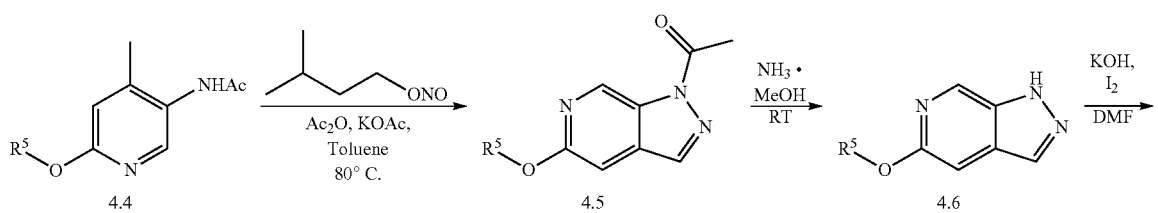

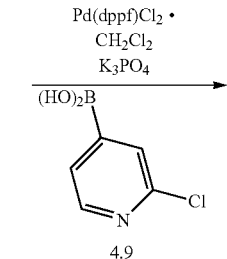
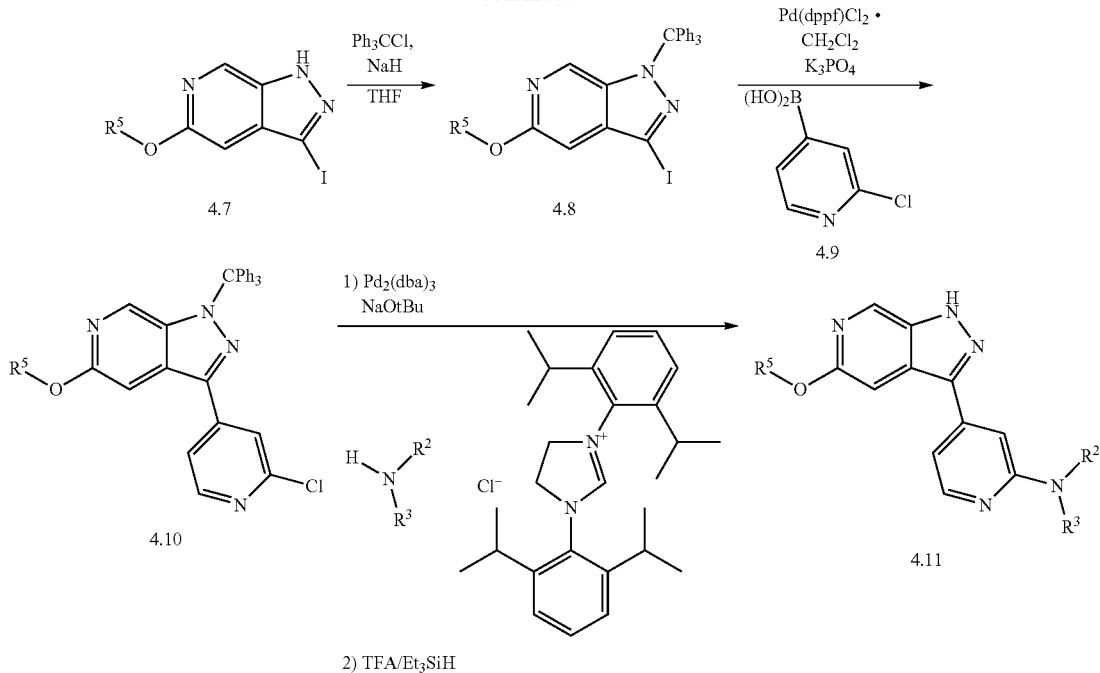

A general procedure for the preparation of certain $R^7$ substituted indazoles such as 1.7 is shown in Scheme 5. Treatment of a suitable compound 5.1 under palladium catalyzed cross coupling conditions with a boronic acid and the like will afford 5.2. Treatment with iodine/$K_2CO_3$ and the like in a solvent such as MeCN and the like will provide compound 5.3. Compounds 5.3 can be treated with a base such as NaH and the like, followed by trityl chloride to provide the protected indazole 5.4. Compounds 5.4 can then undergo palladium-catalyzed cross coupling with the requisite boronic acid to afford 5.5. Palladium or nickel mediated amination of 5.5 with the appropriate amines will provide compounds 5.6. Removal of the trityl group via standard methods will provide compounds 1.7.

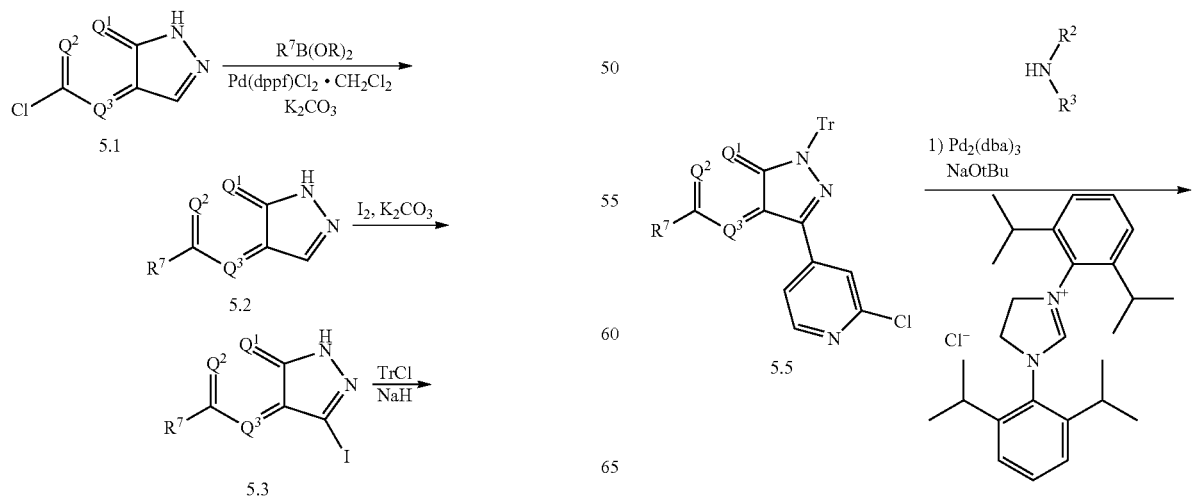

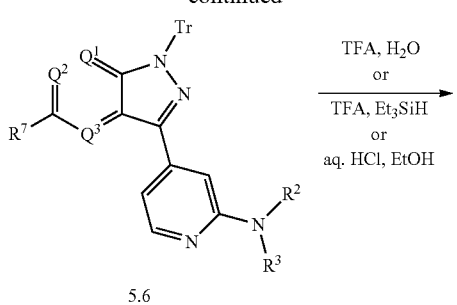

5.6

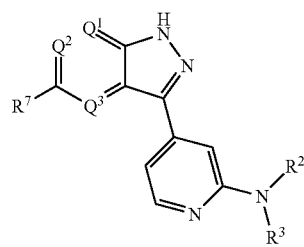

1.7

A method for the preparation of compounds 6.2 is outlined in Scheme 6. Nickel or palladium-mediated amination of 3.2 with the appropriate HNR$^c$R$^d$ will afford compounds 6.1. Deprotection under previously described conditions will afford compounds 6.2.

Scheme 6

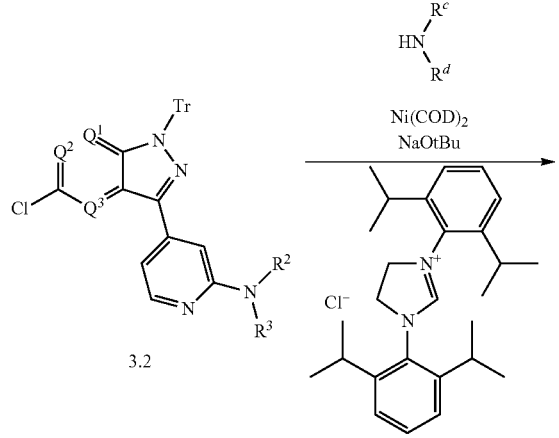

3.2

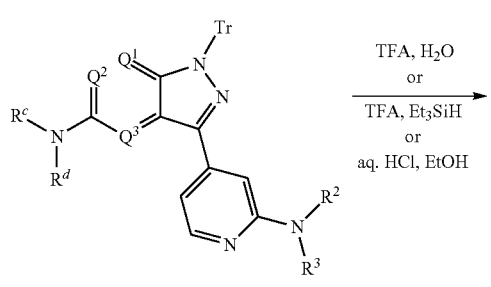

6.1

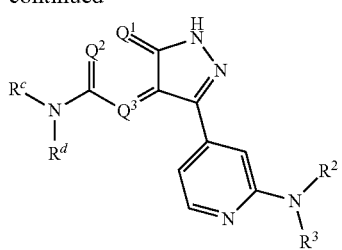

6.2

A general procedure for the preparation of alkoxy substituted azaindazoles such as 7.4 is shown in Scheme 7. The iodo group in 7.1 can be converted to the pinacol boronate ester upon treatment with pinacol diborane under palladium catalyzed conditions and the like followed by treatment under palladium mediated cross coupling conditions with 4,6-dichloropyrimidine to afford 7.2. Treatment with the appropriate amine in solvents such as DMSO and the like with a base such as triethylamine and the like will provide 7.3. Cleavage of the trityl group via means such as those described above will provide examples such as 7.4.

Scheme 7

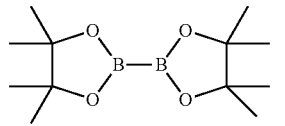

7.1

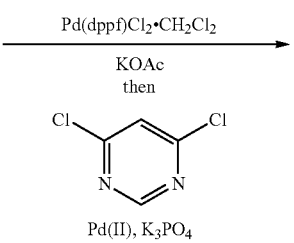

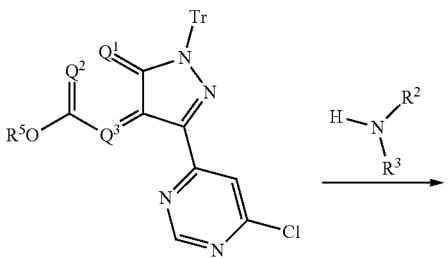

7.2

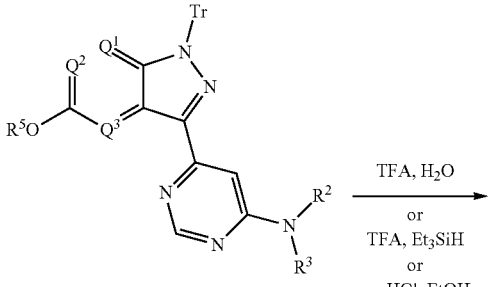

7.3

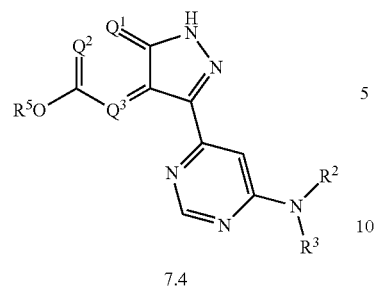

7.4

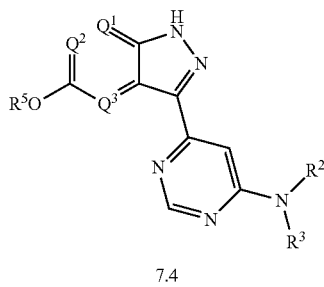

7.4

Alternatively, a general procedure for the preparation substituted indazoles such as 7.4 is shown in Scheme 8. Treatment of compounds 8.1 with SEM-Cl and dicyclohexylmethyl amine and the like will provide 8.2. Deprotonation of 8.2 with n-BuLi and transmetallation with ZnCl$_2$ followed by palladium-catalyzed cross coupling using 4,6-dichloropyrimidine and the like will afford 8.3. Treatment of 8.3 with the appropriate amine in solvents such as DMSO and the like with a base such as triethylamine and the like will provide 8.4. Cleavage of the SEM group with HCl and the like or TFA and the like will provide examples such as 7.4.

Compounds 9.3 can be prepared via a method outlined in Scheme 9. Palladium-mediated C—O coupling of 4.1b and 9.1 will afford compounds 9.2. Conversion of 9.2 to compounds 9.3 can be accomplished via a method similar to that outlined in Scheme 4, Steps 2-9.

Scheme 9

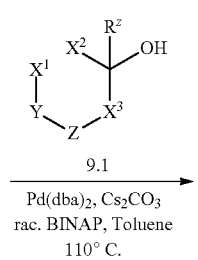

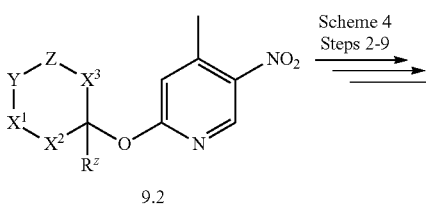

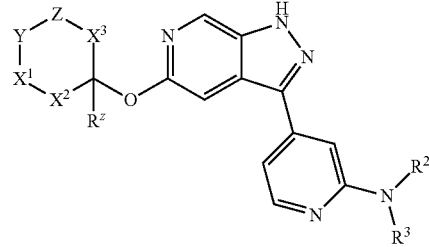

9.3

Scheme 8

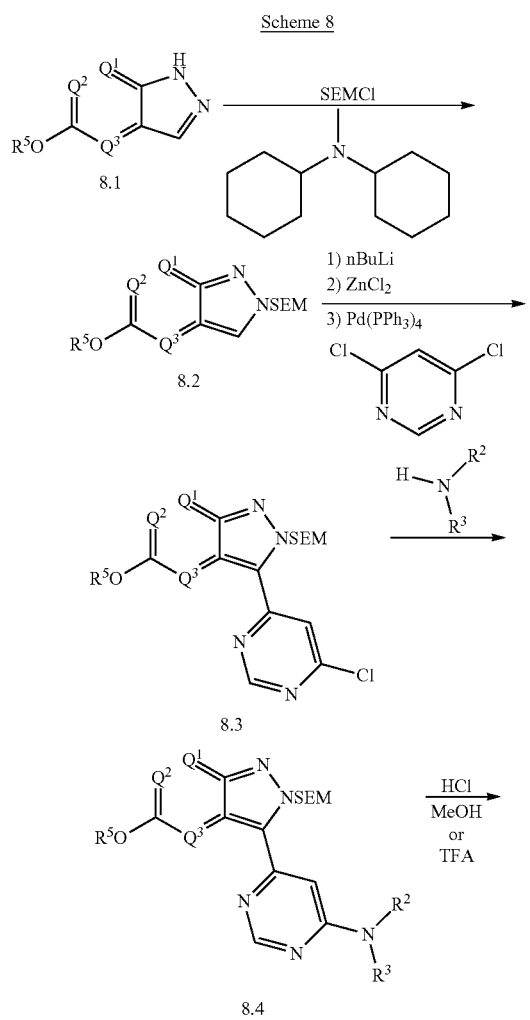

Compounds 10.5 can be accessed from compounds 10.1 via the method outlined in Scheme 10. Treatment of compounds 10.1 with SEM-Cl and dicyclohexylmethyl amine and the like will provide 10.2. Deprotonation of 10.2 with n-BuLi and transmetallation with ZnCl$_2$ followed by palladium catalyzed cross coupling using 4,6-dichloropyrimidine and the like will afford 10.3. Treatment of 10.3 with the appropriate amine in solvents such as DMSO and the like with a base such as triethylamine and the like will provide 10.4. Cleavage of the SEM group with HCl and the like or TFA and the like will provide examples such as 10.5.

Scheme 10

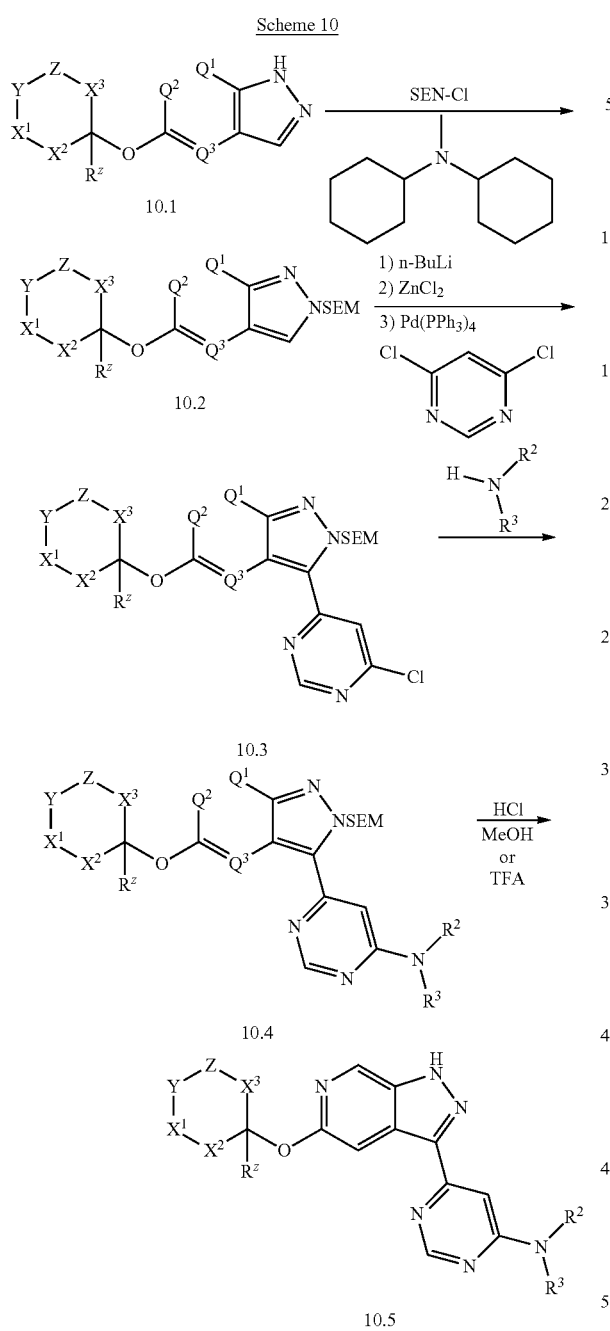

Scheme 11 vents such as DMSO and the like with a base such as triethylamine and the like will provide 11.3. Cleavage of the trityl group via means such as those described above will provide examples such as 10.5.

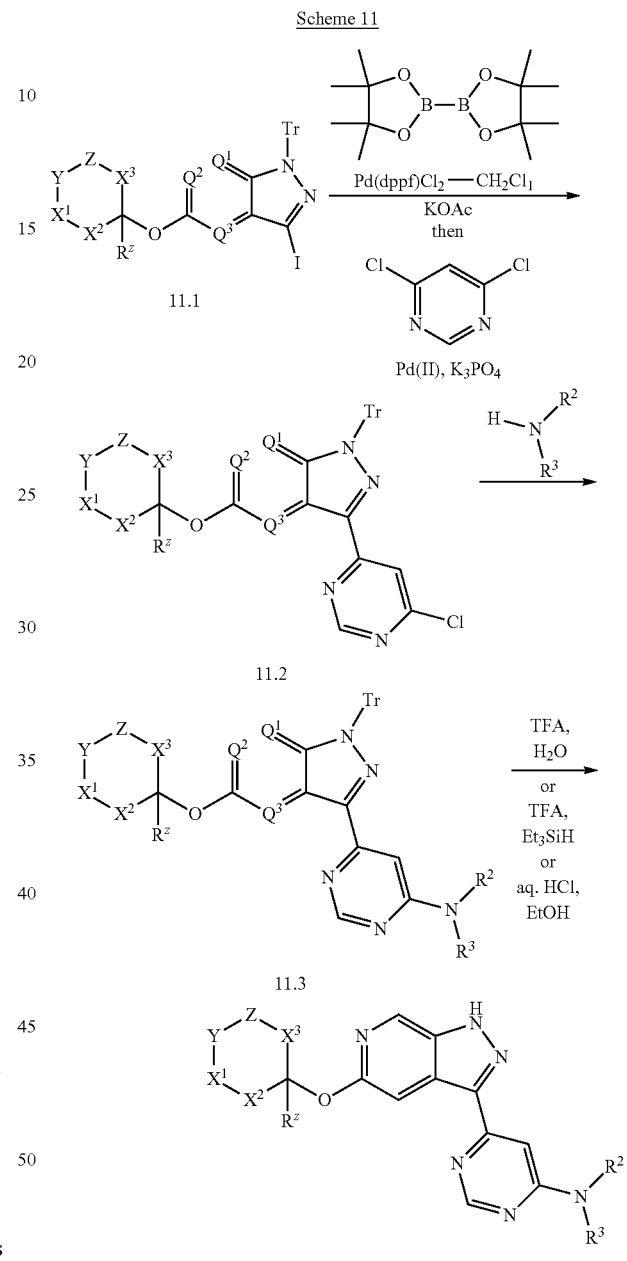

An alternative procedure for the preparation of compounds 10.5 is shown in Scheme 11. The iodo group in 11.1 can be converted to the pinacol boronic ester upon treatment with pinacol diborane under palladium catalyzed conditions and the like followed by treatment under palladium mediated cross coupling conditions with 4,6-dichloropyrimidine to afford 11.2. Treatment with the appropriate amine in sol- Experimentals Abbreviations used in the experimentals may include, but are not limited to the following:

| ACN | Acetonitrile | AcOH | Acetic acid |
|---|---|---|---|
| Aq | Aqueous | Bn | Benzyl |
| BOC | tert-Butoxycarbonyl | BOC$_2$O Boc$_2$O | BOC Anhydride |
| Bu | Butyl | C (or ° C.) | degrees Celsius |
| Cbz | benzyloxycarbonyl | DBU | 1,8-Diazabicyclo[5.4.0]undec-7-ene |

-continued

| | | | |
|---|---|---|---|
| DCM | Dichloromethane | DIPEA | Diisopropylethylamine |
| DEAD | diethylazodicarboxylate | DIAD | diisopropylazodicarboxylate |
| DMA | N,N-Dimethylacetamide | DMAP | 4-Dimethylaminopyridine |
| DME | 1,2-dimethoxyethane | DMF | Dimethylformamide |
| DMSO | Dimethyl sulfoxide | dppf | 1,1'-(bis-diphenylphosphino)ferrocene |
| EDCI | 1-(3-Dimethylaminopropyl)-3-ethylcarbodiimide hydrochloride | EDC | 1-(3-Dimethylaminopropyl)-3-ethylcarbodiimide hydrochloride |
| EI | Electron ionization | Eq | Equivalents |
| Et | Ethyl | EtOAc | Ethyl acetate |
| EtOH | Ethanol | g | grams |
| h, hr | hours | $^1$H | proton |
| HATU | N,N,N',N'-Tetramethyl-O-(7-Azabenzotriazol-1-yl)uronium hexafluorophosphate | Hex | hexanes |
| HOBT | 1-Hydroxybenzotriazole | HOBT.H$_2$O | 1-Hydroxybenzotriazole hydrate |
| HOTS | para-toluene sulfonic acid (see also TsOH) | HOTS.H$_2$O | para-toluene sulfonic acid hydrate (see also TsOH.H$_2$O) |
| HMPA | hexamethylphosphoramide | HPLC | High pressure liquid chromatography |
| IPA | isopropanol, 2-propanol | LDA | lithium diisopropylamide |
| M | Molar | mmol | milimolar |
| mCPBA | meta-Chloroperoxy benzoic acid | Me | Methyl |
| MeCN | Acetonitrile | MeOH | Methanol |
| min | Minutes | mg | Milligrams |
| MHZ | Megahertz | mL (or ml) | Milliliter |
| Mol sieves | molecular sieves | N | normal |
| MTBE | Methyl tert-butyl ether | MPLC | Medium Pressure Liquid Chromatography/flash chromatography |
| NMR | Nuclear Magnetic Resonance | MS | Mass Spectroscopy |
| NBS | N-Bromosuccinimide | NMM | N-Methylmorpholine |
| NIS | N-iodosuccinimide | NMP | 1-methyl-2-pyrrolidone |
| ON | Overnight | PTLC | Preparative thin layer chromatography |
| PyBrOP | Bromo-tris-pyrrolidino-phosphonium hexafluorophosphate | pin | pinacol |
| PyBOP | (Benzotriazol-1-yloxy)tripyrrolidino-phosphonium hexa-fluorophosphate | Pyr | Pyridine |
| dtbpf | 1,1'-Bis(di-tert-butylphosphino)ferrocene | Ni(COD)$_2$ | Bis(1,5-cyclooctadiene)nickel(0) |
| Quant | quantitative | RT or rt | Room temperature |
| sat (or sat. or sat'd.) | Saturated | SFC | supercritical fluid chromatography |
| | | SiliaMetS ® DMT | Silica bound equivalent of 2,4,6-trimercaptotriazine (metal scavenger) |
| sgc | Silica gel 60 chromatography | SiO$_2$ | Silica gel |
| tBOC | tert-Butoxycarbonyl | t-Bu | tert-butyl |
| TEA | Triethylamine | Tf | Trifluoromethane sulfonyl |
| TFA | Trifluoroacetic acid | THF | Tetrahydrofuran |
| TLC | Thin layer chromatography | Ts | Toluene sulfonyl |
| SEM | 2-(Trimethylsilyl)ethoxy-methyl | Tr | Trityl |
| TsOH | para-toluene sulfonic acid | TsOH.H$_2$O | para-toluene sulfonic acid hydrate |
| TBAF | Tetrabutylammonium fluoride | TBS | Tert-butyldimethyl silyl |
| T3P | n-propylphosphonic anhydride | | |
| Xantphos | 4,5-Bis(diphenylphosphino)-9,9-dimethylxanthene | RuPhos | 2-Dicyclohexylphosphino-2',6'-diisopropoxybiphenyl |
| ~ | Approximately | | |

General Experimental Information:

Unless otherwise noted, all reactions are magnetically stirred.

Unless otherwise noted, when ethyl acetate, hexanes, dichloromethane, 2-propanol, and methanol are used in the experiments described below, they are Fisher Optima grade solvents.

Unless otherwise noted, when diethyl ether is used in the experiments described below, it is Fisher ACS certified material and is stabilized with BHT.

Unless otherwise noted, "concentrated to dryness" means evaporating the solvent from a solution or mixture using a rotary evaporator.

Unless otherwise noted, flash chromatography is carried out on an Isco, Analogix, or Biotage automated chromatography system using a commercially available cartridge as the column. Columns may be purchased from Isco, Analogix, Biotage, Varian, or Supelco and are usually filled with silica gel as the stationary phase.

Experimentals:

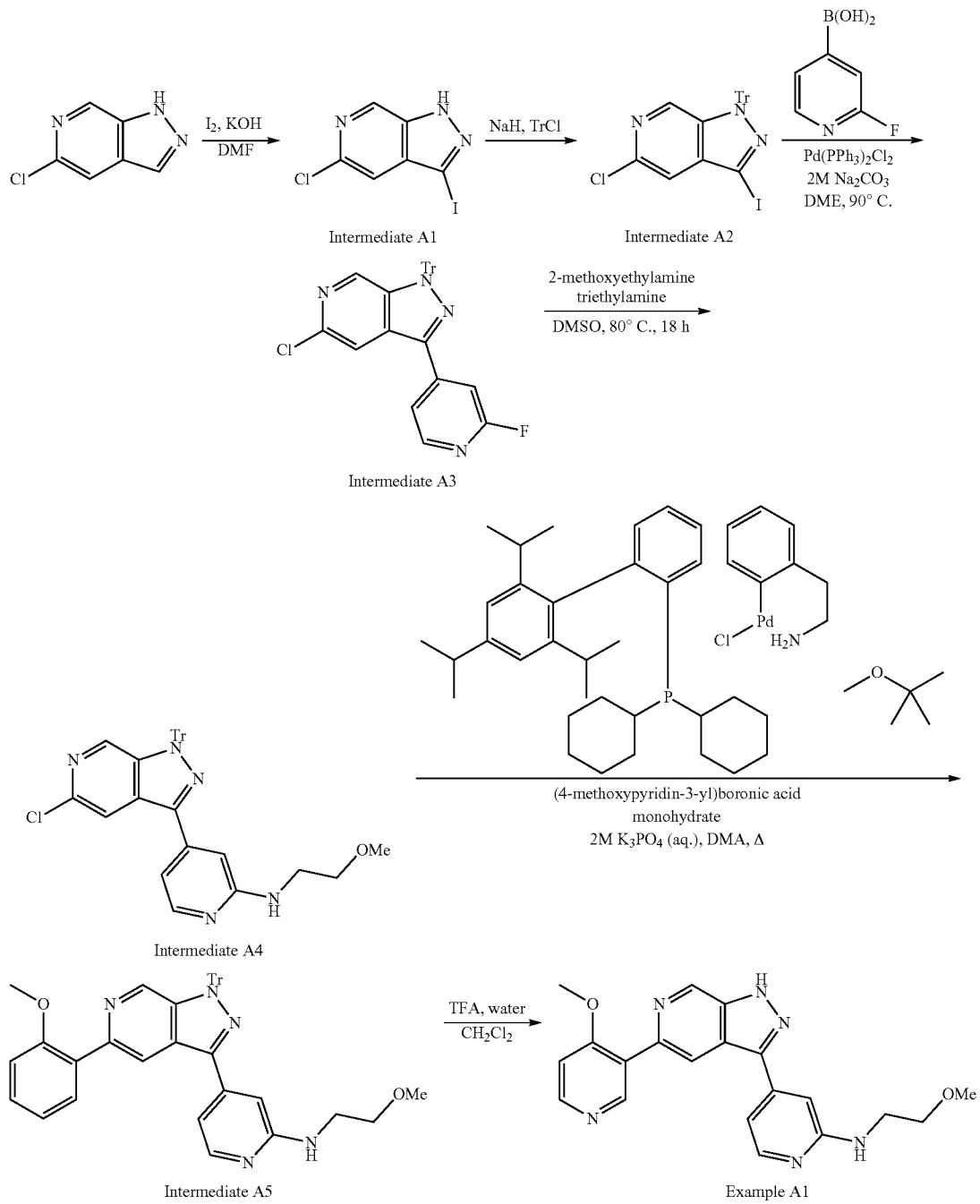

Scheme A

Step 1

A solution of the chloroazaindazole (16.1 g, 105 mmol) (prepared according to the method described in *J. Chem. Soc., Perkin Trans.* 1, 1980, 2398-2404. DOI: 10.1039/P19800002398) in DMF (200 mL) was treated with potassium hydroxide (14.71 g, 262 mmol) followed by iodine (27.1 g, 107 mmol) and was stirred at room temp for 1.5 h. An additional amount of iodine (1.45 g) was added and the reaction was stirred for additional 1 h. The excess iodine was quenched with 10% aqueous sodium thiosulfate. The resulting mixture was diluted with 1.2 L water. Aqueous 1N HCl was added until pH 4 was reached (a viscous white precipitate formed). The off-white solid was collected by filtration and washed with water. The material was dried overnight under vacuum at room temperature. The material was still wet in the morning. The material was slurried in methanol, transferred to a 1 L round bottom flask and concentrated. The resulting off-white solid was put under vacuum. NMR showed DMF and water present. Methylene chloride (200 mL), methanol (20 mL) and MeCN (300 mL) were added to the solid and the slurry was sonicated. The resulting tan solid was collected by filtration and washed with methylene chloride and dried to afford Intermediate A1.

Step 2

To a solution of Intermediate A1 (8 g, 28.6 mmol) in THF (66.6 mL) at 0° C. was added sodium hydride (1.603 g, 40.1 mmol). The resulting mixture was stirred for 10 min. Trityl chloride (9.58 g, 34.4 mmol) was added and the reaction was stirred at 0° C., allowing to warm to r.t. overnight. Water was added slowly to quench the reaction. The mixture was partitioned between EtOAc and water. The aqueous layer was discarded and the organic layer was washed with brine, dried over anhydrous sodium sulfate, filtered and evaporated. During evaporation, at ~⅕ the starting volume, a large amount of white solid precipitated, which was collected via filtration, washed with cold EtOAc and hexanes, and dried on the filter to afford Intermediate A2.

Step 3

Bis(triphenylphosphine)palladium(II)chloride (0.371 g, 0.529 mmol) was added to a stirred mixture of Intermediate A2 (2.76 g, 5.29 mmol), (2-fluoropyridin-4-yl)boronic acid (0.894 g, 6.35 mmol) and 2M Na$_2$CO$_3$ (aq.) (7.93 ml, 15.87 mmol) in DME (17.63 ml) that was previously purged with nitrogen for 5 minutes. The resulting mixture was the stirred at 90° C. for 18 h. The mixture was then cooled to room temperature. Water (100 mL) was added and the mixture was extracted with ethyl acetate (2×100 mL). The combined organic extracts were washed with brine (1×100 mL), dried (anhydrous Na$_2$SO$_4$), filtered and evaporated under reduced pressure. The resulting residue was purified by column chromatography on silica gel (330 g ISCO RediSep Rf column, gradient elution 0% EtOAc in hexanes to 50% EtOAc in hexanes) to give Intermediate A3.

Step 4

A solution of Intermediate A3 (730 mg, 1.49 mmol) in DMSO (7.4 mL) was treated with 2-methoxyethyl amine (1.28 mL, 14.87 mmol) and triethylamine (2.1 mL, 14.87 mmol), and sealed in a microwave tube. The resulting mixture was heated in an oil bath at 80° C. for 18 h. The mixture was then cooled to room temperature, unsealed and partitioned between EtOAc (75 mL) and water. The aqueous layer was discarded and the organic layer was washed with water, dried over anhydrous MgSO$_4$, filtered, and concentrated to afford a crude residue. The residue was purified by column chromatography on silica gel (ISCO RediSep 40 g silica gel column, gradient elution, 0% to 75% EtOAc in hexanes) to give Intermediate A4.

Step 5

Aqueous 2M potassium phosphate tribasic (604 μl, 1.209 mmol, purged with nitrogen prior) was added to a nitrogen purged, stirred, mixture of Intermediate A4 (330 mg, 0.604 mmol), (4-methoxypyridin-3-yl)boronic acid, monohydrate (207 mg, 1.209 mmol) and chloro(2-dicyclohexylphosphino-2',4',6'-tri-i-propyl-1,1'-biphenyl)[2-(2-aminoethyl)phenyl]palladium(II)methyl-t-butyl ether adduct (50.0 mg, 0.060 mmol) in DMA (10 mL) in a Biotage microwave tube. The vessel was sealed and heated in a Biotage microwave at 100° C., high absorption for 1 hour. The reaction was cooled and the vial was unsealed. Chloro(2-dicyclohexylphosphino-2',4',6'-tri-i-propyl-1,1'-biphenyl)[2-(2-aminoethyl)phenyl]palladium(II)methyl-t-butyl ether adduct (100 mg, 0.121 mmol), 2M potassium phosphate tribasic (aq.) (1.5 mL, 3.00 mmol), DME (10 mL) and water (10 mL) were added to the reaction. The mixture was sonicated in a bath sonicator, sealed then heated overnight in an 80° C. oil bath. The reaction was cooled to room temperature and unsealed. Brine was added to the reaction mixture and the solution was extracted with ethyl acetate (2×). The combined organic layers were dried (anhydrous Na$_2$SO$_4$), filtered and evaporated under reduced pressure. The resulting residue was purified by column chromatography on silica gel (ISCO RediSep Rf 40 g silica gel column, gradient elution with 0% to 100% EtOAc in hexanes) to afford Intermediate A5.

Step 6

Trifluoroacetic acid (5 ml, 64.9 mmol) was added to a stirred, room temperature mixture of Intermediate A5 (150 mg, 0.242 mmol) in water (4.5 ml, 250 mmol) and CH$_2$Cl$_2$ (5 ml) and the mixture was stirred at room temperature for 18 h. The reaction was concentrated to afford a residue which was dissolved in MeOH/DMSO and was purified by reversed-phase column chromatography (Analogix 100 g SF25 C18 column, gradient elution with 0% to 100% Acetonitrile/Water+0.1% TFA) to give Example A1 as a TFA salt.

TABLE A2

Utilizing a method similar to that outlined in Step 1 of Scheme A and the appropriate azaindazole starting material, the following Intermediates were prepared:

| Starting Azaindazole | Intermediate Number | Structure |
|---|---|---|
| 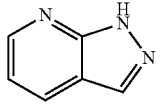 | Intermediate A2.1 | 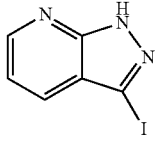 |
| 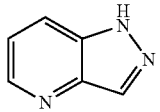 | Intermediate A2.2 | 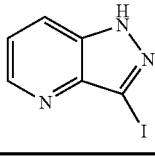 |

Scheme B

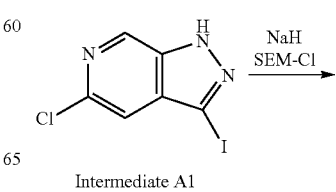

Intermediate A1

-continued

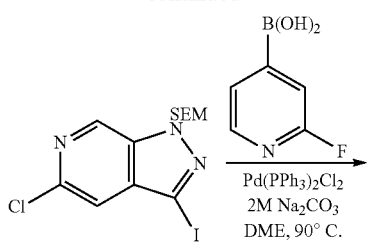

Intermediate B1

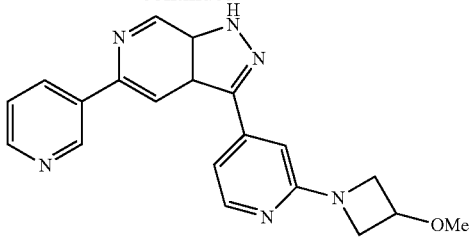

Example B1

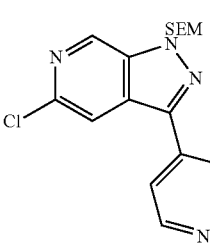

Intermediate B2a

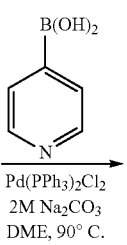

Intermediate B2b

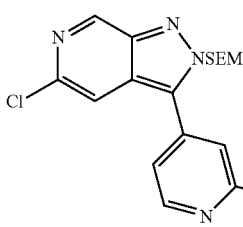

Intermediate B3

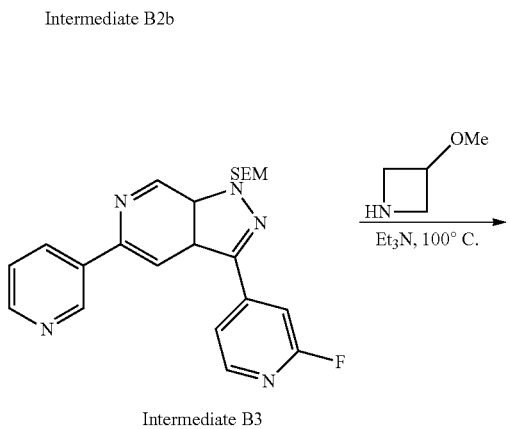

Intermediate B4

Step 1

To a solution of Intermediate A1 (11.69 g, 41.8 mmol) in THF (97 ml) at 0° C. was added sodium hydride (2.342 g, 58.6 mmol). The resulting mixture was stirred for 10 min. To this mixture was added SEM-Cl (8.14 ml, 46.0 mmol) and the reaction was stirred at 0° C., allowing to warm to r.t. overnight. Water was added slowly to quench the reaction. The mixture was partitioned between EtOAc and water. The aqueous layer was discarded and the organic layer was washed with brine, dried over anhydrous sodium sulfate, filtered and evaporated. The crude residue was slurried in EtOAc and hexanes, sonicated and filtered to afford Intermediate B1.

Step 2

Aqueous 2M $Na_2CO_3$ (19.22 ml, 38.4 mmol) was added to a stirred mixture of Intermediate B1 (5.25 g, 12.81 mmol) and (2-fluoropyridin-4-yl)boronic acid (2.167 g, 15.38 mmol) in DME (42.7 ml) and the mixture was stirred at room temperature for 5 min while bubbling nitrogen through the mixture. Bis(triphenylphosphine)palladium(II) chloride (0.899 g, 1.281 mmol) was added and the reaction was heated in a 90° C. oil bath for 5 hours under nitrogen. The mixture was cooled to room temperature and stirred overnight. Water (100 mL) was added and the mixture was extracted with ethyl acetate (2×100 mL). The combined organic layers were washed with brine (1×100 mL), dried (anhydrous $Na_2SO_4$), filtered and the solvent was evaporated under reduced pressure. The resulting residue was purified by column chromatography on silica gel (ISCO RediSep Rf, 330 g, gradient elution, 0% EtOAc in hexanes to 70% EtOAc in hexanes) to give Intermediates B2a and B2b.

Step 3

A solution of Intermediate B2a (156 mg, 0.412 mmol) in DME (2.5 mL) was treated with pyridine-3-boronic acid (63 mg, 0.515 mmol), aqueous 2M sodium carbonate solution (1.2 mL, 2.40 mmol), and bis(triphenylphosphine)palladium dichloride (29 mg, 0.041 mmol) and purged with nitrogen. The resulting mixture was heated overnight at 85° C. A second portion of bis(triphenylphosphine)palladium dichloride (58 mg, 0.082 mmol, 0.2 equiv) and pyridine-3-boronic acid (51 mg, 0.412 mmol, 1.0 equiv) were added and the reaction was heated at 85° C. overnight. The reaction was cooled to room temperature, diluted with saturated $NaHCO_3$, and extracted with EtOAc (3×-20 mL). The combined organic extracts were dried over anhydrous $MgSO_4$, filtered and concentrated to afford a crude residue, which was purified by reversed phase column chromatography (Analogix 100 g SF25 C18 column, gradient elution with 0% to 100% Acetonitrile/Water+0.1% HCOOH) to give Intermediate B3.

Step 4

A solution of Intermediate B3 (100 mg, 0.24 mmol) in triethylamine (6 mL) in a microwave vial was treated with 3-methoxyazetidine hydrochloride (353 mg, 2.86 mmol). The vial was sealed and heated at 100° C. for 18 h. The reaction was then cooled to room temperature, unsealed, diluted with EtOAc (60 mL) and washed with water (2×). The organic layer was dried over anhydrous MgSO$_4$, filtered and concentrated to afford a crude residue which was purified by reversed phase column chromatography (Analogix 100 g SF25 C18 column, gradient elution with 0% to 100% Acetonitrile/Water+0.1% HCO$_2$H) to give Intermediate B4.

Step 5

A solution of Intermediate B4 (110 mg, 0.23 mmol) in EtOH (10 mL) was treated with 3M HCl (aq.) (10 mL) and heated overnight at 80° C. The reaction was then cooled to room temperature and concentrated in vacuo. The resulting residue was subjected to reversed-phase chromatography (Analogix 55 g SF25 C18 column, gradient elution with 0% to 100% Acetonitrile/Water+0.1% TFA) to afford Example B1.

TABLE B1

Utilizing the method outlined in Scheme B, and the appropriate boronic acid or boronate ester and amine, the following Examples were prepared:

| Ex | Structure | LCMS Cond. | RT (min) | m/z | IC$_{50}$ (nM) |
|---|---|---|---|---|---|
| B1.2 | 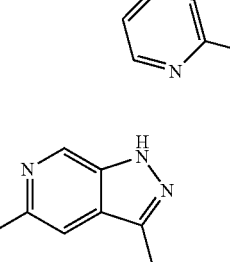 | A | 1.08 | 345 | 3.0 |
| B1.3 | 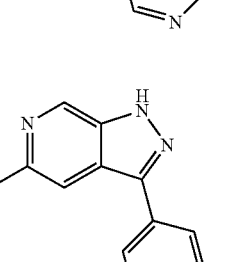 | A | 1.25 | 359 | 4.4 |
| B1.4 | 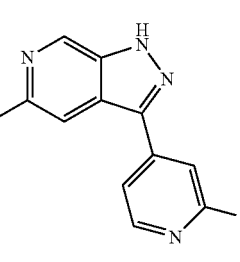 | A | 1.30 | 359 | 2.1 |
| B1.6 | 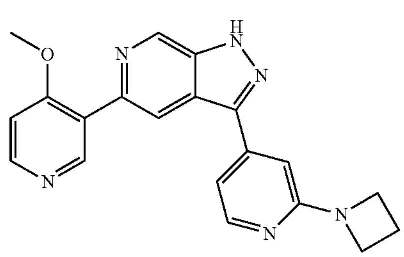 [SMILES: COc1ccncc1-c1cc2c(-c3ccnc(N4CCC4)c3)n[nH]c2cn1] | A | 1.47 | 359 | 0.65 |

TABLE B1-continued
Utilizing the method outlined in Scheme B, and the appropriate boronic acid or boronate ester and amine, the following Examples were prepared:
| Ex | Structure | Cond. | LCMS RT (min) | m/z | IC$_{50}$ (nM) |
|---|---|---|---|---|---|
| B1.7 | 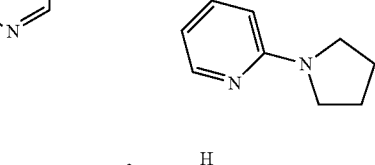 | A | 1.30 | 389 | 0.69 |
| B1.8 | 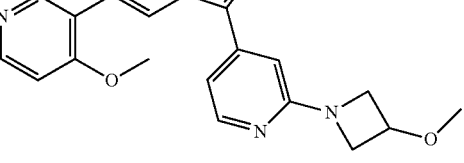 | A | 1.59 | 389 | 0.70 |
| B1.9 | 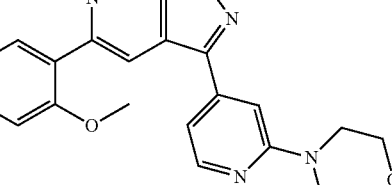 | A | 1.33 | 389 | <0.6 |
| B1.10 | 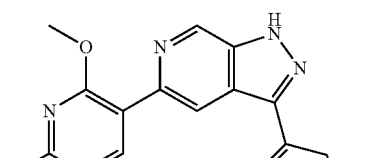 | A | 0.72 | 419 | 188.7 |
| B1.11 | 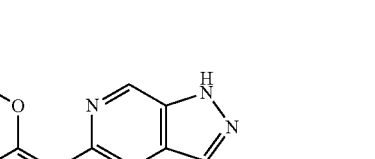 | A | 1.93 | 407 | 381.5 |

TABLE B1-continued

Utilizing the method outlined in Scheme B, and the appropriate boronic acid or boronate ester and amine, the following Examples were prepared:

| Ex | Structure | Cond. | LCMS RT (min) | m/z | IC$_{50}$ (nM) |
|---|---|---|---|---|---|
| B1.12 | 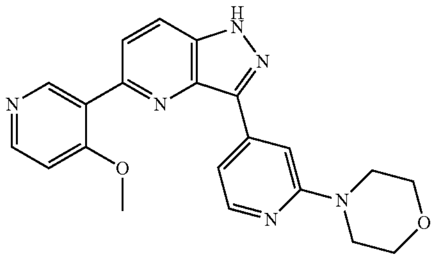 [SMILES: COc1ccncc1-c1ccc2[nH]nc(-c3ccnc(N4CCOCC4)c3)c2n1] | A | 1.681 | 389 | 2.505 |
| B1.13 | 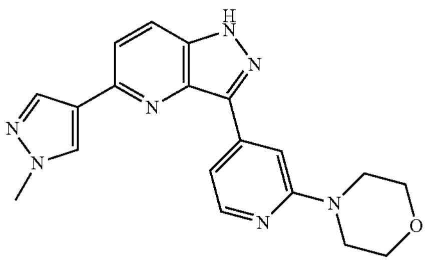 [SMILES: Cn1cc(-c2ccc3[nH]nc(-c4ccnc(N5CCOCC5)c4)c3n2)cn1] | A | 1.415 | 362 | 2.657 |

TABLE B2

Utilizing the method outlined in Scheme B, and the appropriate boronic acid or boronate ester in Step 3, the appropriate amine in Step 4, and formic acid as the additive instead of TFA for the reversed-phase chromatography performed in Step 5, the following Examples were prepared:

| Ex | Structure | Cond. | LCMS RT (min) | m/z | IC$_{50}$ (nM) |
|---|---|---|---|---|---|
| B2.1 | 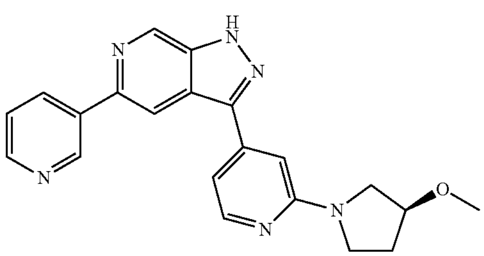 [SMILES: CO[C@H]1CCN(c2cc(-c3n[nH]c4cnc(-c5cccnc5)cc34)ccn2)C1] | A | 1.69 | 373 | 1.2 |
| B2.2 | 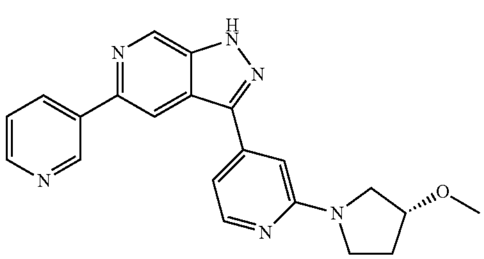 [SMILES: CO[C@@H]1CCN(c2cc(-c3n[nH]c4cnc(-c5cccnc5)cc34)ccn2)C1] | A | 1.69 | 373 | 1.2 |

TABLE B3

Utilizing the method outlined in Scheme B, Step 5 and Intermediate AA1 in place of Intermediate B4, the following Example was prepared:

| | | | LCMS | | |
|---|---|---|---|---|---|
| Ex | Structure | Cond. | RT (min) | m/z | IC$_{50}$ (nM) |
| B3.1 | | A | 1.87 | 340 | 7.2 |

TABLE B4

Utilizing a method similar to that outlined in Steps 1 and 2 of Scheme B and the appropriate starting material, the following intermediates were prepared:

| Starting Material | Intermediate Product Number | Intermediate Product Structure |
|---|---|---|
| Intermediate A2.1 | Intermediate B4.1 | |
| Intermediate A2.2 | Intermediate B4.2 | |

Scheme C

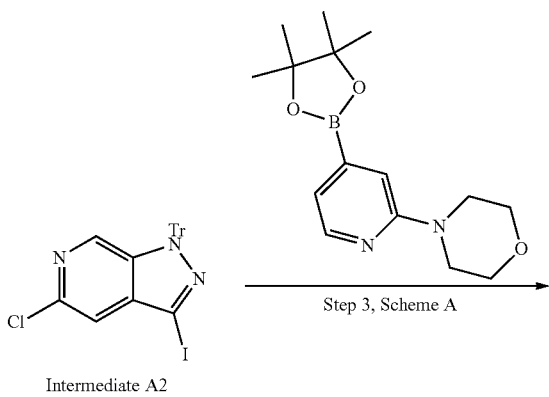

Intermediate A2

-continued

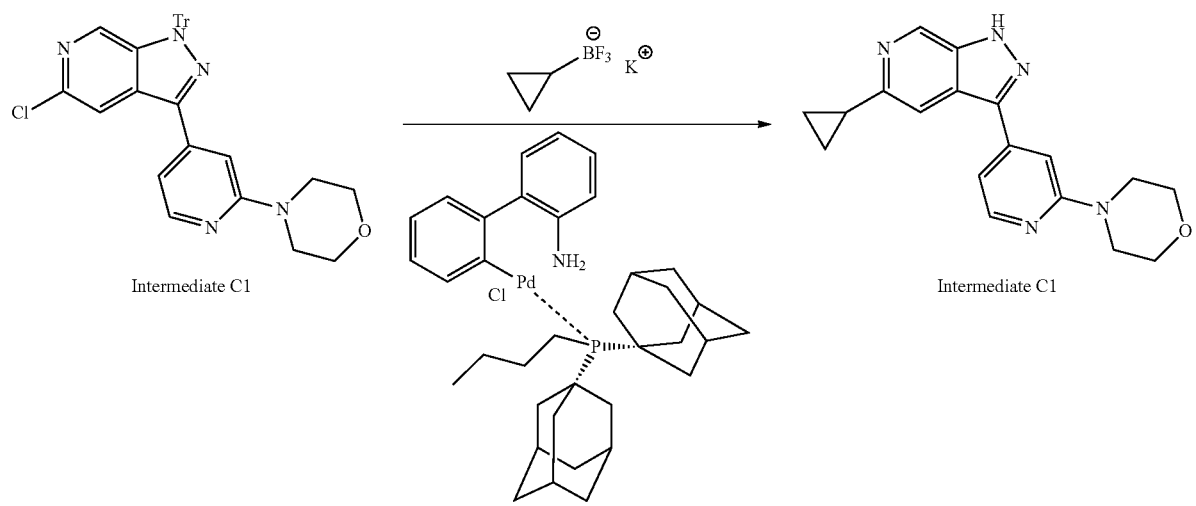

Step 1

Utilizing the method outlined in Step 3, Scheme A and substituting (2-fluoropyridin-4-yl)boronic acid with 4-(4-(4,4,5,5-tetramethyl-1,3,2-dioxaborolan-2-yl)pyridin-2-yl)morpholine, Intermediate C1 was prepared from Intermediate A2.

Step 2

A solution of Intermediate C1 (360 mg, 0.65 mmol) in dioxane (6.5 mL) was treated with cyclopropyl trifluoroborate, potassium salt (190 mg, 1.29 mmol), 1.5 M $Cs_2CO_3$ (aq.) (1.3 mL, 1.94 mmol) and purged with nitrogen for 10 to 15 minutes. To this mixture was added (2'-amino-[1,1'-biphenyl]-2-yl)palladium(II) chloride, di((3S,5S,7S)-adamantan-1-yl)(butyl)phosphine complex (1:1) (43 mg, 0.065 mmol) the mixture was sealed in a microwave vial and heated in a 100° C. oil bath for 18 h. The reaction was cooled and unsealed and (2'-amino-[1,1'-biphenyl]-2-yl)palladium (II) chloride, di((3S,5S,7S)-adamantan-1-yl)(butyl)phosphine complex (1:1) (43 mg, 0.065 mmol), cyclopropylboronic acid pinacol ester (217 mg, 1.29 mmol), and 1.5M $Cs_2CO_3$ (aq.) (1.3 mL, 1.94 mmol) were added. The reaction was sealed and stirred in a 120° C. oil bath for 3 hrs. The reaction was cooled to room temperature, unsealed, diluted with EtOAc (75 mL), washed with water (2×) and brine (1×). The organic layer was dried over anhydrous $MgSO_4$, filtered, and concentrated to afford a crude residue. The residue was purified by column chromatography on silica gel (ISCO RediSep 40 g silica gel column, gradient elution with 0% to 100% EtOAc in hexanes) to give the desired product with significant impurities present. The material was then subjected to reversed-phase column chromatography (Analogix C18 column, gradient elution with 0% to 100% MeCN in water with 0.1% TFA). The fractions corresponding to product sat in solution for 2 weeks. The solvent was evaporated to afford the Example C1 with significant impurities. The residue was purified again by reversed-phase column chromatography (Analogix C18, gradient elution with 0% to 100% MeCN in water with 0.1% TFA) to give Example C1 as an off-white solid.

TABLE C1

Utilizing the method outlined in Scheme C, and the appropriate boronic acid, boronic ester or potassium trifluoroborate salt, the following Examples were prepared:

| | | | LCMS | | |
|---|---|---|---|---|---|
| Ex | Structure | Cond. | RT (min) | m/z | $IC_{50}$ (nM) |
| C1 | | A | 1.62 | 322 | 53 |

Scheme D

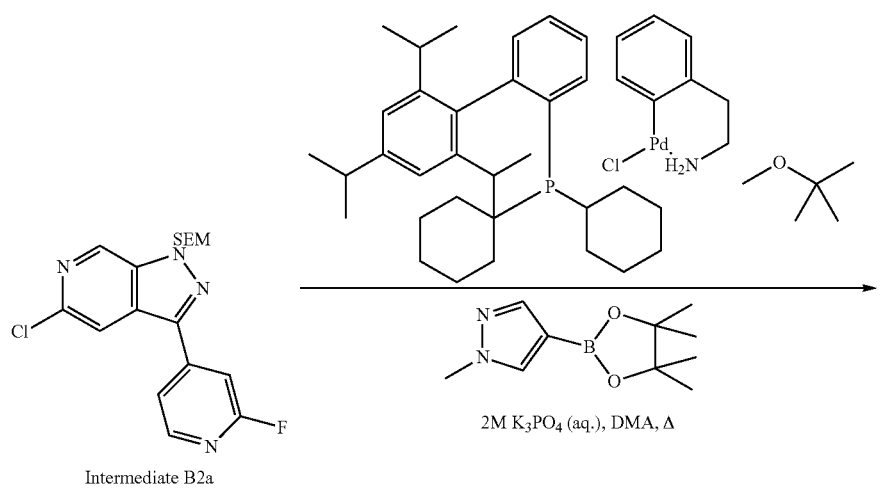

Intermediate B2a

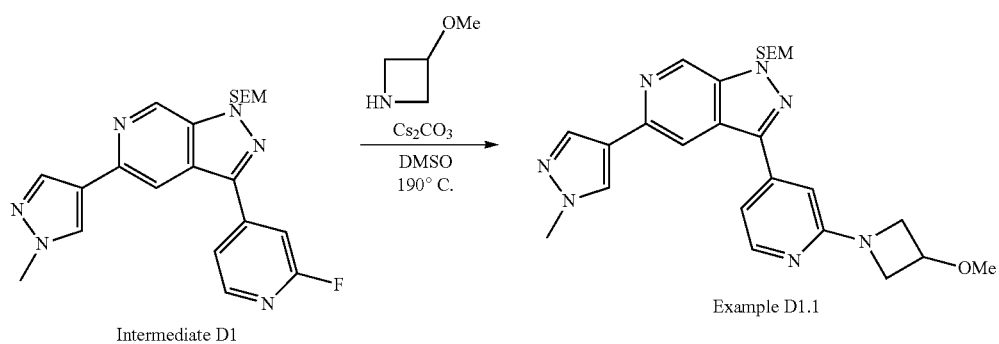

Intermediate D1

Example D1.1

Step 1

To a degassed solution of Intermediate B2a (380 mg, 1.003 mmol), 1-methyl-4-(4,4,5,5-tetramethyl-1,3,2-dioxaborolan-2-yl)-1H-pyrazole (417 mg, 2.006 mmol) and chloro(2-dicyclohexylphosphino-2',4',6'-tri-i-propyl-1,1'-biphenyl)[2-(2-aminoethyl)phenyl]palladium(II) methyl-t-butyl ether adduct (83 mg, 0.100 mmol) in DMA (5 mL) at rt, was added degassed aqueous 2M potassium phosphate tribasic (1000 μl, 2.01 mmol. The reaction was capped and heated at 80° C. overnight. The reaction was then cooled to RT and partitioned between EtOAc and water. The layers were separated and the organic layer was concentrated. The resulting residue was purified via silica gel chromatography [ISCO, 0-10% MeOH (with 2N $NH_3$) in DCM] which furnished Intermediate D1.

Step 2

A solution of Intermediate D1 (50 mg, 0.118 mmol), cesium carbonate (269 mg, 0.824 mmol), and 3-methoxyazetidine (41.0 mg, 0.471 mmol) in DMSO (1 mL) were sealed in a microwave tube. The reaction was heated in a Biotage microwave at 190° C. for 4 h. The reaction was then cooled down, unsealed and partitioned between EtOAc and water. The layers were separated and the organic layer was concentrated. The resulting residue was purified via silica gel chromatography [ISCO, 0-10% MeOH (2N NH3) in DCM] to afford Example D1.1.

TABLE D1

Utilizing the method outlined in Scheme D, the appropriate boronic acid, boronate ester or potassium trifluoroborate salt in Step 1, and the appropriate amine in Step 2, the following Examples were prepared:

| Ex | Structure | Cond. | LCMS RT (min) | m/z | IC$_{50}$ (nM) |
|---|---|---|---|---|---|
| D1.1 | 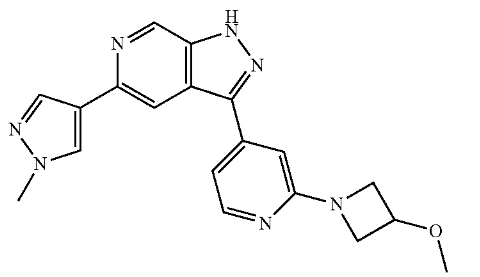 [SMILES: COC1CN(c2cc(-c3n[nH]c4cnc(-c5cnn(C)c5)cc34)ccn2)C1] | A | 1.306 | 362 | 1.04 |
| D1.2 | 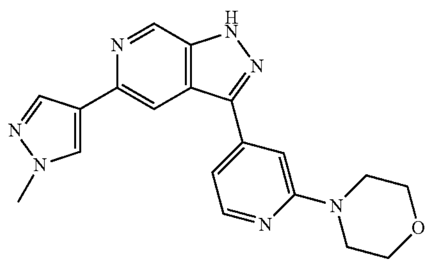 [SMILES: Cn1cc(-c2cc3c(-c4ccnc(N5CCOCC5)c4)n[nH]c3cn2)cn1] | A | 1.66 | 362 | <0.6 |
| D1.3 | 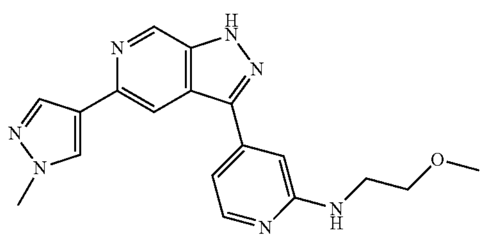 [SMILES: COCCNc1cc(-c2n[nH]c3cnc(-c4cnn(C)c4)cc23)ccn1] | A | 1.69 | 350 | 2.346 |

TABLE D2

Utilizing the method outlined in Scheme D, Step 2, with the appropriate amine and pyridine in place of DMSO the following Examples were prepared:

| Ex | Structure | Cond. | LCMS RT (min) | m/z | IC$_{50}$ (nM) |
|---|---|---|---|---|---|
| D2.1 | 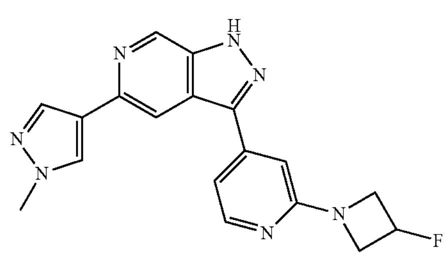 [SMILES: Cn1cc(-c2cc3c(-c4ccnc(N5CC(F)C5)c4)n[nH]c3cn2)cn1] | A | 1.67 | 350 | 3.8 |

Scheme E

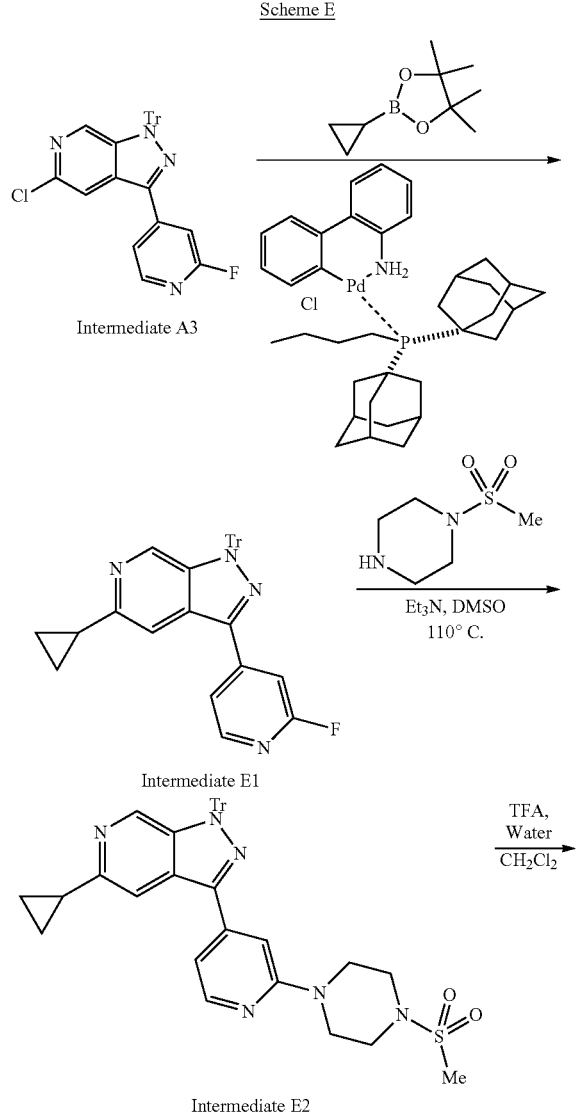

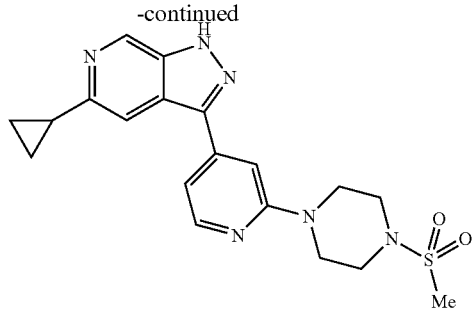

Example E1

Step 1

A solution of Intermediate A3 (4.02 g, 8.2 mmol) in 1,4-dioxane (82 ml) in a glass vessel was treated with cyclopropyl boronic acid pinacol ester (2.75 g, 16.4 mmol), 1.5 M $Cs_2CO_3$ (16.4 mL, 24.6 mmol) and purged with nitrogen for 10 to 15 minutes. To this mixture was added (2'-amino-[1,1'-biphenyl]-2-yl)palladium(II) chloride, di((3S,5S,7S)-adamantan-1-yl)(butyl)phosphine complex (1:1) (547 mg, 0.82 mmol). The glass vessel was sealed and the reaction was heated in an oil bath at 100° C. overnight. The reaction was cooled and uncapped. To the reaction was added (2'-amino-[1,1'-biphenyl]-2-yl)palladium(II) chloride, di((3S,5S,7S)-adamantan-1-yl)(butyl)phosphine complex (1:1) (547 mg, 0.82 mmol), cyclopropyl boronic acid (1.4 g, 2 eq), and 1.5M $Cs_2CO_3$ (aq.) (16.4 mL, 24.6 mmol). The reaction was resealed and immersed in a 120° C. oil bath with stirring for 3 hrs. The reaction was cooled to room temperature, unsealed, diluted with EtOAc (75 mL) and washed with water (2×) and brine (1×). The organic layer was dried over anhydrous $MgSO_4$, filtered, and concentrated to afford a crude residue which was purified via silica gel chromatography (gradient elution, 0% to 100% EtOAc in hexanes) to afford Intermediate E1.

Step 2

Intermediate E1 and methanesulfonamidopiperazine were combined and subjected to reaction conditions similar to those outlined in Scheme A, Step 4 to afford Intermediate E2.

Step 3

Intermediate E2 was subjected to conditions similar to those outlined in Scheme A, Step 6 to afford Example E1.

TABLE E1

Utilizing a method similar to that outlined in Scheme E and the requisite starting materials, the following Examples were prepared:

| Ex | Structure | LCMS Cond. | RT (min) | m/z | $IC_{50}$ (nM) |
|---|---|---|---|---|---|
| E2 | (structure) | A | 1.70 | 350 | 155 |

TABLE E1-continued

Utilizing a method similar to that outlined in Scheme E and the requisite starting materials, the following Examples were prepared:

| Ex | Structure | LCMS Cond. | RT (min) | m/z | IC$_{50}$ (nM) |
|---|---|---|---|---|---|
| E3 | 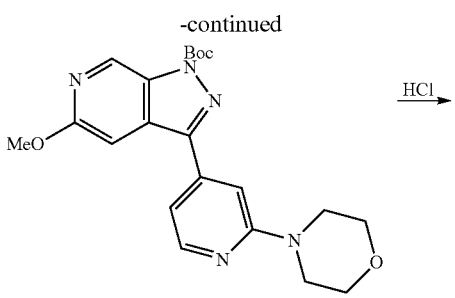 | A | 0.65 | 335 | 139 |

Scheme F

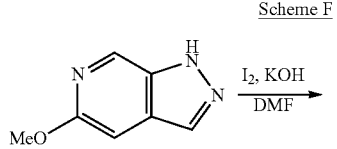

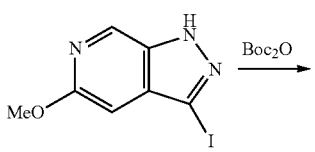

Intermediate F1

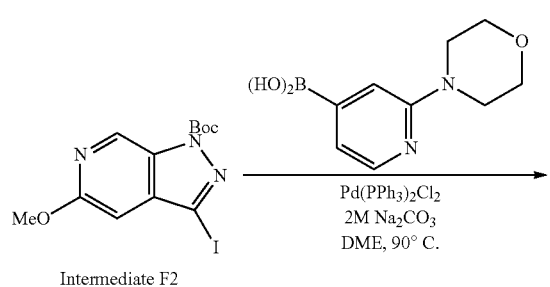

Intermediate F2

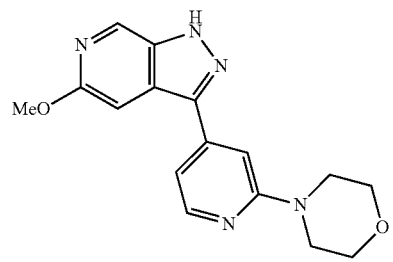

Intermediate F3

Example F1

Step 1

A solution of the 5-methoxyl-6-azaindazole (1.0 g, 6.7 mmol) in DMF (50 ml) was treated with potassium hydroxide (0.94 g, 16.8 mmol) followed by iodine (1.74 g, 6.84 mmol) and was stirred at room temp for 1.5 hrs. The excess iodine was quenched with 10% aqueous sodium thiosulfate. The resulting mixture was diluted with 1.2 L water. Aqueous 1N HCl was added until pH 4 was reached (a viscous white precipitate formed). The off-white solid was collected by filtration and washed with water. The material was dried overnight under vacuum at room temperature. The material was still wet in the morning. The material was slurried in methanol, transferred to a 1 L round bottom flask and concentrated. The resulting off-white solid was put under hivac. NMR showed DMF and water present. Methylene chloride (50 mL), methanol (10 mL) and MeCN (100 mL) were added to the solid and the slurry was sonicated. The resulting tan solid was collected by filtration and washed with methylene chloride and dried to afford pure Intermediate F1.

Step 2

To a solution of Intermediate F1 (922 mg, 3.35 mmol) in DCM/MeOH (20 ml, 1/1) at rt was added Boc$_2$O (1.097 g, 5.03 mmol), Et$_3$N (678 mg, 6.70 mmol), and DMAP (41 mg, 0.34 mmol). The resulting mixture was stirred for 2 h. Water was added slowly to quench the reaction. The mixture was partitioned between EtOAc and water. The combined organic layers was concentrated. The residue was purified via gradient C$_{18}$ chromatography [ISCO, 0-100% water (TFA) in acetonitrile (TFA)] which furnished the Intermediate F2.

Step 3

Pd(dppf)Cl$_2$ (0.098 g, 0.133 mmol) was added to a stirred mixture of Intermediate F2 (500 mg, 1.33 mmol), (2-morpholinepyridin-4-yl)boronic acid (0.416 g, 2.00 mmol) and Cs$_2$CO$_3$ (1.30 g, 4.00 mmol) in THF (5 ml) that was previously purged with nitrogen for 5 minutes. The resulting mixture was the stirred at 80° C. for 1.5 h. The mixture was then cooled to room temperature. Water (100 mL) was added and the mixture was extracted with ethyl acacate (2×100 mL). The combined organic extracts were washed with brine (1×100 mL), dried (anhydrous Na$_2$SO$_4$), filtered and evaporated under reduced pressure. The resulting residue was purified by column chromatography on silica gel (330 g ISCO RediSep Rf column, gradient elution 0% EtOAc in hexanes to 50% EtOAc in hexanes) to give Intermediate F3.

Step 4

A solution of Intermediate F3 (100 mg, 0.24 mmol) in MeOH (5.0 mL) was treated with HCl (5.0 mL, 4 N in dioxane). The resulting mixture was stirred at rt for 4 h. The reaction was concentrated. The residue was purified via gradient C$_{18}$ chromatography [ISCO, 0-100% water (TFA) in acetonitrile (TFA)] which furnished the Example F1.

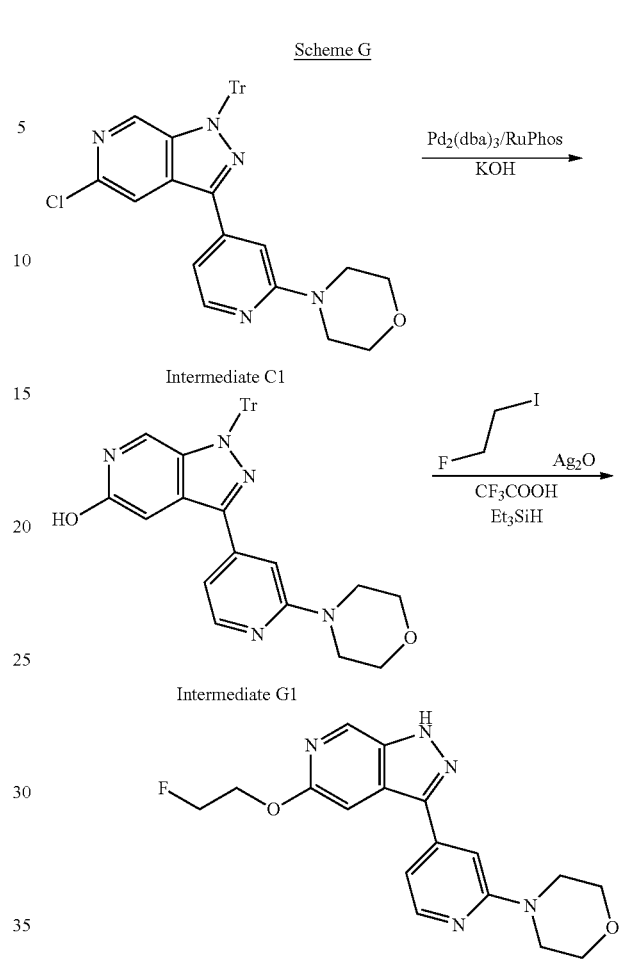

Scheme G

Intermediate C1

Intermediate G1

Example G1

Step 1

To a mixture of Intermediate C1 (100 mg, 0.179 mmol), Ruphos (16.72 mg, 0.036 mmol) Pd$_2$(dba)$_3$ (16.41 mg, 0.018 mmol) and KOH (40.2 mg, 0.717 mmol) was added 1,4-dioxane (4 mL) and H$_2$O (4 mL). The solution was degassed with N$_2$ for ca. 15 min. Then the reaction was sealed with a

TABLE F1

Utilizing the method outlined in Scheme F, the appropriate amine and the appropriate boronic acid, boronate ester or potassium trifluoroborate salt, the following Examples were prepared:

| Ex | Structure | Cond. | RT (min) | m/z | IC$_{50}$ (nM) |
|---|---|---|---|---|---|
| F2 | | A | 1.19 | 339 | 216.5 | cap and heated at 150° C. for 1 h, cooled to ambient temperature and neutralized with 1N HCl. After normal work-up, the residue was purified via gradient C18 chromatography [ISCO, 0-100% water (TFA) in acetonitrile (TFA)] which furnished Intermediate G1.

Step 2

In a microwave tube, added Intermediate G1 (60 mg, 0.111 mmol), 1-fluoro-2-iodoethane (193 mg, 1.112 mmol) and Ag$_2$O (61.3 mg, 0.222 mmol). The tube was sealed and heated on the hot plate at 150° C. for 15 min. After cooled to rt, the reaction was diluted with EtOAc and then filtered. The filtrate was concentrated. To the residue in a 20 mL vial, was added 2 mL of TFA, followed by 0.5 mL of Et$_3$SiH. The reaction was stirred at rt for 1 h. The reaction was then concentrated. The residue was purified via gradient C18 chromatography [ISCO, 0-100% water (with 0.1% TFA) in acetonitrile (with 0.1% TFA)] which furnished Example G1.

TABLE G1

Utilizing the method outlined in Scheme G, and the appropriate alkyl halide, the following Examples were prepared:

| Ex | Structure | Cond. | LCMS RT (min) | m/z | IC$_{50}$ (nM) |
|---|---|---|---|---|---|
| G1 | (structure) | A | 1.55 | 344 | 149 |
| G2 | (structure) | A | 1.89 | 338 | 104.2 |
| G3 | (structure) | A | 1.91 | 340 | 94.7 |
| G4 | (structure) | A | 1.99 | 362 | 185.5 |

TABLE G1-continued

Utilizing the method outlined in Scheme G, and the appropriate alkyl halide, the following Examples were prepared:

| Ex | Structure | LCMS Cond. | RT (min) | m/z | IC$_{50}$ (nM) |
|---|---|---|---|---|---|
| G5 | 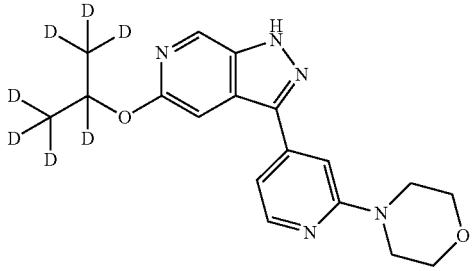 [SMILES: [2H]C([2H])([2H])C([2H])(Oc1cc2c(-c3ccnc(N4CCOCC4)c3)n[nH]c2cn1)C([2H])([2H])[2H]] | A | 1.90 | 347 | 26.7 |
| G6 | 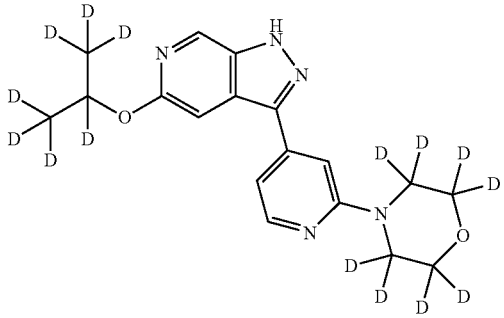 [SMILES: [2H]C([2H])([2H])C([2H])(Oc1cc2c(-c3ccnc(N4C([2H])([2H])C([2H])([2H])OC([2H])([2H])C4([2H])[2H])c3)n[nH]c2cn1)C([2H])([2H])[2H]] | A | 1.89 | 355 | 43.1 |

Scheme G2

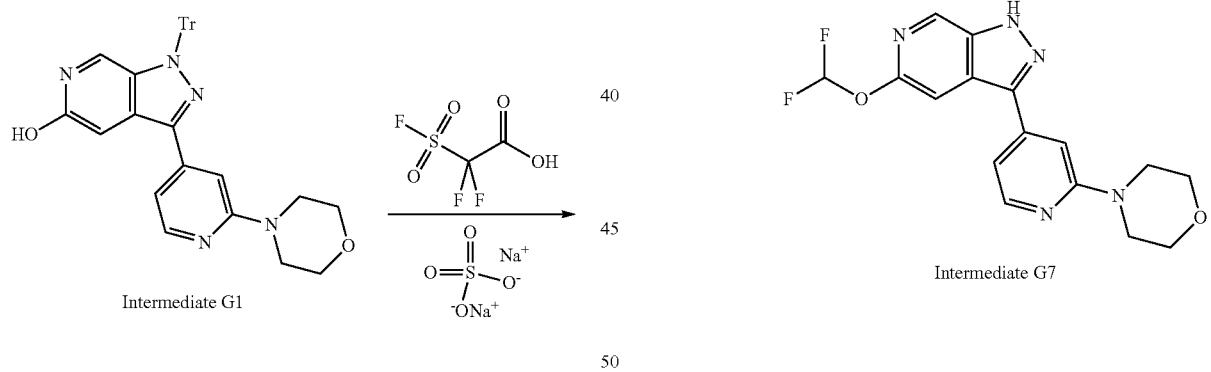

Intermediate G7

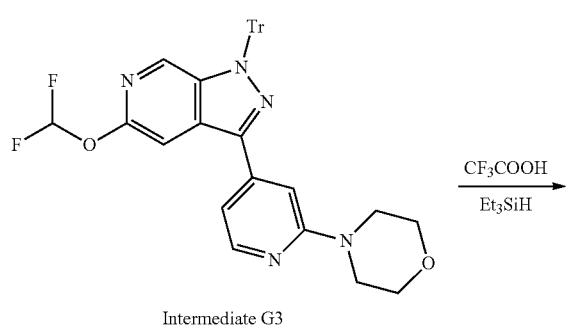

Intermediate G3

To a stirred solution of Intermediate G1 (55 mg, 0.102 mmol) in anhydrous acetonitrile (2 mL) were added 2-(fluorosulfonyl)difluoroacetic acid (0.016 ml, 0.153 mmol) and sodium sulfate (4.34 mg, 0.031 mmol) and the mixture was stirred at room temperature for 4.5 h under a nitrogen atmosphere. The reaction was quenched by addition of saturated aqueous NaHCO$_3$, and the mixture was extracted with ethyl acetate. The organic layer was washed with brine, dried over sodium sulfate, and concentrated. The residue was purified via silica gel chromatography [ISCO, 0-10% MeOH (2N NH$_3$) in DCM] which furnished Intermediate G3, which was treated with TFA/Et$_3$SiH according to Scheme G step 2 to afford Example G7.

TABLE G2

| Ex | Structure | LCMS Cond. | RT (min) | m/z | IC$_{50}$ (nM) |
|---|---|---|---|---|---|
| G7 | 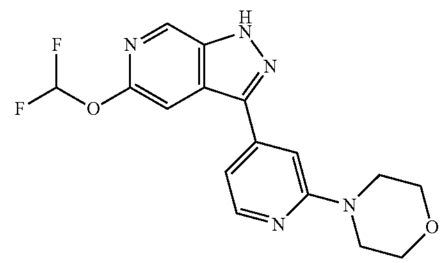 [SMILES: FC(F)Oc1cc2c(-c3ccnc(N4CCOCC4)c3)n[nH]c2cn1] | A | 2.08 | 348 | 49.0 |

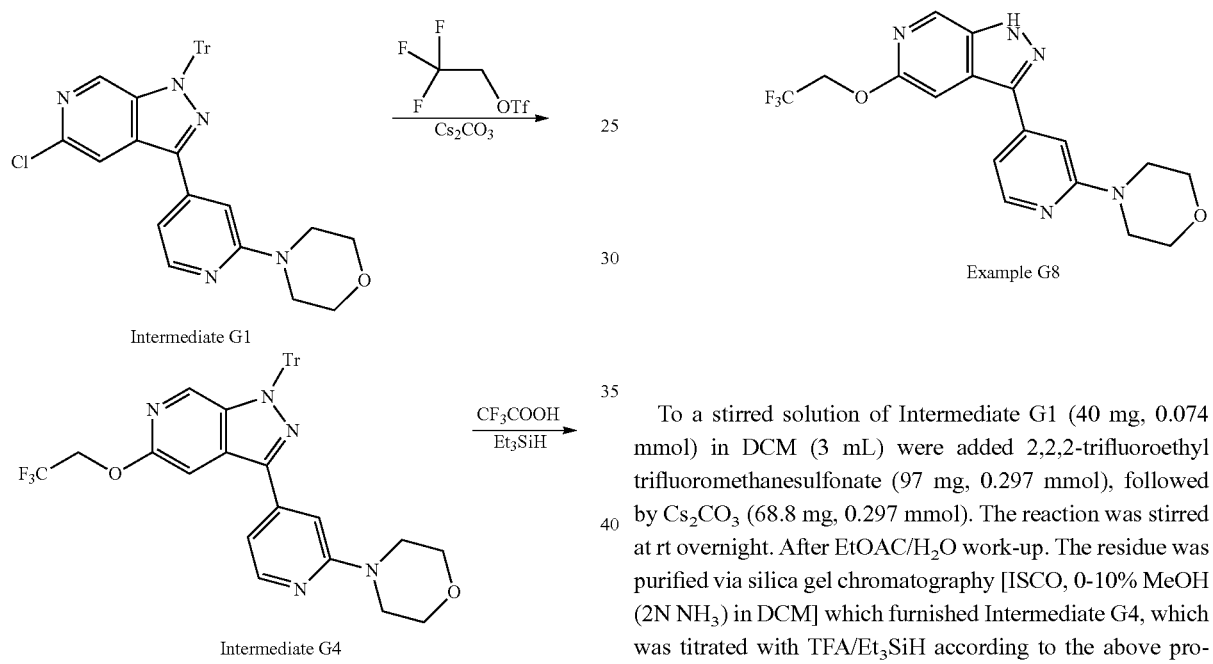

Scheme G3

Intermediate G1

Intermediate G4

Example G8

To a stirred solution of Intermediate G1 (40 mg, 0.074 mmol) in DCM (3 mL) were added 2,2,2-trifluoroethyl trifluoromethanesulfonate (97 mg, 0.297 mmol), followed by Cs$_2$CO$_3$ (68.8 mg, 0.297 mmol). The reaction was stirred at rt overnight. After EtOAC/H$_2$O work-up. The residue was purified via silica gel chromatography [ISCO, 0-10% MeOH (2N NH$_3$) in DCM] which furnished Intermediate G4, which was titrated with TFA/Et$_3$SiH according to the above procedure to afford Example G8.

TABLE G3

| Ex | Structure | LCMS Cond. | RT (min) | m/z | IC$_{50}$ (nM) |
|---|---|---|---|---|---|
| G8 | 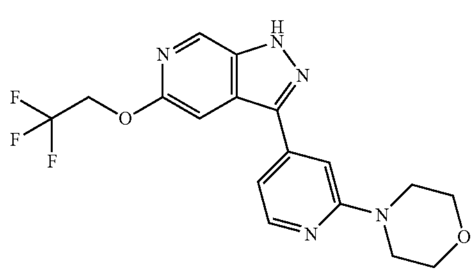 [SMILES: FC(F)(F)COc1cc2c(-c3ccnc(N4CCOCC4)c3)n[nH]c2cn1] | A | 1.98 | 380 | 433 |

Scheme H

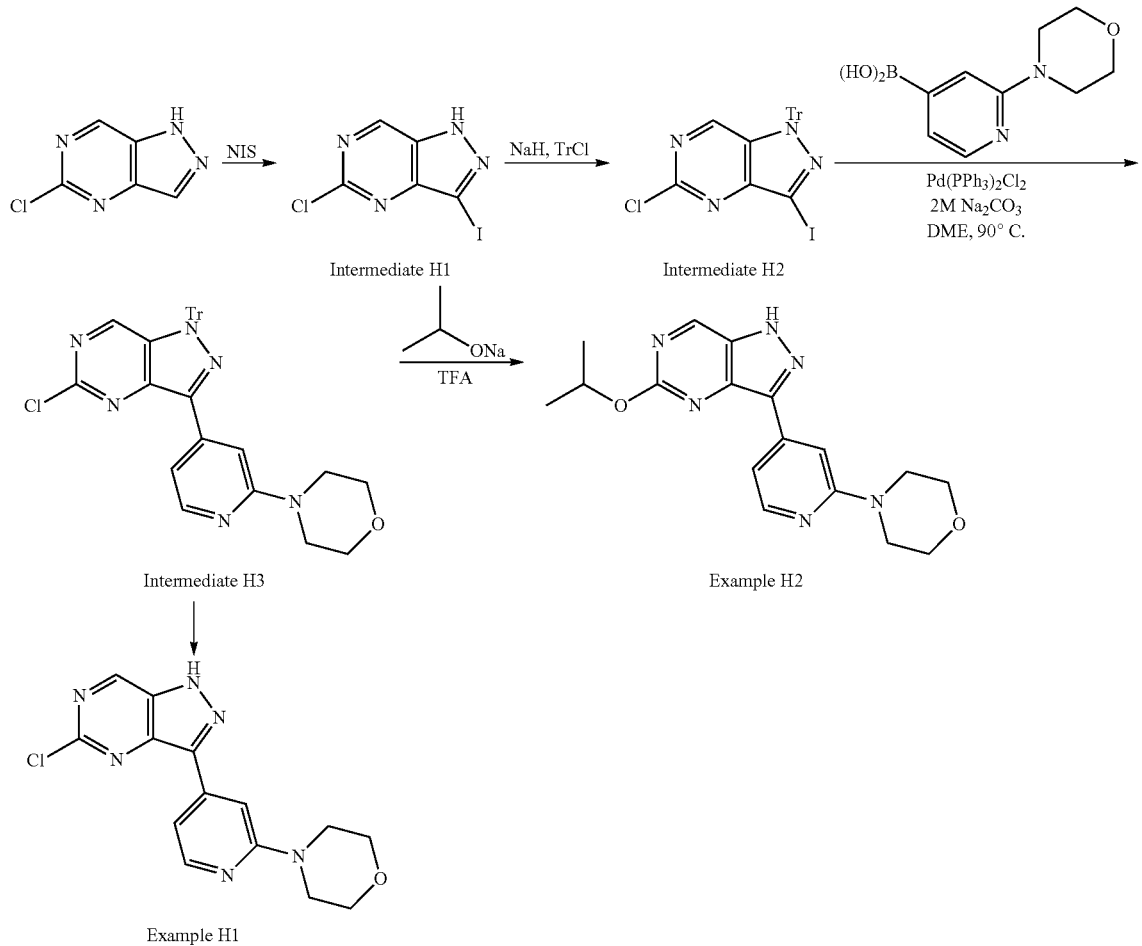

Step 1

A mixture of 5-chloro-1H-pyrazolo[4,3-d]pyrimidine (1 g, 6.47 mmol) and NIS (1.747 g, 7.76 mmol) in acetonitrile (6 mL) in a microwave sealed tube was heated to 120° C. for 40 min in an oil bath. Then the reaction was cooled down and concentrated to dryness. The residue was purified via gradient C18 chromatography [ISCO, 0-100% water (0.1% TFA) in acetonitrile (0.1% TFA)] which furnished Intermediate H1.

Step 2

To a solution of Intermediate H1 (1.8 g, 6.42 mmol) in THF (5 ml) at 0° C. was added sodium hydride (0.216 g, 8.99 mmol). The resulting mixture was stirred for 10 min. Trityl chloride (2.15 g, 7.70 mmol) was added and the reaction was stirred at 0° C., allowing to warm to r.t. overnight. Water was added slowly to quench the reaction. The mixture was partitioned between EtOAc and water. The aqueous layer was discarded and the organic layer was washed with brine, dried over anhydrous sodium sulfate, filtered and evaporated. During evaporation, at ~⅕ the starting volume, a large amount of white solid precipitated, which was collected via filtration, washed with cold EtOAc and hexanes, and dried on the filter to afford Intermediate H2.

Step 3

Bis(triphenylphosphine)palladium(II) chloride (0.111 g, 0.15 mmol) was added to a stirred mixture of Intermediate H2 (790 mg, 1.51 mmol), (2-morpholinepyridin-4-yl)boronic acid (0.314 g, 1.51 mmol) and $Cs_2CO_3$ (985 mg, 3.02 mmol) in THF (5 ml) that was previously purged with nitrogen for 5 minutes. The resulting mixture was then stirred at 90° C. for 18 h. The mixture was then cooled to room temperature. Water (20 mL) was added and the mixture was extracted with ethyl acetate (2×20 mL). The combined organic extracts were washed with brine (1×100 mL), dried (anhydrous $Na_2SO_4$), filtered and evaporated under reduced pressure. The resulting residue was purified by column chromatography on silica gel (80 g ISCO RediSep Rf column, gradient elution 0% EtOAc in hexanes to 50% EtOAc in hexanes) to give Intermediate H3. The Intermediate H3 was treated with TFA to afford Example H1.

Step 4

To a solution of Intermediate H3 (80 mg, 0.143 mmol) in THF (5 mL) at rt, was added sodium propan-2-olate (117 mg, 1.431 mmol). The reaction was stirred at rt for 30 min. Then the reaction was quenched with water and was extracted with ethyl acetate. The combined organic extracts were washed with brine (1×20 mL), dried (anhydrous $Na_2SO_4$), filtered and evaporated under reduced pressure. The residue was treated with TFA, and purified by column chromatography on silica gel (80 g ISCO RediSep Rf column, gradient elution 0% EtOAc in hexanes to 50% EtOAc in hexanes) to afford Example H2.

TABLE H1
| Ex | Structure | LCMS Cond. | RT (min) | m/z | IC$_{50}$ (nM) |
|---|---|---|---|---|---|
| H1 | 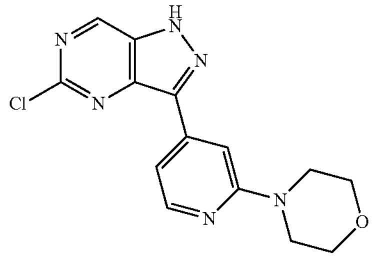 [SMILES: Clc1ncc2[nH]nc(-c3ccnc(N4CCOCC4)c3)c2n1] | A | 1.750 | 317 | 1397 |
| H2 | 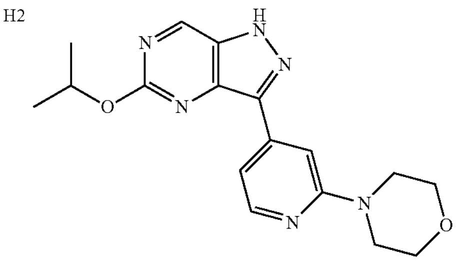 | A | 1.373 | 341 | 26.82 |
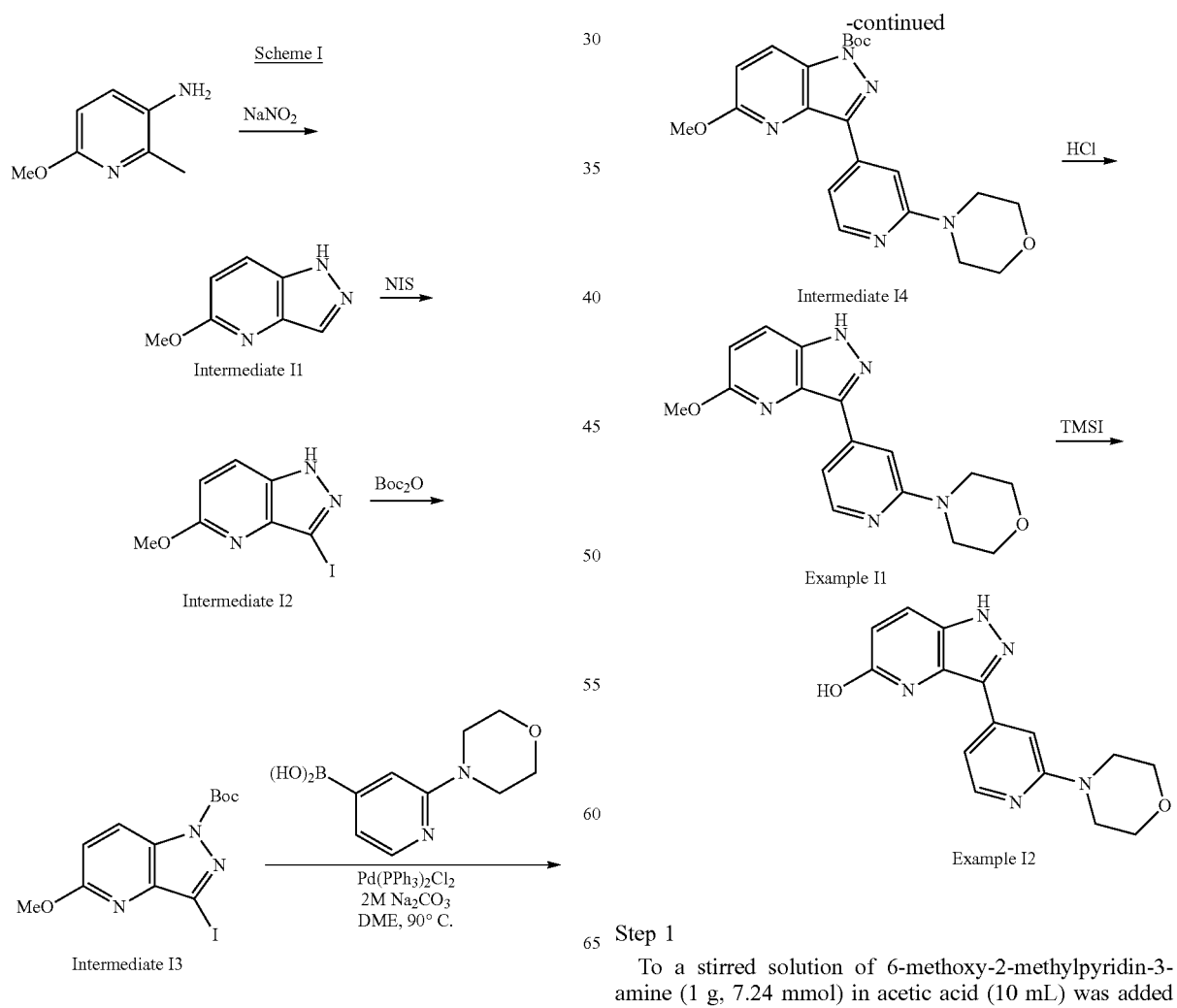
Step 1
To a stirred solution of 6-methoxy-2-methylpyridin-3-amine (1 g, 7.24 mmol) in acetic acid (10 mL) was added dropwise a solution of NaNO₂ (0.749 g, 10.86 mmol) in water (2 mL) at 0° C., and the reaction mixture was stirred at room temperature for 1 hour. residue was purified via gradient C18 chromatography [ISCO, 0-100% water (TFA) in acetonitrile (TFA)] which furnished Intermediate I1 as a light yellow foam.

Step 2

A mixture of Intermediate I1 (470 mg, 3.15 mmol) and NIS (851 mg, 3.78 mmol) in acetonitrile (5 mL) in a microwave sealed tube was heated to 120° C. for 20 min in microwave reactor. Then the reaction was cooled down and concentrated to dryness and provide crude Intermediate I2, which was used directly in the next step.

Step 3

The crude Intermediate I2 (867 mg, 3.15 mmol) was dissovled in DCM (8 mL) and MeOH (8 mL), followed by adding Boc₂O (1032 mg, 4.73 mmol), Et₃N (0.879 mL, 6.30 mmol), DMAP (38.5 mg, 0.315 mmol). The mixture was stirred at rt for 2 h. The reaction was concentrated, then dissolved in water, and extracted with EtOAc. The combined organic layers were concentrated. The residue was purified via silica gel chromatography [ISCO, 0-10% MeOH (2N NH₃) in DCM] which furnished Intermediate I3.

Step 4

Bis(triphenylphosphine)palladium(II) chloride (0.039 g, 0.053 mmol) was added to a stirred mixture of Intermediate I3 (200 mg, 0.533 mmol), (2-morpholinepyridin-4-yl)boronic acid (0.166 g, 0.80 mmol) and Cs₂CO₃ (521 mg, 1.60 mmol) in THF (8 ml) that was previously purged with nitrogen for 5 minutes. The resulting mixture was the stirred at 90° C. for 18 h. The mixture was then cooled to room temperature. Water (20 mL) was added and the mixture was extracted with ethyl acetate (2×20 mL). The combined organic extracts were washed with brine (1×100 mL), dried (anhydrous Na₂SO₄), filtered and evaporated under reduced pressure. The resulting residue was purified by column chromatography on silica gel (80 g ISCO RediSep Rf column, gradient elution 0% EtOAc in hexanes to 50% EtOAc in hexanes) to give Intermediate I4.

Step 5

To a solution of Intermediate I4 (50 mg, 0.122 mmol) in MeOH (2 mL) was added HCl (2 mL, 8.00 mmol, 4N in dioxane) at rt. The mixture was stirred at rt for 2 h and then concentrated. The residue was purified via gradient C18 chromatography [ISCO, 0-100% water (TFA) in acetonitrile (TFA)] which furnished Example I1.

Step 6

To a solution of Example I1 (100 mg, 0.243 mmol) in DCE (2 mL) and acetonitrile (2.000 mL) was added TMSI (0.1 mL, 0.700 mmol). The mixture was heated to 80° C. for 2 h. Then the reaction was cooled down and concentrated. The residue was purified via gradient C18 chromatography [ISCO, 0-100% water (0.1% TFA) in acetonitrile (0.1% TFA)] which furnished Example I2.

TABLE I1

| | | LCMS | | |
|---|---|---|---|---|
| Ex | Structure | Cond. | RT (min) | m/z | IC₅₀ (nM) |
| I1 | 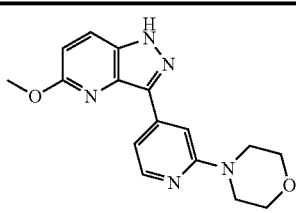 | A | 1.95 | 312 | 42.9 |

TABLE I1-continued

| | | LCMS | | |
|---|---|---|---|---|
| Ex | Structure | Cond. | RT (min) | m/z | IC₅₀ (nM) |
| I2 | 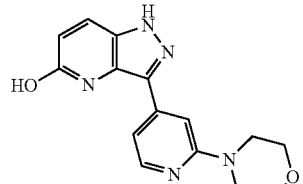 | A | 0.95 | 298 | 814 |

Scheme J

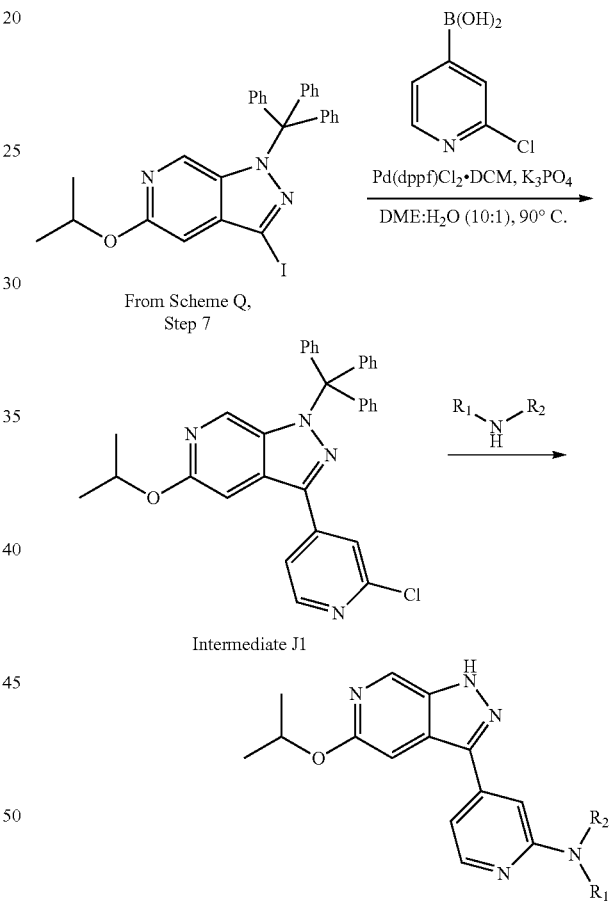

From Scheme Q, Step 7

Intermediate J1

Examples J1 to J43

Step 1

A stirred solution of the product from Step 7 of Scheme Q (5 g, 9.17 mmol), (2-chloropyridin-4-yl)boronic acid (1.875 g, 11.92 mmol) and potassium phosphate tribasic (5.84 g, 27.5 mmol) in 1,4-dioxane (100 ml) and Water (10 ml) was purged with argon for 15 min. Then 1,1'-bis(diphenylphosphino)ferrocene-palladium(II)dichloride dichloromethane complex (0.749 g, 0.917 mmol) was added and the mixture was heated at 100° C. for 16 h. The reaction was cooled to rt and concentrated under vacuum. To the residue were added water and DCM. The organic layer was separated and the aqueous layer was extracted with DCM (×3). The combined organic layers were dried, filtered and concentrated to leave a residue which was purified by silica gel column chromatography (elution with 5:1 hexane:EtOAc) to yield Intermediate J1.

Step 2

Parallel preparation of Examples J1-J43: To a set of 2 dram vials equipped with stir bars was added the requisite amine (0.13 mmol) solid followed by 1,3-bis(2,6-diisopropylphenyl)imidazolium chloride (5.6 mg, 0.013 mmol), Pd$_2$(dba)$_3$ (3 mg, 0.0033 mmol) and NaOt-Bu (25 mg, 0.26 mmol). The vials were then transferred into a glove bag under an atmosphere of nitrogen. At this time the requisite liquid amines (0.13 mmol) were added to the appropriate vials. To each vial was then added a solution of Intermediate J1 (35 mg, 0.066 mmol) in toluene (1 mL). The vials were then capped and removed from the glove bag and placed into a preheated aluminum block at 90° C. The mixtures were stirred at that temperature overnight. The vials were then allowed to cool to RT. To each vial was added DCM (2 mL) followed by water (1 mL). The organic layer was separated and filtered into a clean set of vials. The solvent was then removed under reduced pressure. To each crude residue was added DCM (1 mL), TFA (0.5 mL) and water (0.050 mL). The mixtures were shaken at RT for 2 hours. The solutions were then concentrated in vacuo. The crude residues were dissolved in DMSO (1 mL) and filtered. The crude products were purified by mass triggered HPLC using the following conditions: [Waters Sunfire C18 column, 5 μm, 30×100 mm, gradient 10-30% initial to a range of 45-75% final MeCN (0.1% formic acid) in water (0.1% formic acid) 50 mL/min, 8-10 min run time] to afford Examples J1-J43.

TABLE J

| Example | Structure | LCMS data m/z | Ret Time (min) | Cond. | LRRK2 IC$_{50}$ (nM) |
| --- | --- | --- | --- | --- | --- |
| J1 | 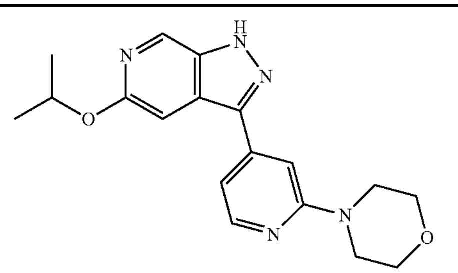 | 340 | 1.87 | A | 7.15 |
| J2 | 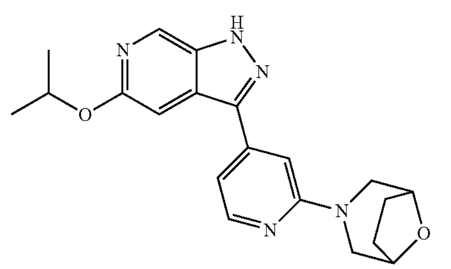 [SMILES: CC(C)Oc1cc2c(-c3ccnc(N4CC5CCC(C4)O5)c3)n[nH]c2cn1] | 366 | 1.96 | A | 64.0 |
| J3 | 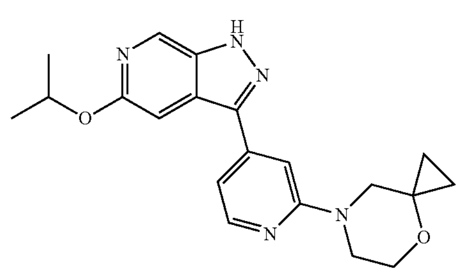 [SMILES: CC(C)Oc1cc2c(-c3ccnc(N4CCOC5(CC5)C4)c3)n[nH]c2cn1] | 366 | 1.89 | A | 11.9 |
| J4 | 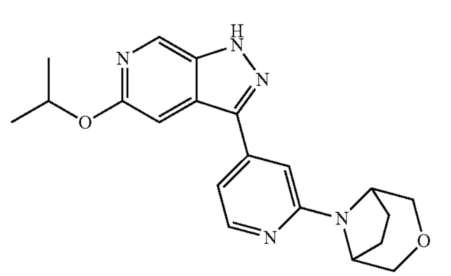 [SMILES: CC(C)Oc1cc2c(-c3ccnc(N4C5CCC4COC5)c3)n[nH]c2cn1] | 366 | 1.97 | A | 85.4 |

TABLE J-continued

| Example | Structure | LCMS data m/z | Ret Time (min) | Cond. | LRRK2 IC$_{50}$ (nM) |
|---|---|---|---|---|---|
| J5 | 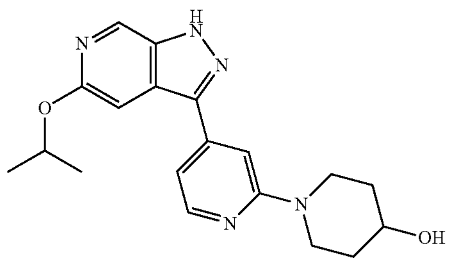 [SMILES: CC(C)Oc1cc2c(-c3ccnc(N4CCC(O)CC4)c3)n[nH]c2cn1] | 354.2 | 0.76 | D | 37 |
| J6 | 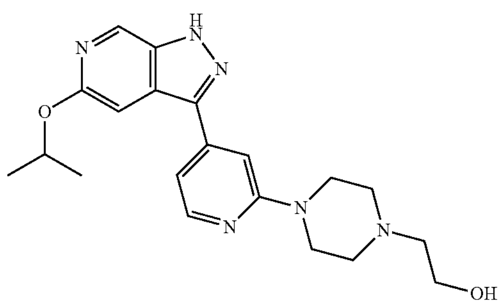 [SMILES: CC(C)Oc1cc2c(-c3ccnc(N4CCN(CCO)CC4)c3)n[nH]c2cn1] | 383.2 | 0.74 | D | 16 |
| J7 | 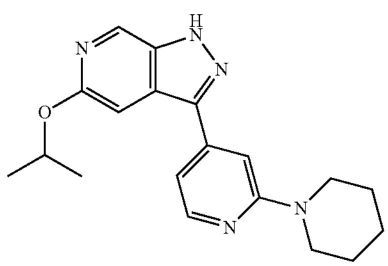 [SMILES: CC(C)Oc1cc2c(-c3ccnc(N4CCCCC4)c3)n[nH]c2cn1] | 338.2 | 1.10 | D | 45 |
| J8 | 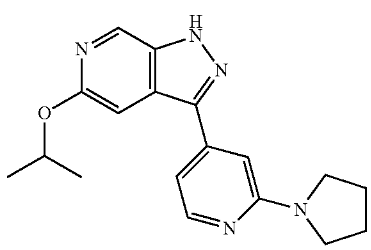 [SMILES: CC(C)Oc1cc2c(-c3ccnc(N4CCCC4)c3)n[nH]c2cn1] | 324.2 | 0.97 | D | 28 |
| J9 | 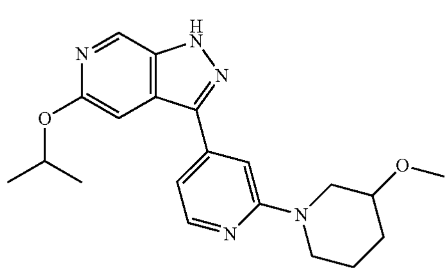 [SMILES: COC1CCCN(c2cc(-c3n[nH]c4cnc(OC(C)C)cc34)ccn2)C1] | 368.2 | 0.98 | D | 51 |

TABLE J-continued

| Example | Structure | LCMS data m/z | Ret Time (min) | Cond. | LRRK2 IC$_{50}$ (nM) |
|---|---|---|---|---|---|
| J10 | 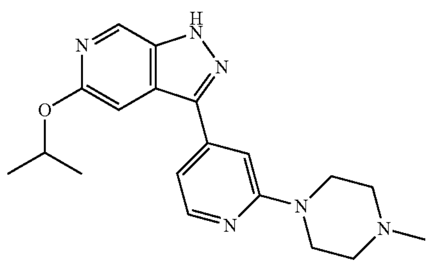 [SMILES: CC(C)Oc1cc2c(-c3ccnc(N4CCN(C)CC4)c3)n[nH]c2cn1] | 353.2 | 0.84 | D | 24 |
| J11 | 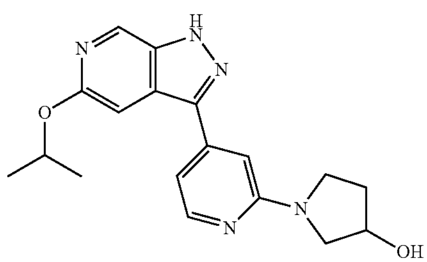 [SMILES: CC(C)Oc1cc2c(-c3ccnc(N4CCC(O)C4)c3)n[nH]c2cn1] | 340.2 | 0.72 | D | 31 |
| J12 | 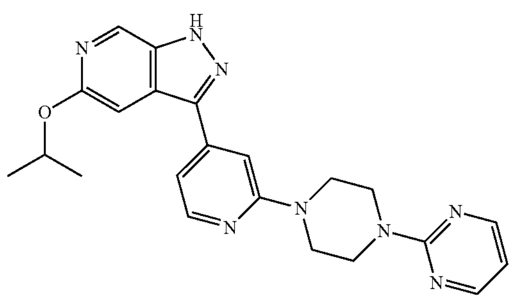 [SMILES: CC(C)Oc1cc2c(-c3ccnc(N4CCN(c5ncccn5)CC4)c3)n[nH]c2cn1] | 417.2 | 1.00 | D | 51 |
| J13 | 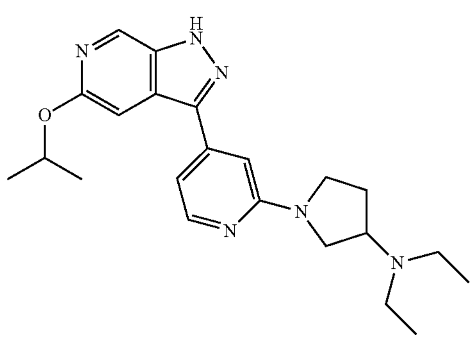 [SMILES: CCN(CC)C1CCN(c2cc(-c3n[nH]c4cnc(OC(C)C)cc34)ccn2)C1] | 395.3 | 1.01 | D | 29 |
| J14 | 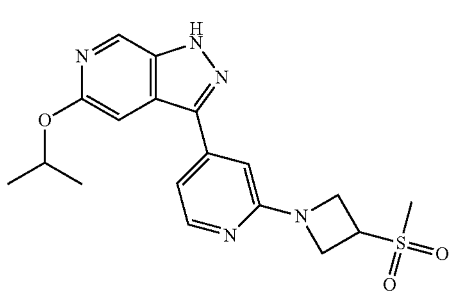 [SMILES: CC(C)Oc1cc2c(-c3ccnc(N4CC(S(C)(=O)=O)C4)c3)n[nH]c2cn1] | 388.1 | 0.70 | D | 48 |

TABLE J-continued

| Example | Structure | m/z | Ret Time (min) | Cond. | LRRK2 IC$_{50}$ (nM) |
|---|---|---|---|---|---|
| J15 | 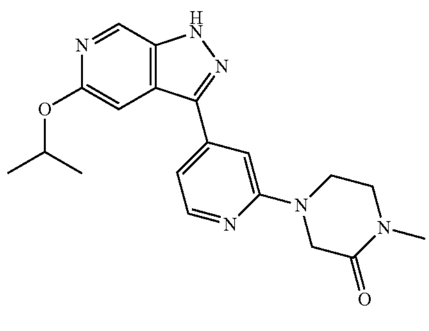 [SMILES: CC(C)Oc1cc2c(-c3ccnc(N4CCN(C)C(=O)C4)c3)n[nH]c2cn1] | 367.2 | 0.75 | D | 44 |
| J16 | 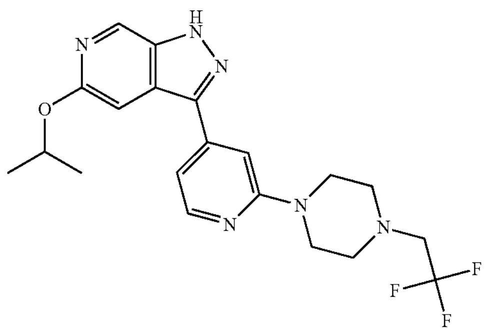 [SMILES: CC(C)Oc1cc2c(-c3ccnc(N4CCN(CC(F)(F)F)CC4)c3)n[nH]c2cn1] | 421.2 | 1.07 | D | 40 |
| J17 | 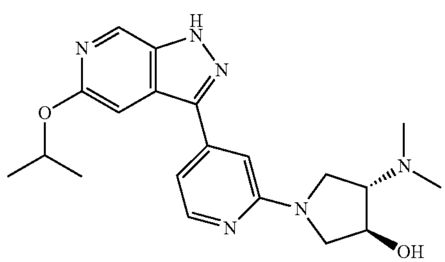 [SMILES: CC(C)Oc1cc2c(-c3ccnc(N4C[C@H](O)[C@@H](N(C)C)C4)c3)n[nH]c2cn1] | 383.2 | 0.70 | D | 44 |
| J18 | 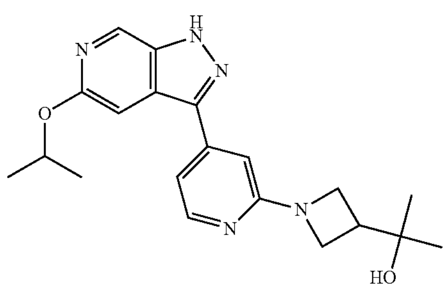 [SMILES: CC(C)Oc1cc2c(-c3ccnc(N4CC(C(C)(C)O)C4)c3)n[nH]c2cn1] | 368.2 | 0.80 | D | 77 |
| J19 | 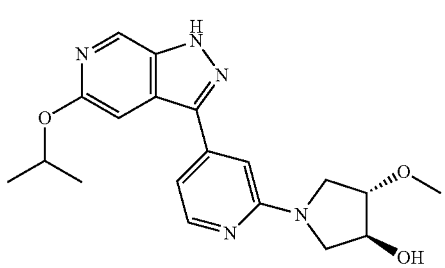 [SMILES: CO[C@H]1CN(c2cc(-c3n[nH]c4cnc(OC(C)C)cc34)ccn2)C[C@@H]1O] | 370.2 | 0.72 | D | 80 |

TABLE J-continued
| Example | Structure | m/z | Ret Time (min) | Cond. | LRRK2 IC$_{50}$ (nM) |
|---|---|---|---|---|---|
| J20 | 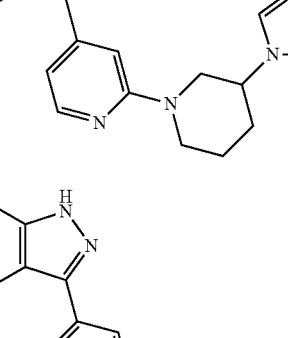 | 405.2 | 0.83 | D | 28 |
| J21 | 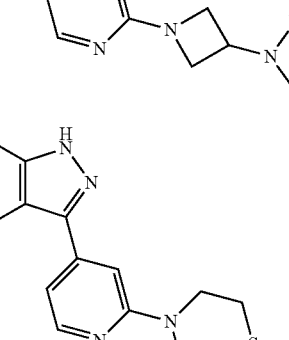 | 376.2 | 0.82 | D | 83 |
| J22 | 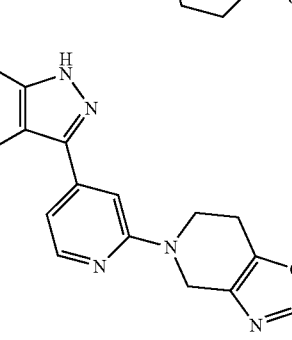 | 372.1 | 0.69 | D | 67 |
| J23 | 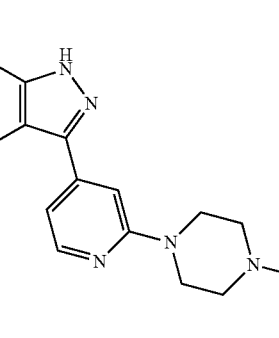 | 417.2 | 1.05 | D | 129 |
| J24 | 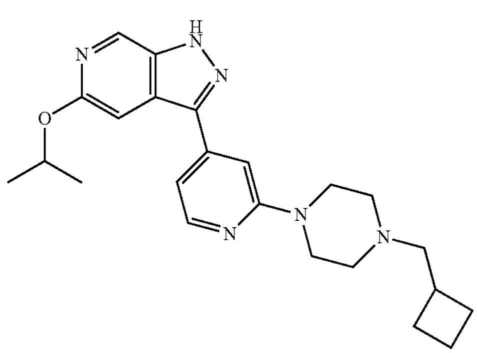 [SMILES: CC(C)Oc1cc2c(-c3ccnc(N4CCN(CC5CCC5)CC4)c3)n[nH]c2cn1] | 407.3 | 1.16 | D | 127 |

TABLE J-continued

| Example | Structure | m/z | Ret Time (min) | Cond. | LRRK2 IC$_{50}$ (nM) |
|---|---|---|---|---|---|
| J25 | 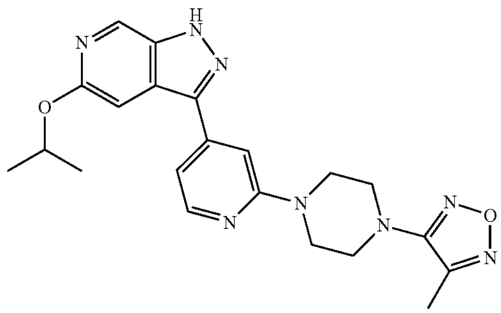 [SMILES: Cc1nonc1N1CCN(c2cc(-c3n[nH]c4cnc(OC(C)C)cc34)ccn2)CC1] | 421.2 | 1.03 | D | 102 |
| J26 | 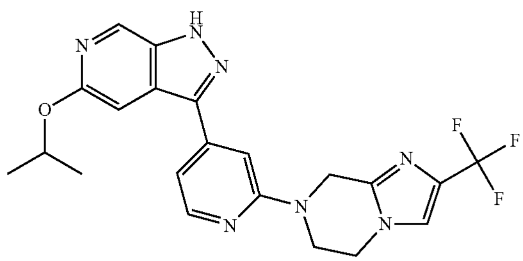 [SMILES: CC(C)Oc1cc2c(-c3ccnc(N4CCn5cc(C(F)(F)F)nc5C4)c3)n[nH]c2cn1] | 444.2 | 0.96 | D | 135 |
| J27 | 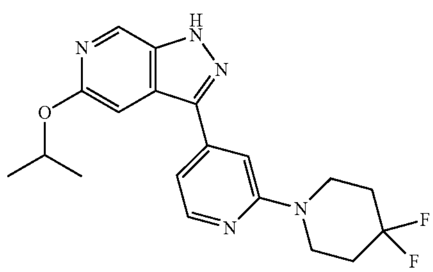 [SMILES: CC(C)Oc1cc2c(-c3ccnc(N4CCC(F)(F)CC4)c3)n[nH]c2cn1] | 374.2 | 1.05 | D | 143 |
| J28 | 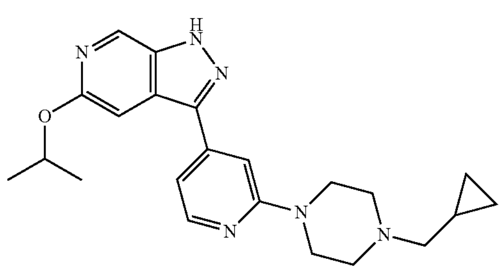 [SMILES: CC(C)Oc1cc2c(-c3ccnc(N4CCN(CC5CC5)CC4)c3)n[nH]c2cn1] | 393.2 | 1.02 | D | 82 |
| J29 | 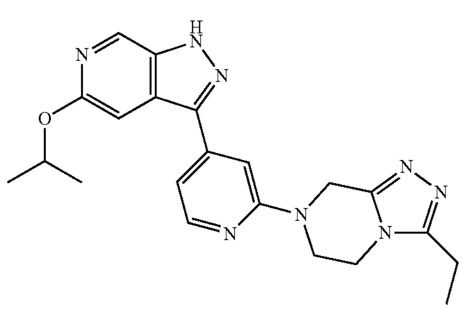 [SMILES: CCc1nnc2n1CCN(c1cc(-c3n[nH]c4cnc(OC(C)C)cc34)ccn1)C2] | 405.2 | 0.76 | D | 102 |

TABLE J-continued

| Example | Structure | m/z | Ret Time (min) | Cond. | LRRK2 IC$_{50}$ (nM) |
|---|---|---|---|---|---|
| J30 | 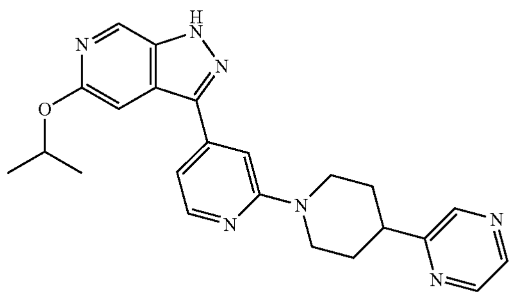 [SMILES: CC(C)Oc1cc2c(-c3ccnc(N4CCC(c5cnccn5)CC4)c3)n[nH]c2cn1] | 416.2 | 0.93 | D | 20 |
| J31 | 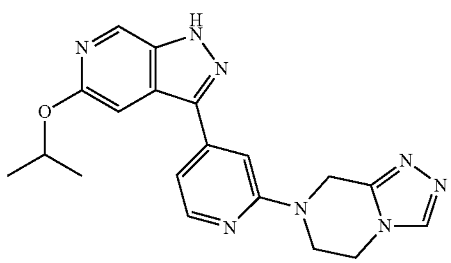 [SMILES: CC(C)Oc1cc2c(-c3ccnc(N4CCn5cnnc5C4)c3)n[nH]c2cn1] | 376.2 | 0.79 | D | 81 |
| J32 | 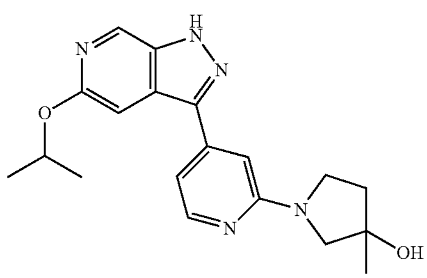 [SMILES: CC(C)Oc1cc2c(-c3ccnc(N4CCC(C)(O)C4)c3)n[nH]c2cn1] | 354.2 | 0.77 | D | 40 |
| J33 | 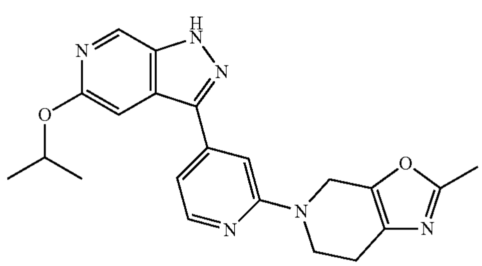 [SMILES: Cc1nc2c(o1)CN(c1cc(-c3n[nH]c4cnc(OC(C)C)cc34)ccn1)CC2] | 391.2 | 0.93 | D | 46 |
| J34 | 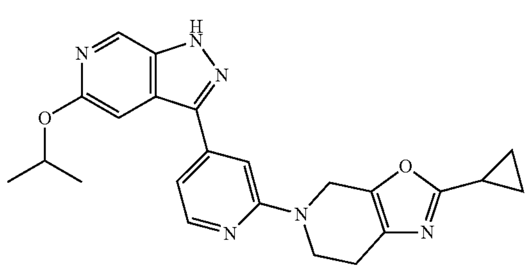 [SMILES: CC(C)Oc1cc2c(-c3ccnc(N4CCc5nc(C6CC6)oc5C4)c3)n[nH]c2cn1] | 417.2 | 1.03 | D | 55 |

TABLE J-continued
| Example | Structure | m/z | Ret Time (min) | Cond. | LRRK2 IC$_{50}$ (nM) |
|---|---|---|---|---|---|
| J35 | 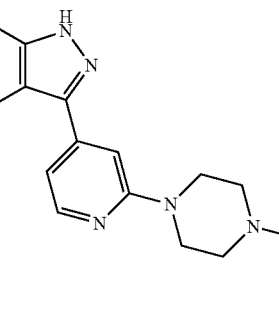 | 447.2 | 0.91 | D | 60 |
| J36 | 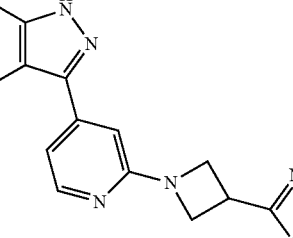 | 392.2 | 0.84 | D | 163 |
| J37 | 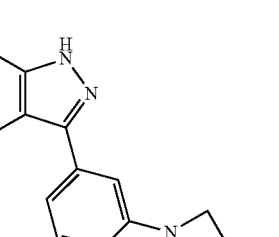 | 377.2 | 0.70 | D | 100 |
| J38 | 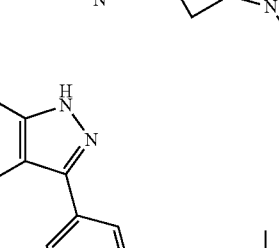 | 368.2 | 0.86 | D | 56 |
| J39 | 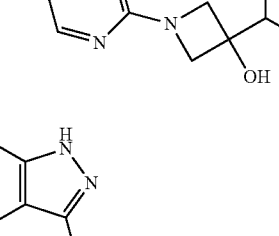 | 417.2 | 0.85 | D | 58 |

TABLE J-continued
| Example | Structure | m/z | Ret Time (min) | Cond. | LRRK2 IC$_{50}$ (nM) |
|---|---|---|---|---|---|
| J40 | 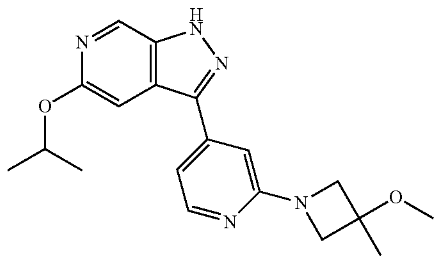 [SMILES: COC1(C)CN(c2cc(-c3n[nH]c4cnc(OC(C)C)cc34)ccn2)C1] | 354.2 | 0.87 | D | 42 |
| J41 | 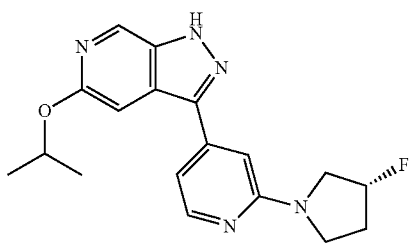 [SMILES: CC(C)Oc1cc2c(-c3ccnc(N4CC[C@@H](F)C4)c3)n[nH]c2cn1] | 342.2 | 0.89 | D | 26 |
| J42 | 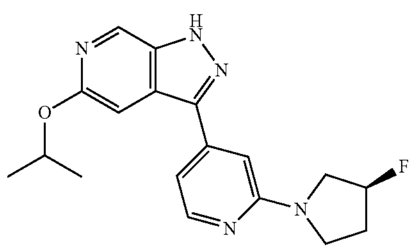 [SMILES: CC(C)Oc1cc2c(-c3ccnc(N4CC[C@H](F)C4)c3)n[nH]c2cn1] | 342.2 | 0.89 | D | 26 |
| J43 | 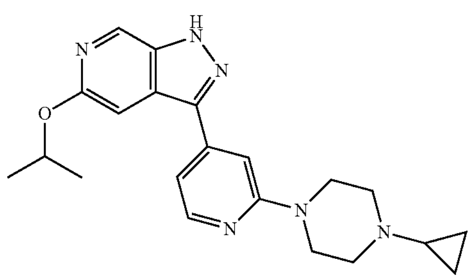 [SMILES: CC(C)Oc1cc2c(-c3ccnc(N4CCN(C5CC5)CC4)c3)n[nH]c2cn1] | 379.2 | 0.98 | D | 34 |
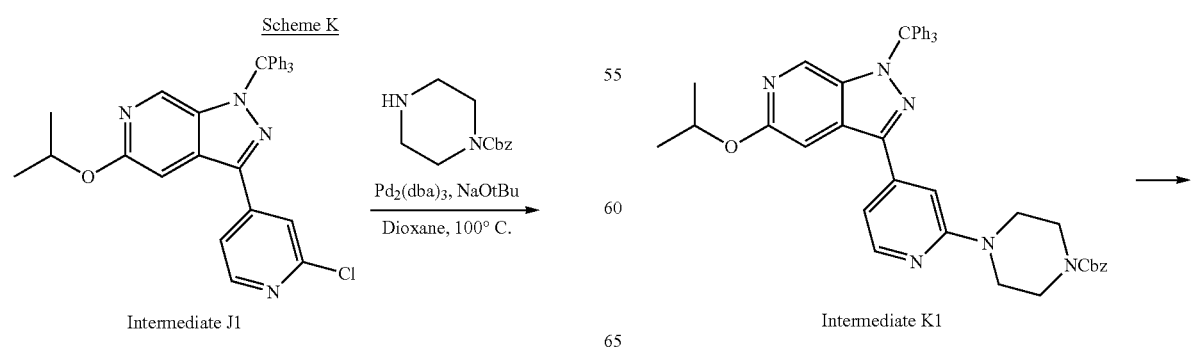
Scheme K

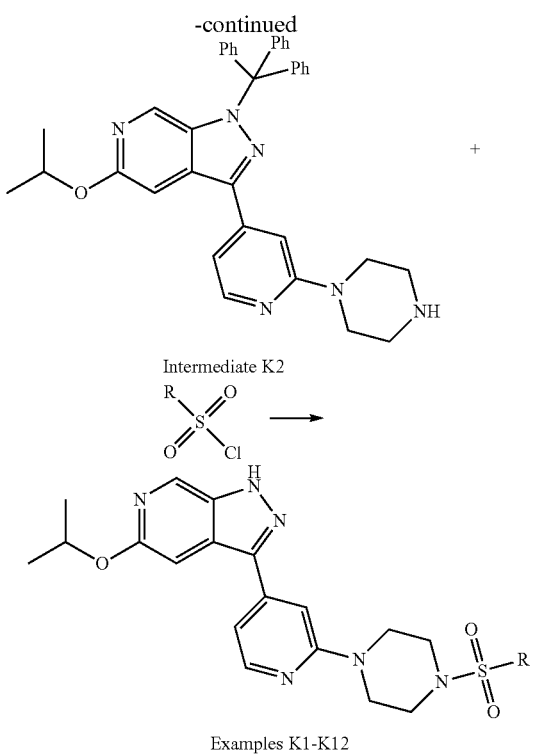

Step 1

A stirred mixture of Intermediate J1 (4 g, 7.53 mmol), N-Cbz-piperazine (1.991 g, 9.04 mmol), 1,3-bis(2,6-diisopropylphenyl)-imidazolidinium-chloride (0.643 g, 1.506 mmol) and sodium tert-butoxide (1.810 g, 18.83 mmol) in 1,4-dioxane (75 ml) was purged with argon for 15 min. Then $Pd_2(dba)_3$ (0.690 g, 0.753 mmol) was added and the mixture was heated at 100° C. overnight. The reaction was filtered through a pad of celite and washed with DCM. The filtrate was concentrated to leave a residue which was then purified by silica gel column chromatography (gradient elution with 5:1 to 2:1 hexane:EtOAc) to yield the Intermediate K1.

Step 2

To a stirred solution of Intermediate K1 (2.9 g, 4.06 mmol) in MeOH (4 ml), THF (8 mL), and Ethyl acetate (8 ml) was added 10% Pd/C (0.432 g, 0.406 mmol). The flask was evacuated and back-filled with hydrogen. The mixture was stirred at rt under an $H_2$ (1 atm) atmosphere for 8 h. The reaction was filtered through a pad of celite and washed with EtOAc. The filtrate was then concentrated and purified by reversed phase C18 HPLC to afford Intermediate K2.

Step 3

Parallel preparation of Examples K1-K12: To a set of vials containing a solution of Intermediate K2 (30 mg, 0.052 mmol) in DCE (1 mL) was added diisopropylethylamine (0.018 mL, 0.10 mmol) followed by the requisite sulfonyl chloride (0.062 mmol). The vials were capped and the mixtures were shaken at RT overnight. After that time, water (1 mL) was added to each vial and the mixtures were shaken at RT for 3 hours. The organic layer from each vial was transferred to a clean vial and the solutions were concentrated in vacuo. The crude residues were dissolved in DMSO (1 mL) and filtered. The crude products were purified by mass triggered HPLC using the following conditions: [Waters Sunfire C18 column, 5 µm, 30×100 mm, gradient 10-15% initial to a range of 35-95% final MeCN (0.1% formic acid) in water (0.1% formic acid) 50 mL/min, 8 min run time] to afford Examples K1-K12.

TABLE K

| Example | Structure | LCMS data m/z | Ret Time (min) | Cond. | LRRK2 IC$_{50}$ (nM) |
|---|---|---|---|---|---|
| K1 | 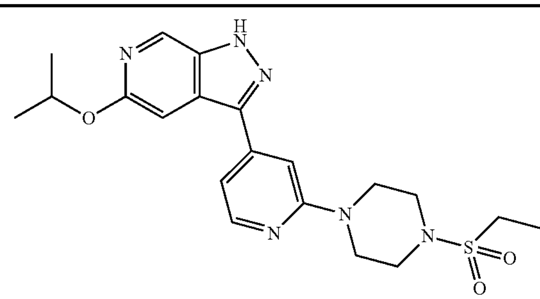 | 431.2 | 0.89 | D | 45 |
| K2 | 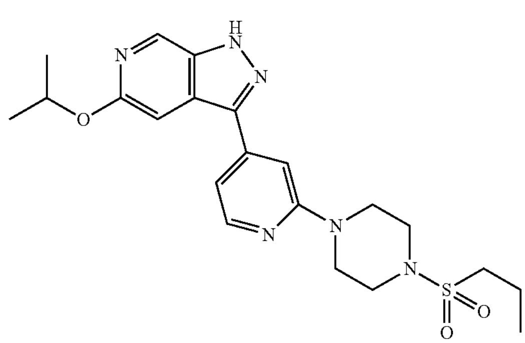 [SMILES: CCCS(=O)(=O)N1CCN(c2cc(-c3n[nH]c4cnc(OC(C)C)cc34)ccn2)CC1] | 445.2 | 0.95 | D | 25 |

TABLE K-continued
| Example | Structure | m/z | Ret Time (min) | Cond. | LRRK2 IC$_{50}$ (nM) |
|---|---|---|---|---|---|
| K3 | 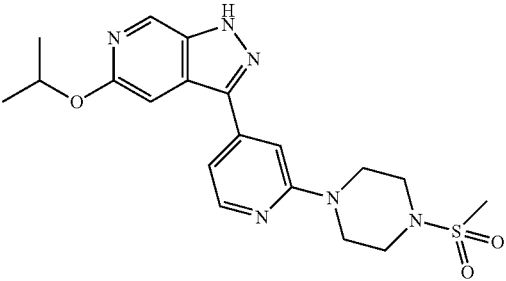 [SMILES: CC(C)Oc1cc2c(-c3ccnc(N4CCN(S(C)(=O)=O)CC4)c3)n[nH]c2cn1] | 417.2 | 0.83 | D | 24 |
| K4 | 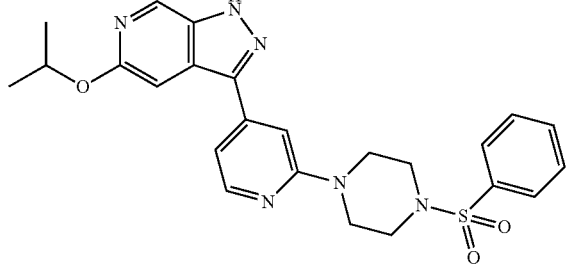 | 479.2 | 1.04 | D | 258 |
| K5 | 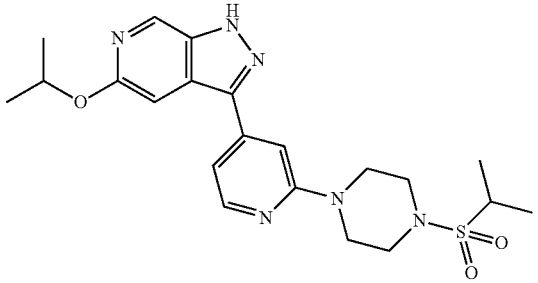 [SMILES: CC(C)Oc1cc2c(-c3ccnc(N4CCN(S(=O)(=O)C(C)C)CC4)c3)n[nH]c2cn1] | 445.2 | 0.94 | D | 34 |
| K6 | 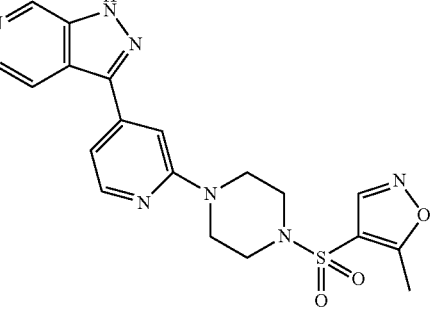 | 484.2 | 0.52 | D | 34 |
| K7 | 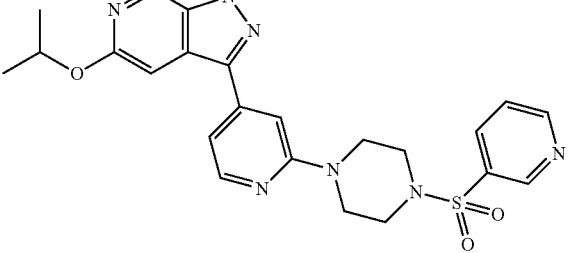 | 480.2 | 0.90 | D | 95 |

TABLE K-continued

| Example | Structure | m/z | Ret Time (min) | Cond. | LRRK2 IC$_{50}$ (nM) |
|---|---|---|---|---|---|
| K8 | 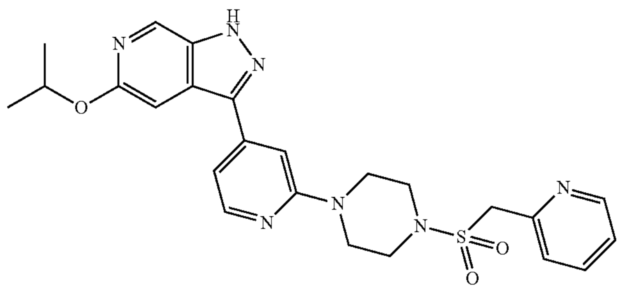 [SMILES: CC(C)Oc1cc2c(-c3ccnc(N4CCN(S(=O)(=O)Cc5ccccn5)CC4)c3)n[nH]c2cn1] | 494.2 | 0.89 | D | 32 |
| K9 | 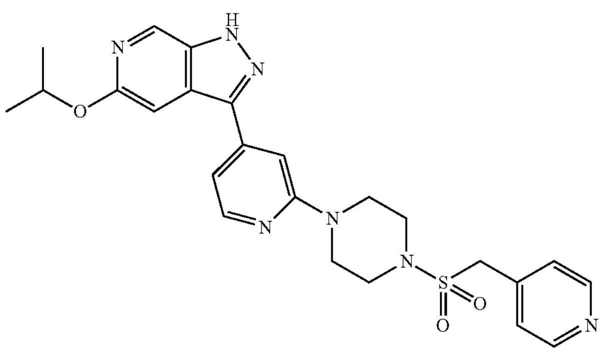 [SMILES: CC(C)Oc1cc2c(-c3ccnc(N4CCN(S(=O)(=O)Cc5ccncc5)CC4)c3)n[nH]c2cn1] | 494.2 | 0.85 | D | 40 |
| K10 | 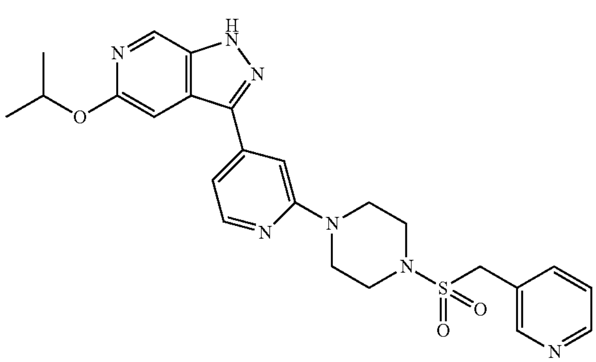 [SMILES: CC(C)Oc1cc2c(-c3ccnc(N4CCN(S(=O)(=O)Cc5cccnc5)CC4)c3)n[nH]c2cn1] | 494.2 | 0.84 | D | 43 |

TABLE K-continued

| Example | Structure | LCMS data m/z | Ret Time (min) | Cond. | LRRK2 IC$_{50}$ (nM) |
|---|---|---|---|---|---|
| K11 | 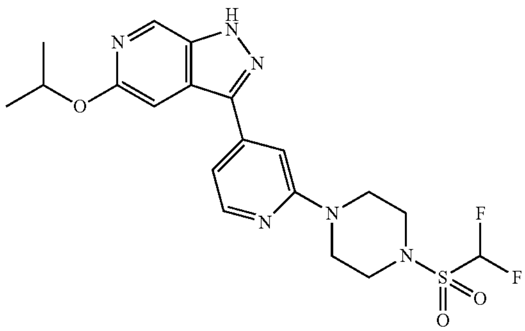 [SMILES: CC(C)Oc1cc2c(-c3ccnc(N4CCN(S(=O)(=O)C(F)F)CC4)c3)n[nH]c2cn1] | 453.2 | 0.99 | D | 152 |
| K12 | 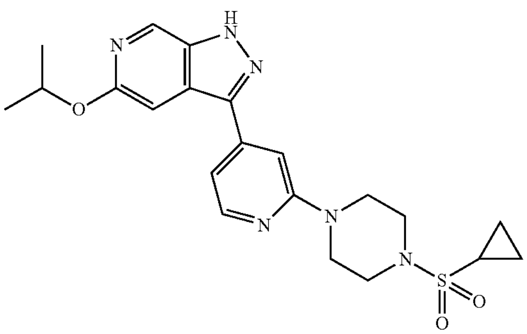 [SMILES: CC(C)Oc1cc2c(-c3ccnc(N4CCN(S(=O)(=O)C5CC5)CC4)c3)n[nH]c2cn1] | 443.2 | 0.91 | D | 45 |

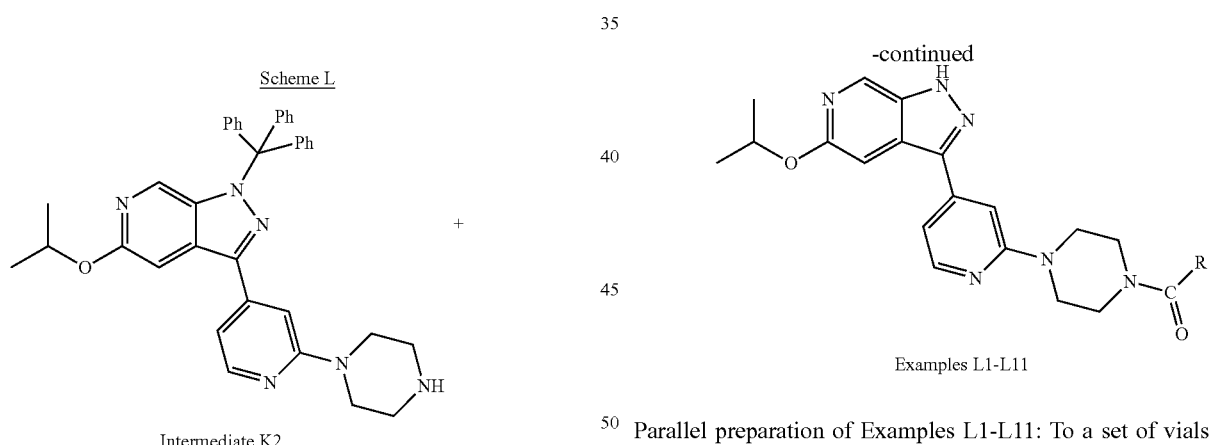

Scheme L

Intermediate K2

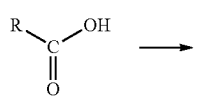

Examples L1-L11

Parallel preparation of Examples L1-L11: To a set of vials containing a solution of Intermediate K2 (23 mg, 0.040 mmol) in DCM (1 mL) was added diisopropylethylamine (0.028 mL, 0.16 mmol), T3P (50% in EtOAc, 0.059 mL, 0.10 mmol) followed by the requisite carboxylic acid (0.060 mmol). The vials were capped and the mixtures were shaken at RT overnight. After that time, water (1 mL) was added to each vial. The mixtures were then extracted with DCM and the separated organic layers were transferred to a new set of vials. To each vial was then added water (0.1 mL) and TFA (0.5 mL) and the mixtures were shaken at RT for 3 hours. After that time, the mixtures were concentrated in vacuo. The crude residues were dissolved in DMSO (1 mL) and filtered. The crude products were purified by mass triggered HPLC using the following conditions: [Waters Sunfire C18 column, 5 μm, 30×100 mm, gradient 10% initial to a range of 45-98% final MeCN (0.1% formic acid) in water (0.1% formic acid) 70 mL/min, 8-15 min run time] to afford Examples L1-L11.

TABLE L

| Example | Structure | LCMS data m/z | Ret Time | Cond. | LRRK2 IC$_{50}$ (nM) |
|---|---|---|---|---|---|
| L2 | 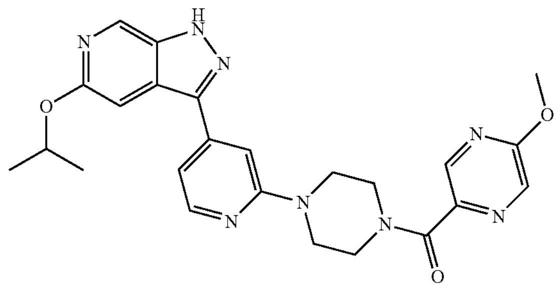 [SMILES: COc1cnc(C(=O)N2CCN(c3cc(-c4n[nH]c5cnc(OC(C)C)cc45)ccn3)CC2)cn1] | 475.2 | 0.92 | D | 45 |
| L3 | 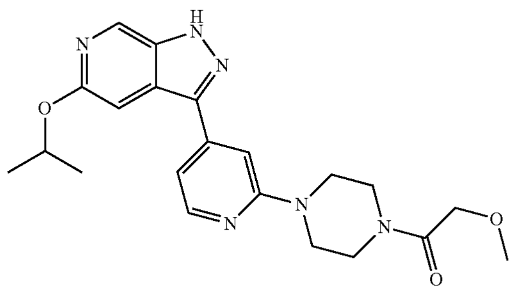 [SMILES: COCC(=O)N1CCN(c2cc(-c3n[nH]c4cnc(OC(C)C)cc34)ccn2)CC1] | 411.2 | 0.78 | D | 65 |
| L4 | 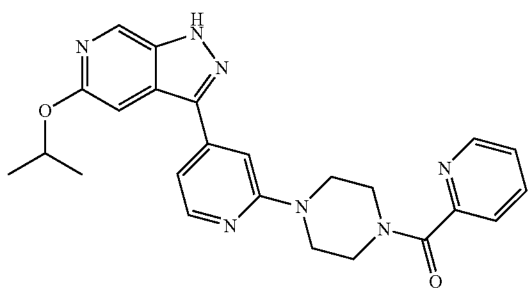 [SMILES: CC(C)Oc1cc2c(-c3ccnc(N4CCN(C(=O)c5ccccn5)CC4)c3)n[nH]c2cn1] | 444.2 | 0.83 | D | 57.02 |
| L5 | 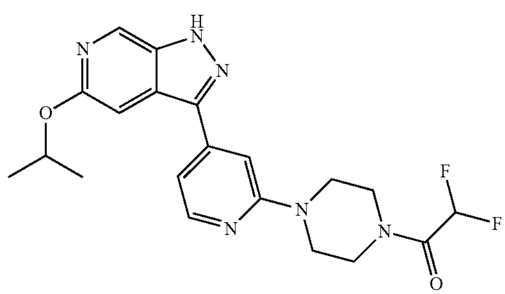 [SMILES: CC(C)Oc1cc2c(-c3ccnc(N4CCN(C(=O)C(F)F)CC4)c3)n[nH]c2cn1] | 417.2 | 0.89 | D | 85.93 |
| L6 | 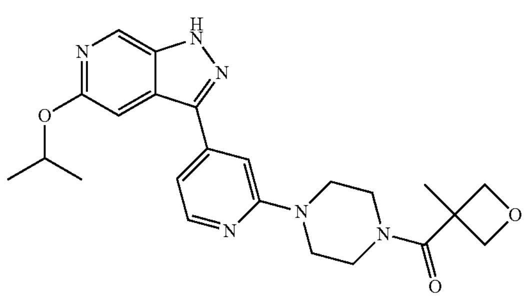 [SMILES: CC(C)Oc1cc2c(-c3ccnc(N4CCN(C(=O)C5(C)COC5)CC4)c3)n[nH]c2cn1] | 437.2 | 0.81 | D | 113.8 |

TABLE L-continued

| Example | Structure | LCMS data m/z | Ret Time | Cond. | LRRK2 IC$_{50}$ (nM) |
|---|---|---|---|---|---|
| L7 | 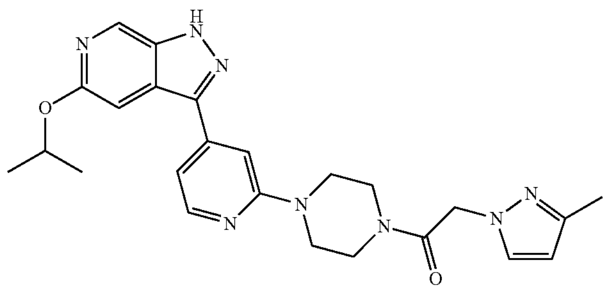 [SMILES: Cc1ccn(CC(=O)N2CCN(c3cc(-c4n[nH]c5cnc(OC(C)C)cc45)ccn3)CC2)n1] | 461.2 | 0.83 | D | 61.42 |
| L8 | 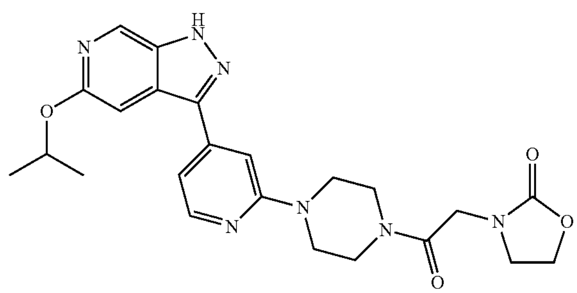 [SMILES: CC(C)Oc1cc2c(-c3ccnc(N4CCN(C(=O)CN5CCOC5=O)CC4)c3)n[nH]c2cn1] | 466.2 | 0.75 | D | 66.13 |
| L9 | 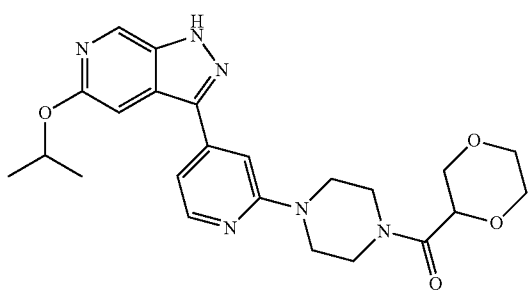 [SMILES: CC(C)Oc1cc2c(-c3ccnc(N4CCN(C(=O)C5COCCO5)CC4)c3)n[nH]c2cn1] | 453.2 | 0.81 | D | 76.26 |
| L10 | 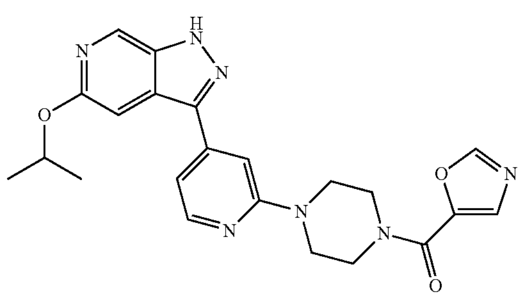 [SMILES: CC(C)Oc1cc2c(-c3ccnc(N4CCN(C(=O)c5cnco5)CC4)c3)n[nH]c2cn1] | 434.2 | 0.80 | D | 63.37 |
| L11 | 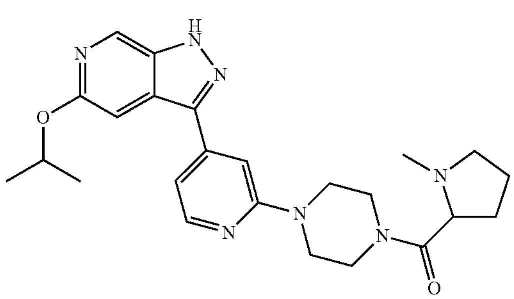 [SMILES: CC(C)Oc1cc2c(-c3ccnc(N4CCN(C(=O)C5CCCN5C)CC4)c3)n[nH]c2cn1] | 450.3 | 0.87 | D | 42.51 |

Scheme M

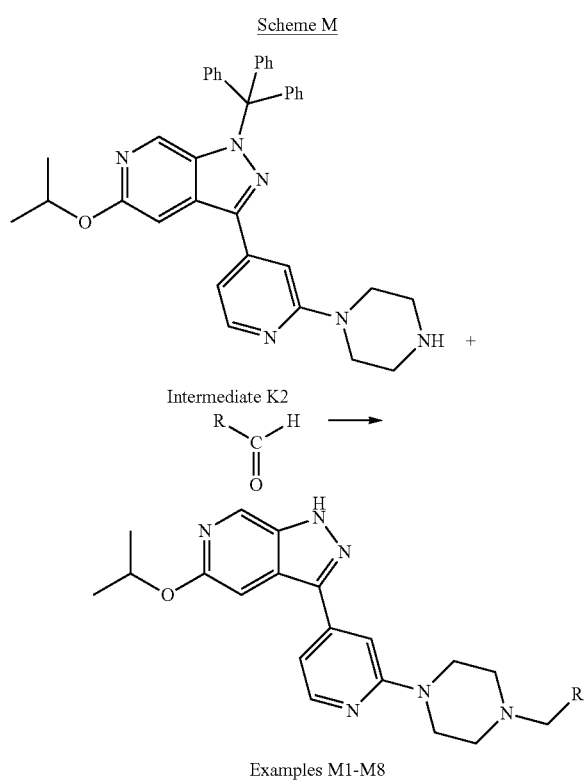

Intermediate K2

Examples M1-M8

Parallel preparation of Examples M1-M8: To a set of vials containing the requisite aldehyde (0.12 mmol) was added a solution of Intermediate K2 (35 mg, 0.060 mmol) in DCE (1 mL) followed by the addition of sodium triacetoxyborohydride (38 mg, 0.18 mmol). The vials were capped and the mixtures were shaken at RT for 2.5 days. After that time, additional aldehyde (0.12 mmol) and sodium triacetoxyborohydride (38 mg, 0.18 mmol) were added and the resultant mixtures were heated to 40° C. for 16 hours. After that time, water (1 mL) was added to each vial. The mixtures were then extracted with DCM and the separated organic layers were transferred to a new set of vials. To each vial was then added water (0.1 mL) and TFA (0.5 mL) and the mixtures were shaken at RT for 3 hours. After that time, the mixtures were concentrated in vacuo. The crude residues were dissolved in DMSO (1 mL) and filtered. The crude products were purified by mass triggered HPLC using the following conditions: [Waters Sunfire C18 column, 5 µm, 30×100 mm, gradient 10-35% initial to a range of 60-80% final MeCN (0.1% formic acid) in water (0.1% formic acid) 50 mL/min, 8-10 min run time] to afford Examples M1-M8.

TABLE M

| Example | Structure | LCMS data | | | LRRK2 |
| | | m/z | Ret Time | Cond. | $IC_{50}$ (nM) |
| --- | --- | --- | --- | --- | --- |
| M1 |  | 409.3 | 1.19 | D | 111 |
| M2 |  | 395.2 | 1.20 | D | 65 |

TABLE M-continued

| Example | Structure | LCMS data | | | LRRK2 |
| --- | --- | --- | --- | --- | --- |
| | | m/z | Ret Time | Cond. | IC$_{50}$ (nM) |
| M3 | 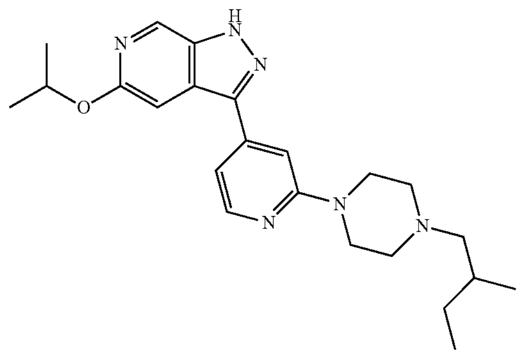 [SMILES: CCC(C)CN1CCN(c2cc(-c3n[nH]c4cnc(OC(C)C)cc34)ccn2)CC1] | 409.3 | 1.29 | D | 238 |
| M4 | 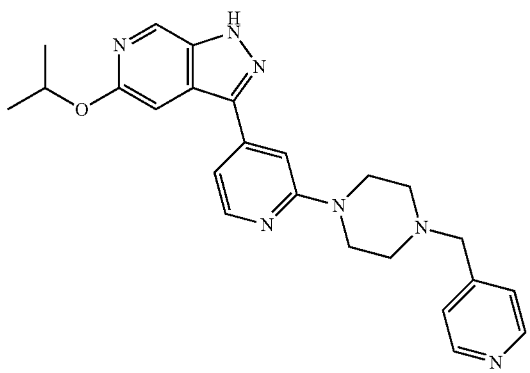 [SMILES: CC(C)Oc1cc2c(-c3ccnc(N4CCN(Cc5ccncc5)CC4)c3)n[nH]c2cn1] | 430.2 | 0.90 | D | 26 |
| M5 | 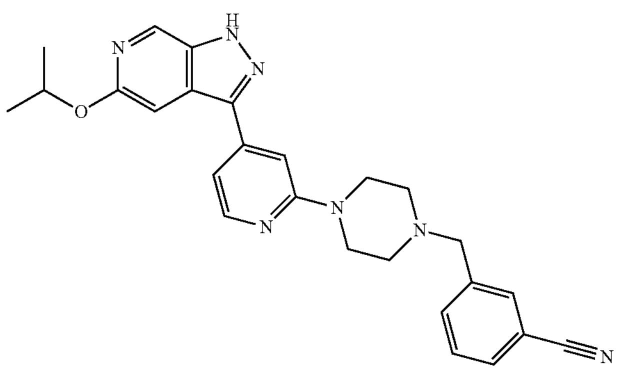 [SMILES: CC(C)Oc1cc2c(-c3ccnc(N4CCN(Cc5cccc(C#N)c5)CC4)c3)n[nH]c2cn1] | 454.2 | 1.07 | D | 88 |
| M6 | 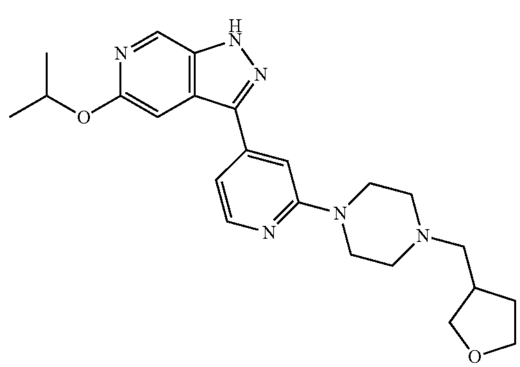 [SMILES: CC(C)Oc1cc2c(-c3ccnc(N4CCN(CC5CCOC5)CC4)c3)n[nH]c2cn1] | 423.2 | 0.92 | D | 30 |

TABLE M-continued

| | | LCMS data | | | LRRK2 |
|---|---|---|---|---|---|
| Example | Structure | m/z | Ret Time | Cond. | IC$_{50}$ (nM) |
| M7 | | Calc'd 469.2, found | 0.95 | D | 27 |
| M8 | | 437.2 | 0.97 | D | 30 |

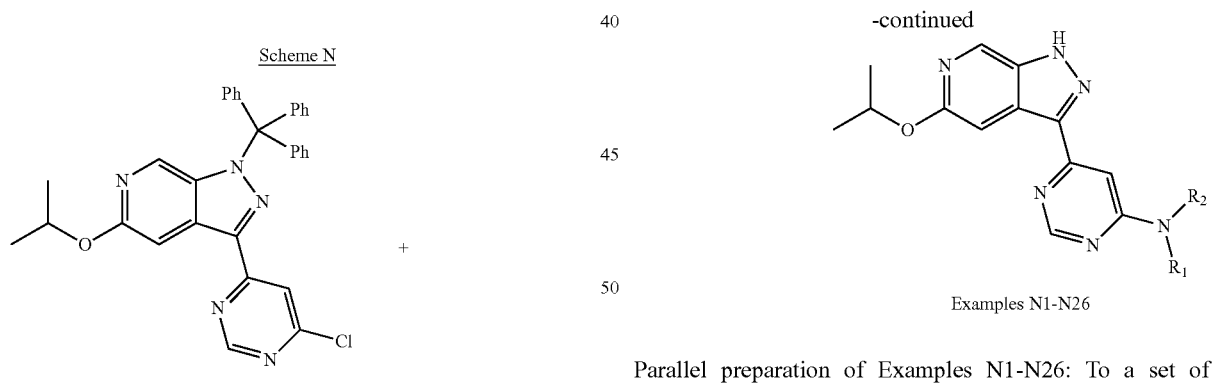

Examples N1-N26

Parallel preparation of Examples N1-N26: To a set of 2-dram vials containing the requisite amine (0.23 mmol) was added diisopropylethyl amine (49.2 µl, 0.282 mmol) and a slurry of the chloropyrimidine (from Scheme Q)(30 mg, 0.056 mmol) in DMSO (0.60 ml). The vials were capped and placed into a preheated heating block at 110° C. The mixtures were stirred at that temperature for 4 hours. After that time, the mixtures were allowed to cool to RT and sit for an additional 12 hours. To each vial was added water (2 mL) followed by DCM (2 mL). The mixtures were transferred to a fitted barrel filter and the organic layer from each vial was drained into a new 2-dram vial. To each of the aqueous layers was added additional DCM (1 mL). The organic layer was again drained into the 2-dram vials. To each vial was added TFA (500 µl, 6.49 mmol) and water (50

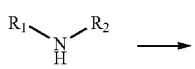

μl, 2.78 mmol). The vials were shaken at RT for 2 hours. The solutions were concentrated in vacuo. The crude products were then dissolved in DMSO (1 mL) and filtered. The crude products were purified by mass triggered HPLC using the following conditions: [Waters Sunfire C18 column, 5 μm, 30×100 mm, gradient 10-25% initial to a range of 28-95% final MeCN (0.1% formic acid) in water (0.1% formic acid) 50 mL/min, 8-10 min run time] to afford Examples N1-N26.

TABLE N

| Example | Structure | LCMS data m/z | Ret Time | Cond. | LRRK2 IC$_{50}$ (nM) |
|---|---|---|---|---|---|
| N1 | | 355.2 | 0.71 | D | 43 |
| N2 | | 384.2 | 0.70 | D | 42 |
| N3 | | 339.2 | 1.04 | D | 32 |
| N4 | | 311.2 | 0.78 | D | 69 |
| N5 | | 354.2 | 0.79 | D | 61 |

TABLE N-continued

| Example | Structure | LCMS data m/z | Ret Time | Cond. | LRRK2 IC$_{50}$ (nM) |
|---|---|---|---|---|---|
| N6 | 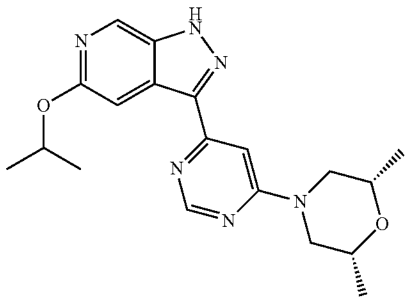 [SMILES: CC(C)Oc1cc2c(-c3cc(N4C[C@@H](C)O[C@@H](C)C4)ncn3)n[nH]c2cn1] | 369.2 | 0.98 | D | 30 |
| N7 | 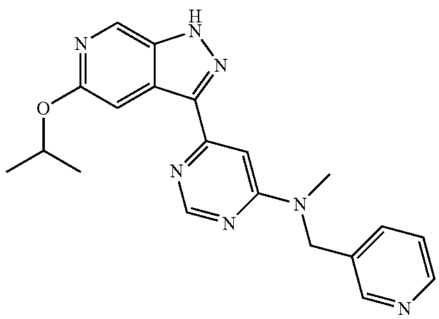 [SMILES: CC(C)Oc1cc2c(-c3cc(N(C)Cc4cccnc4)ncn3)n[nH]c2cn1] | 376.2 | 0.82 | D | 180 |
| N8 | 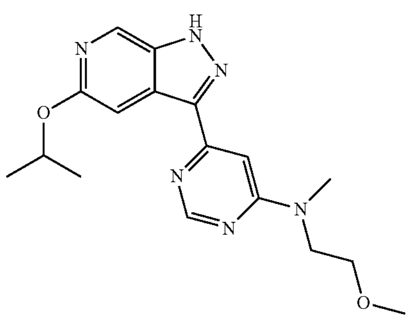 [SMILES: COCCN(C)c1cc(-c2n[nH]c3cnc(OC(C)C)cc23)ncn1] | 343.2 | 0.85 | D | 223 |
| N9 | 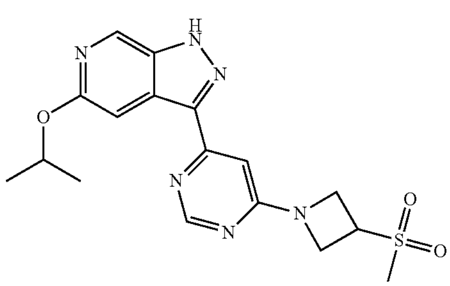 [SMILES: CC(C)Oc1cc2c(-c3cc(N4CC(S(C)(=O)=O)C4)ncn3)n[nH]c2cn1] | 389.1 | 0.64 | D | 65 |
| N10 | 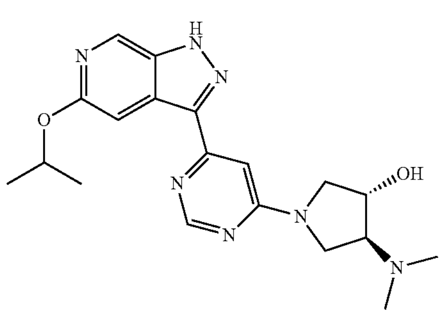 [SMILES: CC(C)Oc1cc2c(-c3cc(N4C[C@H](O)[C@@H](N(C)C)C4)ncn3)n[nH]c2cn1] | 384.2 | 0.65 | D | 69 |

TABLE N-continued

| Example | Structure | LCMS data m/z | Ret Time | Cond. | LRRK2 IC$_{50}$ (nM) |
|---|---|---|---|---|---|
| N11 | 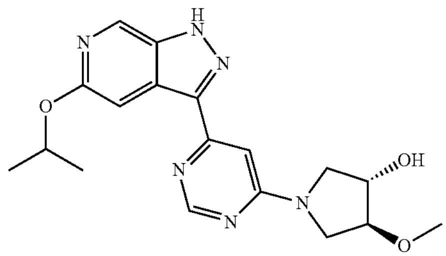 [SMILES: CO[C@H]1CN(c2cc(-c3n[nH]c4cnc(OC(C)C)cc34)ncn2)C[C@@H]1O] | 371.2 | 0.67 | D | 150 |
| N12 | 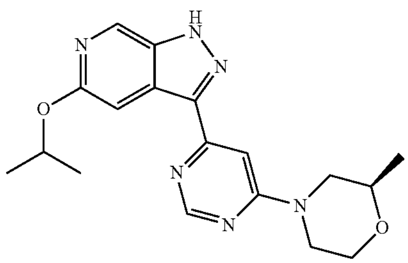 [SMILES: CC(C)Oc1cc2c(-c3cc(N4CCO[C@H](C)C4)ncn3)n[nH]c2cn1] | 355.2 | 0.89 | D | 32 |
| N13 | 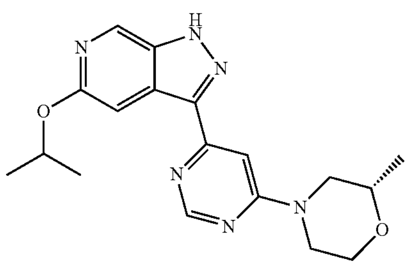 [SMILES: CC(C)Oc1cc2c(-c3cc(N4CCO[C@@H](C)C4)ncn3)n[nH]c2cn1] | 355.2 | 0.75 | D | 62 |
| N14 | 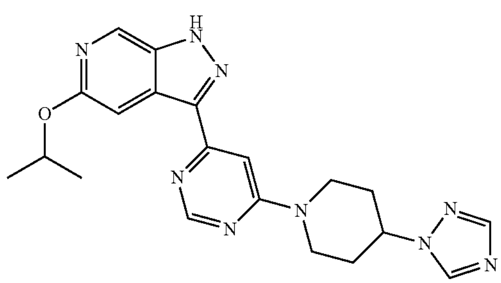 [SMILES: CC(C)Oc1cc2c(-c3cc(N4CCC(n5cncn5)CC4)ncn3)n[nH]c2cn1] | 406.2 | 0.75 | D | 41 |
| N15 | 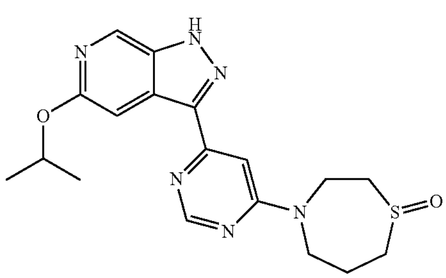 [SMILES: CC(C)Oc1cc2c(-c3cc(N4CCCS(=O)CC4)ncn3)n[nH]c2cn1] | 387.2 | 0.65 | D | 1262 |

TABLE N-continued

| Example | Structure | LCMS data m/z | Ret Time | Cond. | LRRK2 IC$_{50}$ (nM) |
|---|---|---|---|---|---|
| N17 | 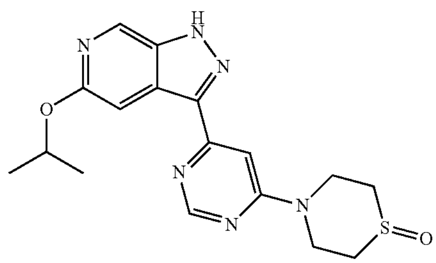 [SMILES: CC(C)Oc1cc2c(-c3cc(N4CCS(=O)CC4)ncn3)n[nH]c2cn1] | 373.1 | 0.64 | D | 129 |
| N18 | 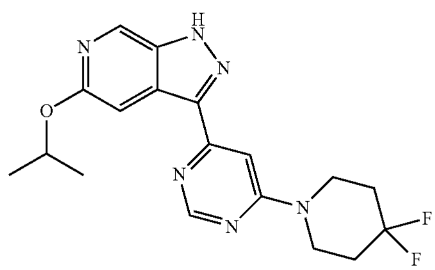 [SMILES: CC(C)Oc1cc2c(-c3cc(N4CCC(F)(F)CC4)ncn3)n[nH]c2cn1] | 375.2 | 1.01 | D | 71 |
| N19 | 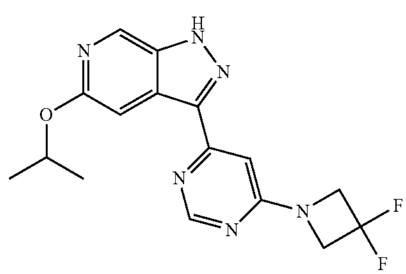 [SMILES: CC(C)Oc1cc2c(-c3cc(N4CC(F)(F)C4)ncn3)n[nH]c2cn1] | 347.1 | 0.86 | D | 111 |
| N20 | 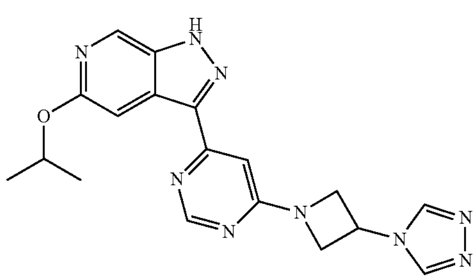 [SMILES: CC(C)Oc1cc2c(-c3cc(N4CC(n5cnnc5)C4)ncn3)n[nH]c2cn1] | 378.2 | 0.64 | D | 201 |
| N21 | 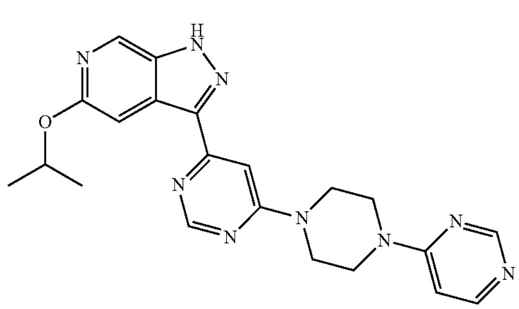 [SMILES: CC(C)Oc1cc2c(-c3cc(N4CCN(c5ccncn5)CC4)ncn3)n[nH]c2cn1] | 418.2 | 0.80 | D | 69 |

TABLE N-continued
| Example | Structure | LCMS data m/z | Ret Time | Cond. | LRRK2 IC$_{50}$ (nM) |
|---|---|---|---|---|---|
| N22 | 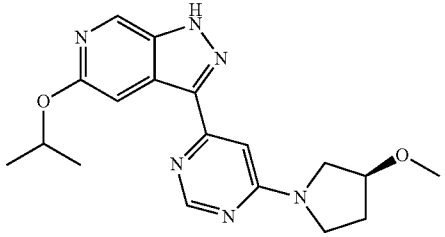 [SMILES: CO[C@H]1CCN(c2cc(-c3n[nH]c4cnc(OC(C)C)cc34)ncn2)C1] | 355.2 | 0.80 | D | 95 |
| N23 | 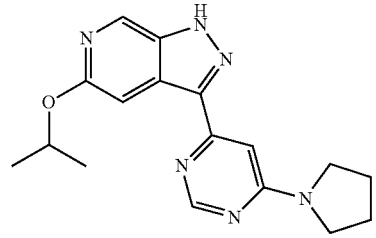 [SMILES: CC(C)Oc1cc2c(-c3cc(N4CCCC4)ncn3)n[nH]c2cn1] | 325.2 | 0.88 | D | 102 |
| N24 | 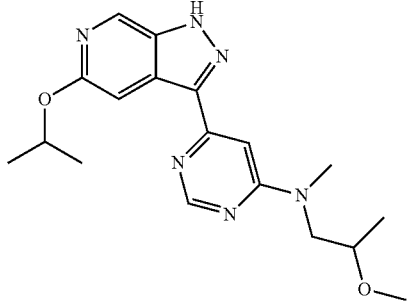 [SMILES: COC(C)CN(C)c1cc(-c2n[nH]c3cnc(OC(C)C)cc23)ncn1] | 357.2 | 0.92 | D | 62 |
| N25 | 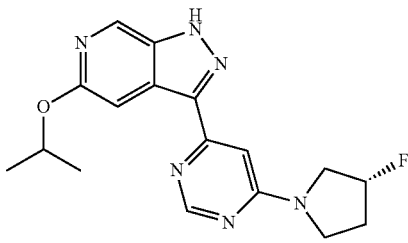 [SMILES: CC(C)Oc1cc2c(-c3cc(N4CC[C@@H](F)C4)ncn3)n[nH]c2cn1] | 343.2 | 0.82 | D | 365 |
| N26 | 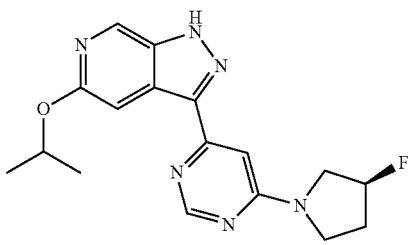 [SMILES: CC(C)Oc1cc2c(-c3cc(N4CC[C@H](F)C4)ncn3)n[nH]c2cn1] | 343.2 | 0.82 | D | 34 |

Scheme O

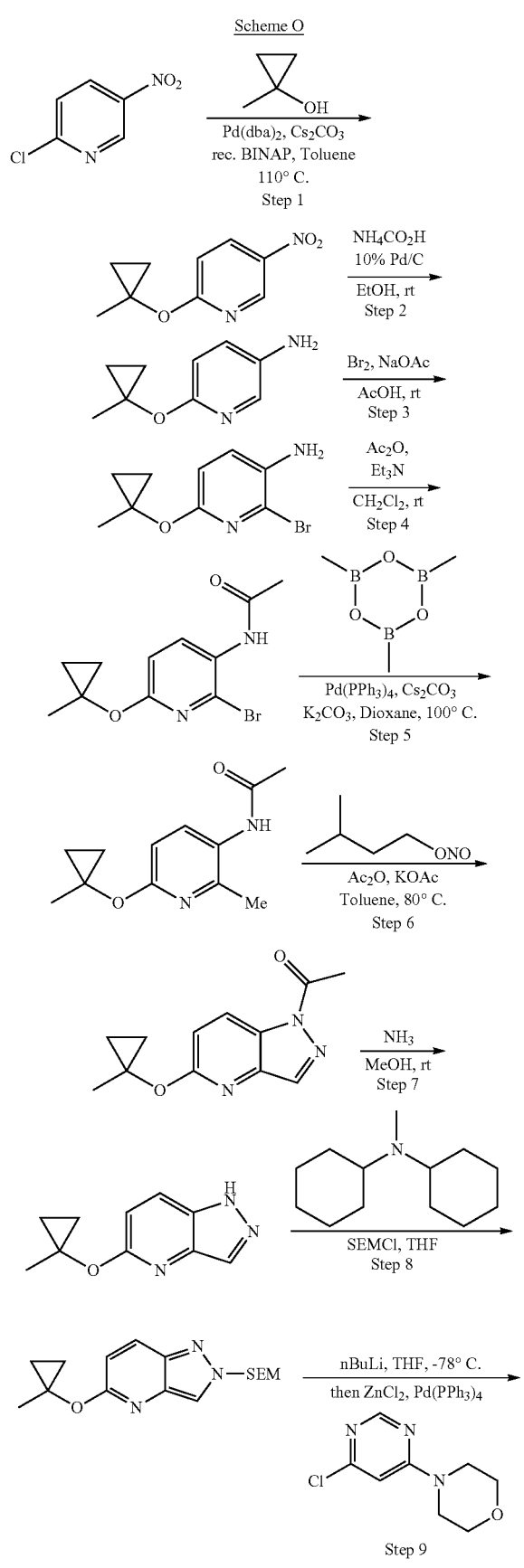

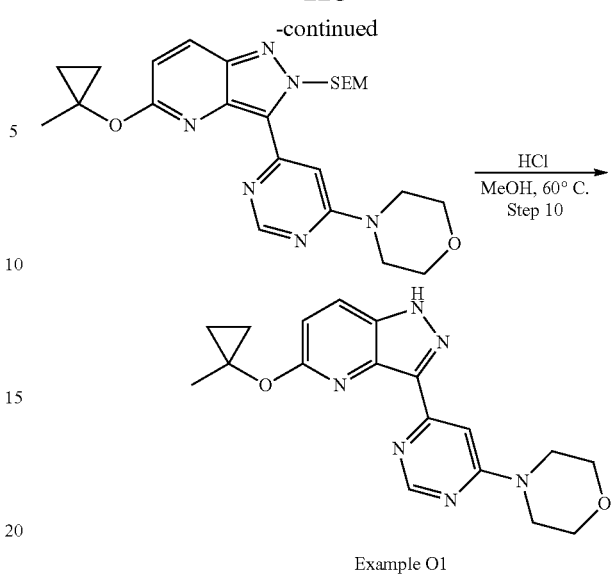

Example O1

Step 1

A flask containing a mixture of Cs$_2$CO$_3$ (12.23 g, 37.5 mmol), Pd(dba)$_2$ (0.31 g, 0.54 mmol) and racemic BINAP (1.00 g, 1.61 mmol) was evacuated and back-filled with N$_2$. To this mixture were added 2-chloro-5-nitropyridine (4.25 g, 26.8 mmol) and 1-methylcyclopropanol (2.58 ml, 32.2 mmol) in toluene (9.9 mL) and the mixture was stirred at 110° C. for 1 h. The mixture was cooled to room temperature and filtered through a pad of silica gel. The pad was washed with EtOAc (100 mL). The filtrate was concentrated under reduced pressure to leave a residue which was purified by column chromatography on silica (elution with 100:0 to 4:1 hexane:EtOAc) to yield the ether.

Step 2

To a cold (0° C.), stirred mixture of the ether from Step 1 (20.7 g, 107 mmol) and ammonium formate (26 g, 412 mmol) in EtOH (350 mL) was added 10% Pd/C (1.2 g, 1.13 mmol) under N$_2$. After being stirred at 0° C. for 15 min the reaction was stirred at room temperature for 2 h. The reaction was diluted with EtOAc (500 mL) and the resulting solution with filtered through a pad of silica gel. The silica pad was then washed with EtOAc (500 mL) and the combined filtrates were concentrated under reduced pressure to afford the desired amine, which was used in the next step without further purification.

Step 3

To a stirred solution of the above amine (4.93 g, 30.0 mmol) in acetic acid (25.0 ml) was added NaOAc (2.39 g, 29.1 mmol) followed by Br$_2$ (1.44 ml, 27.9 mmol) dropwise over 10 min. After being stirred at room temperature for 1.5 h, the thick, dark red reaction mixture was added to cold (0° C.) aqueous solution of NaOH (1N) to bring the pH-8. The resulting layer was then extracted with EtOAc (×3). The combined organic layers were dried, filtered and concentrated under reduced pressure to leave a residue which was purified by flash chromatography (elution with 2:1 hexane:EtOAc) to yield the bromide.

Step 4

To a cold (0° C.), stirred solution of the above bromide (5.76 g, 23.69 mmol) in DCM (47 mL) was added Et$_3$N (9.91 ml, 71.1 mmol) followed by acetic anhydride (4.02 ml, 42.6 mmol). The cold bath was removed and the mixture was stirred at room temperature overnight. The reaction was quenched with a saturated aqueous solution of NaHCO$_3$ and the resulting layer was extracted with DCM (×3). The combined organic layers were dried, filtered and concentrated under reduced pressure to leave a residue which was purified by flash chromatography (elution with 3:2 hexane:EtOAc) to yield the acetamide.

Step 5

A flask containing a mixture of the above acetamide (4.1 g, 14.4 mmol), $Cs_2CO_3$ (4.68 g, 14.38 mmol) and $K_2CO_3$ (3.97 g, 28.8 mmol) in 1,4-dioxane (48 mL) was evacuated and back-filled with $N_2$. To this mixture was added $Pd(PPh_3)_4$ (1.66 g, 1.44 mmol) followed by trimethylboroxine (4.42 mL, 31.6 mmol) and the mixture was heated at 100° C. overnight. The reaction was cooled to room temperature and filtered though a pad of celite. The filtrate was concentrated under reduced pressure to leave a residue which was purified by column chromatography on silica (elution with 1:1 hexane:EtOAc) to yield the methylpyridine.

Step 6

A stirred mixture of the above methylpyridine (2.19 g, 9.94 mmol), KOAc (1.46 g, 14.9 mmol) and acetic anhydride (4.32 mL, 45.7 mmol) in toluene (11 mL) was heated to 80° C. when isoamylnitrite (4.66 g, 39.8 mmol) was added dropwise. After the addition was complete the mixture was heated at 80° C. overnight. After being cooled to room temperature the mixture was filtered through a pad of celite. The filtrate was concentrated to leave a residue which was purified by column chromatography on silica (elution with 100:1 to 15:1 hexane:EtOAc) to yield the acyl indazole as a light yellow solid.

Step 7

To a stirred suspension of the acyl indazole from step 6 (1.74 g, 7.51 mmol) in MeOH (1.1 mL) was added $NH_3$ (5.4 mL of 7.0 M solution in methanol, 37.5 mmol). After being stirred at room temperature for 3 h the reaction was concentrated under reduced pressure to leave a residue which was purified by column chromatography on silica (elution with 100:1 to 2:3 hexane:EtOAc) to yield the desired 4-azaindazole.

Step 8

To a cold (0° C.), stirred solution of above 4-azaindazole (1.23 g, 6.48 mmol) in THF (21.6 mL) was added N,N-dicyclohexylmethylamine (1.81 ml, 8.43 mmol) followed by SEMCl (1.26 ml, 7.13 mmol) dropwise over 3 min. The mixture was slowly warmed to room temperature and stirred overnight. The reaction was cooled to 0° C. followed by addition of diethylether. The solid was filtered and the filtrate was concentrated under reduced pressure to leave a residue which was purified by column chromatography (elution with 100:1 to 5:1 hexane:EtOAc) to yield the desired SEM-protected azaindazole.

Step 9

To a cold (−78° C.), stirred solution of the SEM-protected 4-azaindazole (0.7 g, 2.19 mmol) in THF (4.4 mL) was added n-BuLi (1.78 mL of 1.6 M solution in hexane, 2.85 mmol). After the addition was complete the mixture was stirred at −78° C. for 15 min and then warmed to −20° C. for 5 min. The mixture was cooled to −78° C. after which time freshly prepared $ZnCl_2$ (6.6 mL of 0.5 M solution in THF, 3.3 mmol) was added. The mixture was then raised to −20° C. and stirred at −20° C. for 10 min, afterwards a mixture of 4-(6-chloropyrimidin-4-yl)morpholine (0.48 g, 2.4 mmol) and $Pd(PPh_3)_4$ (0.13 g, 0.11 mmol) was added. The cold bath was removed and the mixture was heated at 50° C. for 4 h. The reaction was then cooled to room temperature and stirred overnight. The reaction was quenched with a saturated aqueous solution of $NH_4Cl$ and the resulting layer was extracted with DCM (×3). The combined organic layers were dried, filtered and concentrated under reduced pressure to leave a residue which was purified by flash chromatography (elution with 2:1 hexane:EtOAc) to yield the pyrimidine adduct.

Step 10

To a stirred solution of morpholine adduct from step 9 (112 mg, 0.232 mmol) in MeOH (1.5 mL) was added HCl (1.2 mL of 4 M solution in 1,4-Dioxane, 4.64 mmol) and the mixture was heated at 60° C. for 45 min. After being cooled to room temperature the reaction was slowly poured into a saturated aqueous solution of $NaHCO_3$ and the resulting layer was extracted with DCM (×2). The combined organic layers were dried, filtered, and concentrated to leave a residue which was purified by LCMS Condition G to afford Example O1.

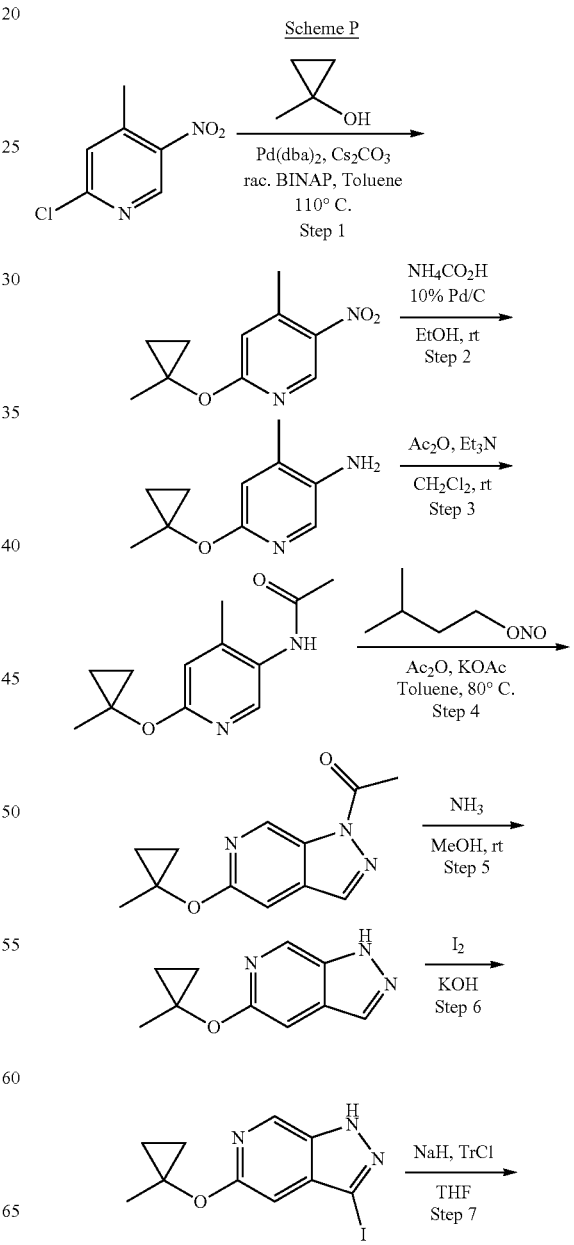

Scheme P

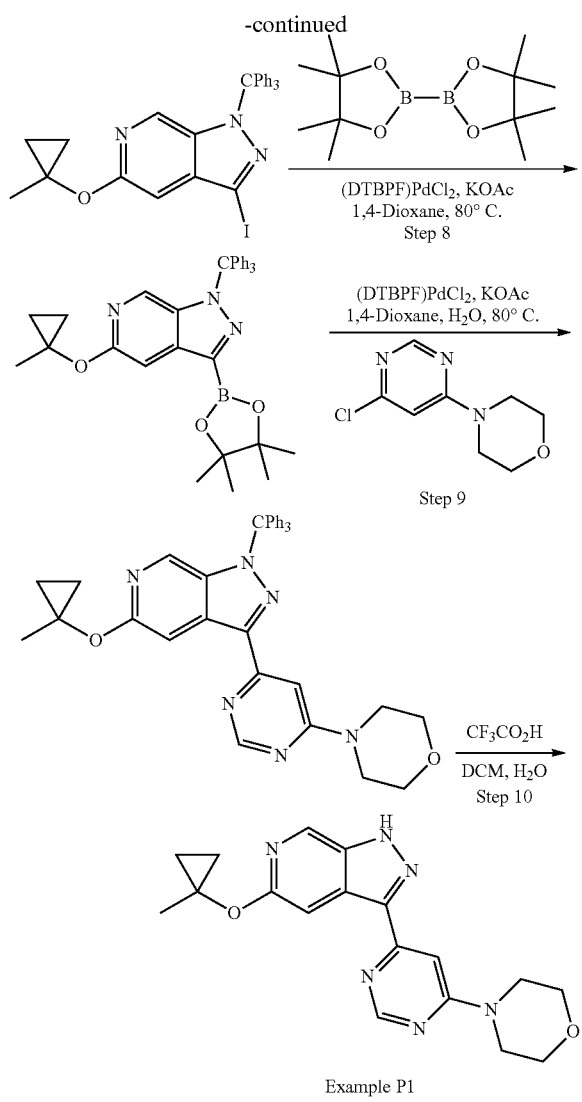

Example P1

Step 1

To a stirred, nitrogen-purged mixture of 1-methylcyclopropanol (0.56 ml, 6.95 mmol) and 2-chloro-4-methyl-5-nitropyridine (1.0 g, 5.79 mmol) in toluene (2.15 mL) were added Cs$_2$CO$_3$ (2.64 g, 8.11 mmol), Pd(dba)$_2$ (0.067 g, 0.116 mmol) and racemic BINAP (0.22 g, 0.35 mmol) and the mixture was stirred at 100° C. for 3 h. After being cooled to room temperature the reaction was diluted with EtOAc and filtered through a mixture of celite and silica gel. The filter pad was then washed with EtOAc (500 mL). The combined filtrates were concentrated under reduced pressure to leave a residue which was purified by column chromatography on silica gel (elution with 0% to 25% EtOAc in hexanes) to afford 4-methyl-2-(1-methylcyclopropoxy)-5-nitropyridine.

Step 2

To a stirred, nitrogen-purged mixture of 4-methyl-2-(1-methylcyclopropoxy)-5-nitropyridine (1.14 g, 5.48 mmol) and ammonium formate (2.07 g, 32.9 mmol) in EtOH (27.4 ml) was added 10% Pd/C (0.58 g, 0.55 mmol). After being stirred at room temperature for 1 h, the reaction was diluted with EtOAc (200 mL) and filtered through a pad of silica gel. The pad was washed with EtOAc (300 mL) and the combined filtrates were concentrated under reduced pressure to afford 4-methyl-6-(1-methylcyclopropoxy)pyridin-3-amine as a film, which was directly used in the next step without further purification.

Step 3

To a stirred mixture of aminopyridine from step 2 (0.68 g, 3.82 mmol) and Et$_3$N (1.06 mL, 7.63 mmol) in CH$_2$Cl$_2$ (7.6 mL) was added Ac$_2$O (0.54 mL, 5.72 mmol) at room temperature. After being stirred at room temperature for 72 h the reaction was quenched with a saturated aqueous solution of NaHCO$_3$. The organic layer was separated and the aqueous layer was extracted with DCM. The combined organic layers were dried, filtered and concentrated under reduced pressure to leave a residue which was purified by column chromatography on silica gel (elution with 0% to 100% EtOAc in hexanes, then isocratic at 100% EtOAc) to afford N-(4-methyl-6-(1-methylcyclopropoxy)pyridin-3-yl) acetamide as a colorless oil.

Step 4

A stirred mixture of N-(4-methyl-6-(1-methylcyclopropoxy)pyridin-3-yl)acetamide (750 mg, 3.40 mmol), KOAc (501 mg, 5.11 mmol) and acetic anhydride (1.48 mL, 15.66 mmol) in toluene (18 mL) was heated to 80° C. when isoamylnitrite (1.83 mL, 13.62 mmol) was added dropwise. After the addition was complete the mixture was heated at 80° C. overnight. After being cooled to room temperature the mixture was filtered through a pad of celite. The filtrate was concentrated to leave a residue which was purified by column chromatography on silica (elution with 0% to 100% EtOAc in hexanes) to afford the desired cyclized product.

Step 5

To a stirred suspension of the cyclized product from step 4 (1.06 g, 4.58 mmol) in MeOH (5.7 mL) was added NH$_3$ (3.3 mL of 7.0 M solution in methanol, 22.92 mmol). After being stirred at room temperature for 3 h the reaction was concentrated under reduced pressure to leave a residue which was purified by column chromatography on silica (elution with 0% to 50% EtOAc in hexanes) to yield the desired 6-azaindazole.

Step 6

To a stirred solution of 6-azaindazole from step 5 (500 mg, 2.64 mmol) in DMF (4.4 mL) was added KOH (371 mg, 6.61 mmol) followed by I$_2$ (738 mg, 2.91 mmol). After being stirred at room temperature overnight, the reaction was quenched with a saturated aqueous solution of Na$_2$S$_2$O$_3$. The mixture was stirred for 25 min followed by the addition of water (25 mL). The mixture was acidified to pH 4 using 2 M HCl. The solid was filtered and dried under vacuum overnight to afford the desired iodoindazole.

Step 7

To a cold (0° C.), stirred solution of 3-iodo-5-(1-methylcyclopropoxy)-1H-pyrazolo[3,4-c]pyridine (700 mg, 2.22 mmol) in THF (7.4 mL) was added NaH (107 mg of 60% in oil, 2.67 mmol) and stirred for 10 min. To this solution was added TrCl (681 mg, 2.44 mmol). The cold bath was removed and the mixture was stirred at room temperature for 2 h. The reaction was quenched with a saturated aqueous solution of NaHCO$_3$ and the resulting layer was extracted with DCM (×3). The combined organic layers were dried, filtered, and concentrated under reduced pressure to leave a residue which was purified by column chromatography on silica (elution with 0% to 50% EtOAc in hexanes) to yield 3-iodo-5-(1-methylcyclopropoxy)-1-trityl-1H-pyrazolo[3,4-c]pyridine.

Step 8

To a stirred solution of 3-iodo-5-(1-methylcyclopropoxy)-1-trityl-1H-pyrazolo[3,4-c]pyridine (300 mg, 0.538 mmol) in 1,4-dioxane (2.5 mL) were added 4,4,4',4',5,5,5',5'-octamethyl-2,2'-bi(1,3,2-dioxaborolane) (205 mg, 0.807 mmol) and KOAc (158 mg, 1.615 mmol). The mixture was degassed with N$_2$ for 15 min when Pd (DTBPF)Cl$_2$ (17.54 mg, 0.027 mmol) was added. The mixture was then heated at 80° C. overnight. The mixture was diluted with 4:1 hex:EtOAc mixture (15 mL) and filtered through a pad of silica. The solid was thoroughly washed with 4:1 Hex:EtOAc solution (200 mL). The combined filtrates were concentrated and the product was used in the next step without further purification.

Step 9

To a mixture of 4-(6-chloropyrimidin-4-yl)morpholine (70.1 mg, 0.351 mmol), K$_3$PO$_4$ (172 mg, 0.810 mmol) and Pd(DTBPF)Cl$_2$ (8.80 mg, 0.014 mmol) was added 5-(1-methylcyclopropoxy)-3-(4,4,5,5-tetramethyl-1,3,2-dioxaborolan-2-yl)-1-trityl-1H-pyrazolo[3,4-c]pyridine (151 mg, 0.27 mmol) in Dioxane (2.7 ml) and Water (0.27 ml). The mixture was degassed with N$_2$ for 15 min and then heated at 80° C. for 15 h. The reaction was cooled to room temperature and diluted with 5:1 hexane:EtOAc (100 mL) and filtered through a small plug of silica. The filtrate was concentrated under reduced pressure to afford the desired pyrimidine adduct which was taken to the next step without further purification. LCMS 595.02 [M+1].

Step 10

To a stirred solution of 4-(6-(5-(1-methylcyclopropoxy)-1-trityl-1H-pyrazolo[3,4-c]pyridin-3-yl)pyrimidin-4-yl) morpholine (89 mg, 0.150 mmol) in CH$_2$Cl$_2$ (2 ml) and water (0.2 ml) was added TFA (1.5 mL) and the mixture was stirred at room temperature for 5 h. The reaction was carefully quenched with a saturated aqueous solution of NaHCO$_3$ (50 mL) and the resulting layer was extracted with DCM (3×50 mL). The combined organic layers were dried over MgSO$_4$, filtered and concentrated to leave a residue which was purified by LCMS Condition E to afford Example P1.

TABLE P

Utilizing a method similar to that outlined in Scheme P and substituting cis-4-(6-chloro-pyrimidin-4-yl)-2,6-dimethylmorpholine (Intermediate AC1) for 4-(6-chloropyrimidin-4-yl)morpholine in Step 9, the following compound was prepared:

| Ex | Structure | LCMS Cond. | RT (min) | m/z | IC$_{50}$ (nM) |
|---|---|---|---|---|---|
| P2 | 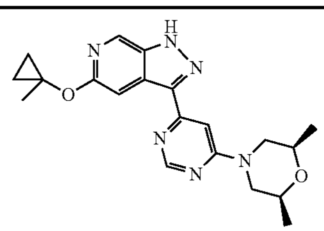 | F | 0.94 | 381 | 2.1 |

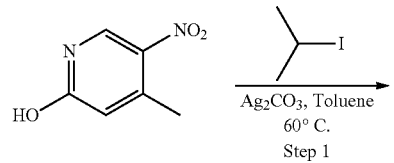

Scheme Q

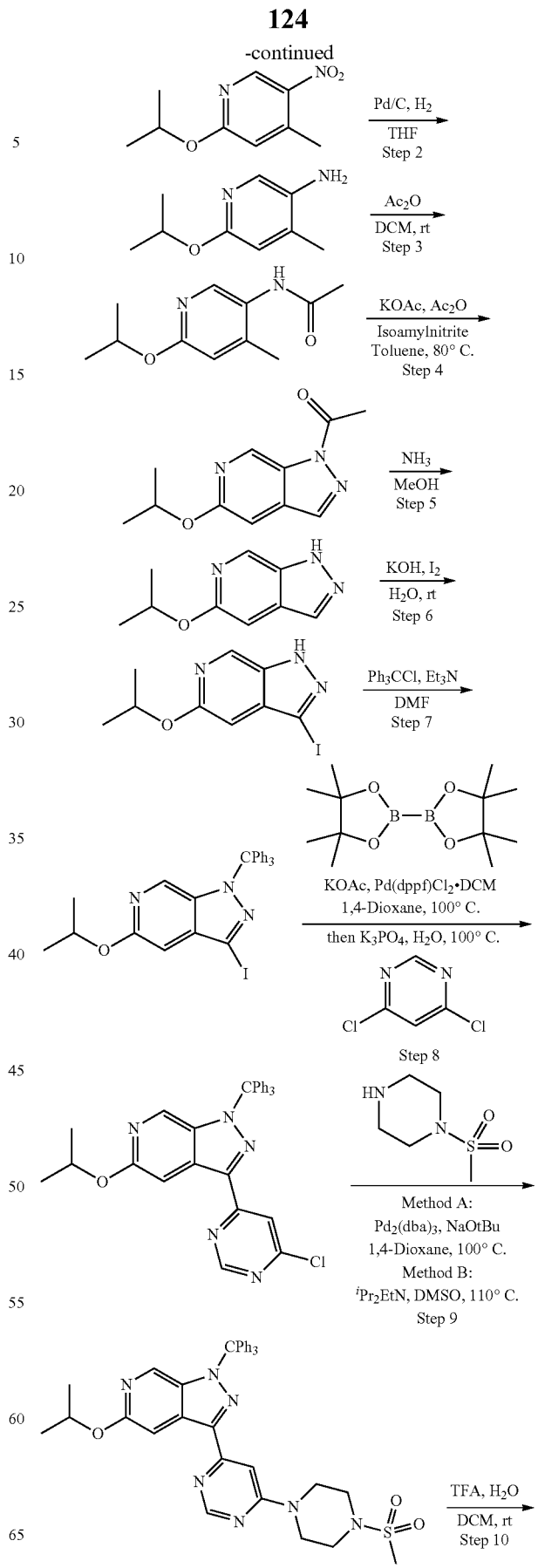

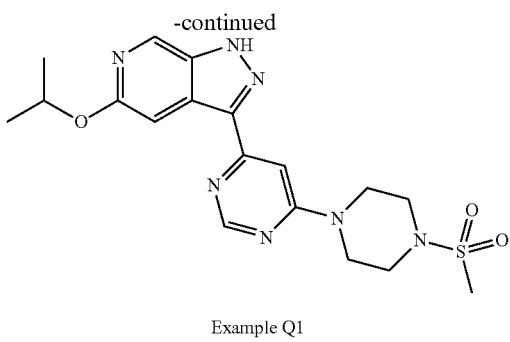

Example Q1

Step 1

A mixture of 2-hydroxy-4-methyl-5-nitropyridine (50 g, 0.325 mol), isopropyliodide (170 g, 1 mol) and Ag$_2$CO$_3$ (105 g, 0.38 mol) in toluene (1.2 L) was stirred at 60° C. for 18 h. After being cooled to room temperature, the mixture was filtered through a pad of celite. The filtrate was concentrated under reduced pressure to leave a residue which was purified by column chromatography on silica (elution with 80:1 petroleum ether:EtOAc) to provide the desired isopropoxy ether.

Step 2

To a solution of above isopropoxy ether (60 g, 0.306 mol) in THF (600 mL) was added Pd/C (16 g). The flask was evacuated and back-filled with H$_2$ (×3). The mixture was stirred under H$_2$ (40 psi) at room temperature for 20 h. The reaction mixture was filtered and filtrate was concentrated under reduced pressure to afford the desired amino compound as a dark oil, which was used directly in the next step without further purification.

Step 3

To a solution of above amino compound (100 g, 0.6 mol) in anhydrous CH$_2$Cl$_2$ (1.2 L) was added Ac$_2$O (80 mL, 0.84 mol) and the mixture was stirred at room temperature overnight. The reaction was concentrated under reduced pressure to leave a residue which was purified by column chromatography on silica (elution with 1:1 petroleum ether:EtOAc) to afford the acetamide.

Step 4

To a solution of acetamide from step 3 (80 g, 0.385 mol) in anhydrous toluene (2 L) were added KOAc (56 g, 0.571 mol) and Ac$_2$O (180 g, 1.764 mol) under N$_2$. The mixture was heated to 80° C. when isoamyl nitrite (180 g, 1.54 mol) was added dropwise and the resulting mixture was stirred at 80-100° C. overnight. After being cooled to room temperature, the reaction mixture was filtered through a pad of celite. The filtrate was concentrated under reduced pressure to leave a residue which was purified by column chromatography on silica (elution with 60:1 petroleum ether:EtOAc) to afford the desired product.

Step 5

The Compound from step 4 (145 g, 0.662 mol) was dissolved in a saturated solution of NH$_3$ in MeOH. The solution was stirred at room temperature for 2 h. The reaction mixture was concentrated under reduced pressure to leave a residue which was purified by column chromatography on silica (elution with 4:1 petroleum ether:EtOAc) to provide the desired aza-indazole.

Step 6

The above aza-indazole (57 g, 0.322 mol) was dissolved in aqueous solution of KOH (280 g, 5 mol) in H$_2$O (1.2 L). Iodine (160 g, 0.63 mol) was added dropwise to the above solution followed by stirring at room temperature for 5 h. The mixture was partitioned between EtOAc and H$_2$O. The organic phase was separated and further washed with H$_2$O, dried over Na$_2$SO$_4$, filtered and concentrated to leave a residue which was purified by column chromatography on silica (elution with 3:1 petroleum ether:EtOAc) to afford the desired 3-iodoazaindazole.

Step 7

To a cold (0° C.), stirred mixture of iodoazaindazole from step 6 (85 g, 0.28 mol) and Et$_3$N (113 g, 1.12 mol) in DMF (850 mL) was added TrCl (116.8 g, 0.42 mol) portionwise. The resulting mixture was stirred at room temperature for 3 h. The reaction mixture was poured into H$_2$O (850 mL) and the solid was filtered. The solid was then dissolved in CH$_2$Cl$_2$ and the organic layer was washed with H$_2$O (×3) and brine, dried over Na$_2$SO$_4$, filtered and concentrated to leave a residue which was washed with EtOAc (×3) to furnish trityl-protected aza-indazole as a white solid. LCMS: 546.1 [M+1]$^+$ Step 8

To a stirred solution of 3-iodoazaindazole from step 7 (200 mg, 0.367 mmol) in 1,4-Dioxane (4 mL) were added bis(pinacolato)diboron (121 mg, 0.477 mmol), KOAc (108 mg, 1.100 mmol) and Pd(dppf)Cl$_2$.DCM (14.97 mg, 0.018 mmol) followed by bubbling Ar through the solution for 15 min. The mixture was then heated to 100° C. for 10 h. The reaction was cooled to room temperature. To this mixture were then added 4,6-dichloropyrimidine (109 mg, 0.733 mmol), K$_3$PO$_4$ (234 mg, 1.100 mmol) and Pd(dppf)Cl$_2$.DCM (14.97 mg, 0.018 mmol) and water (0.4 mL). The mixture was degassed by bubbling Ar for 15 min. Then the mixture was heated at 80° C. for 8 h. After being cooled to room temperature, the reaction was concentrated under reduced pressure to leave a residue which was purified by column chromatography on silica (elution with 10:1 hexane: EtOAc) to afford the chloropyrimidine adduct.

Step 9

Method A: To a stirred solution of above chloropyrimidine (60 mg, 0.113 mmol) in 1,4-dioxane (1.4 mL) were added 1-(methylsulfonyl)piperazine (27.8 mg, 0.169 mmol), NaO$^t$Bu (32.5 mg, 0.338 mmol) and 1,3-bis(2,6-diisopropylphenyl)-imidazolidium chloride (9.63 mg, 0.023 mmol). The mixture was then purged with Ar for 15 min followed by the addition of Pd$_2$(dba)$_3$ (10.33 mg, 0.011 mmol). The reaction mixture was stirred at 100° C. overnight. After being cooled to room temperature, the reaction was concentrated under reduced pressure to leave a residue which was purified by column chromatography on silica (elution with 5:1 to 2:1 hexane:EtOAc) to afford the desired piperazine adduct. LCMS: 659.2 [M+H]$^+$ Method B: A mixture of chloropyrimidine (110 mg, 0.207 mmol), 1-(methylsulfonyl)piperazine (170 mg, 1.036 mmol) and $^i$Pr$_2$EtN (0.145 mL, 0.829 mmol) in DMSO (1 mL) was heated in a sealed tube at 110° C. overnight. After being cooled to room temperature, the mixture was diluted with EtOAc and the resulting layer was washed with water (×2). The organic layer was then dried, filtered and concentrated under reduced pressure to leave a residue which was purified by column chromatography on silica to yield the desired product.

Step 10

To a stirred solution of above piperazine adduct (40 mg, 0.061 mmol) in DCM (3 mL) and water (0.3 mL) was added TFA (1.5 mL) at room temperature. The mixture was stirred at room temperature overnight. The reaction was then carefully quenched with a saturated aqueous solution of NaHCO$_3$ until pH 7. The organic layer was separated and the aqueous layer was extracted with DCM (×3). The combined organic layers were dried, filtered and concentrated under reduced pressure to leave a residue which was purified by column chromatography on silica (elution with 10:1 DCM: MeOH) to yield Example Q1.

TABLE Q1

Utilizing the appropriate amine and the method outlined in Step 9, Method A, Scheme Q, followed by Step 10 of Scheme Q, the following compounds were prepared:

| Ex | Structure | LCMS Cond. | RT (min) | m/z | IC$_{50}$ (nM) |
|---|---|---|---|---|---|
| Q2 | 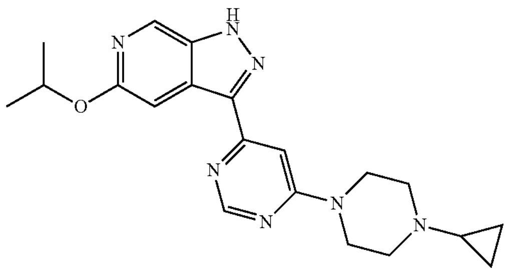 [SMILES: CC(C)Oc1cc2c(-c3cc(N4CCN(C5CC5)CC4)ncn3)n[nH]c2cn1] | A | 1.63 | 380 | 29 |

TABLE Q2

Utilizing the method outlined in Step 9, Method B, Scheme Q and the requisite amine, the following intermediates were prepared:

| Intermediate Number | Structure |
|---|---|
| Q2.1 | 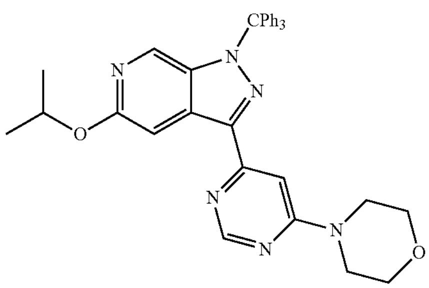 |
| Q2.2 | 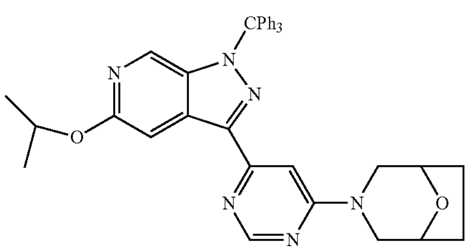 |
| Q2.3 | 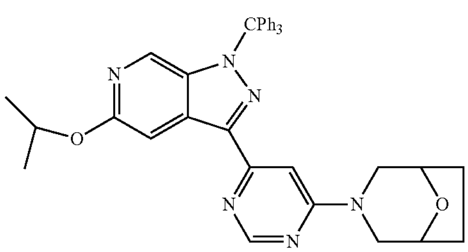 |

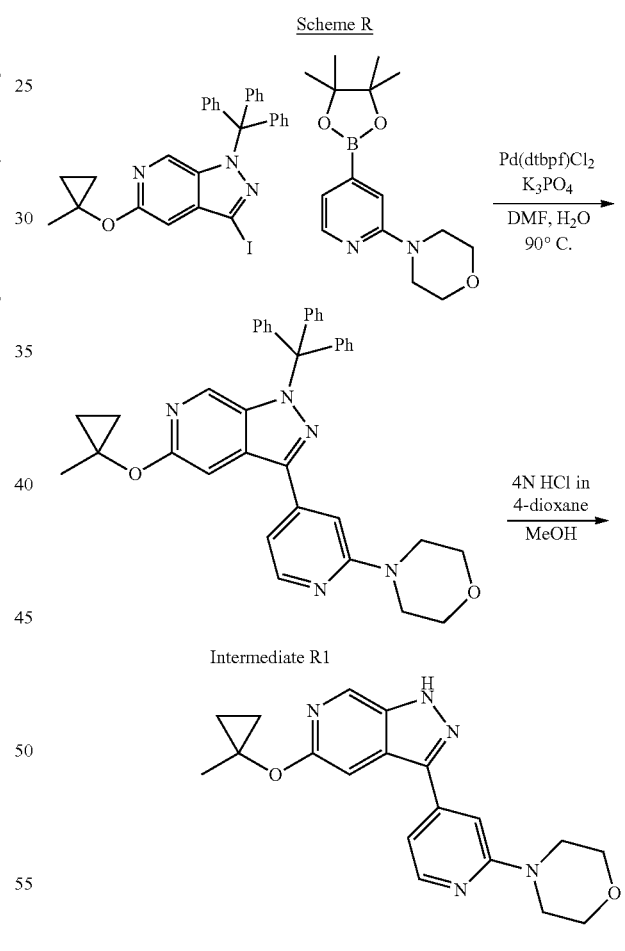

Scheme R

Intermediate R1

Example R1

Step 1

A solution of 3-Iodo-5-(1-methylcyclopropoxy)-1-trityl-1H-pyrazolo[3,4-c]pyridine (200 mg, 0.359 mmol) (0324591-0128), 4-(4-(4,4,5,5-tetramethyl-1,3,2-dioxaborolan-2-yl)pyridin-2-yl)morpholine (156 mg, 0.538 mmol) and 1,1'-bis(di-tert-butylphosphino)ferrocene palladium dichloride (11.69 mg, 0.018 mmol) in DMF (2 ml) was treated with potassium phosphate (228 mg, 1.076 mmol) in water (0.3 ml). The mixture was degassed, purged with nitrogen for 10 min, then heated at 90° C. for 3 h. The mixture was cooled, quenched with water and extracted with EtOAc (4x). The combined EtOAc layers were dried over anhydrous MgSO$_4$, filtered and evaporated. The resulting crude material was purified by MPLC on silica gel (gradient elution 0% to 30% EtOAc in hexanes) to afford Intermediate R1.

Step 2

Intermediate R1 (125 mg, 0.211 mmol) was dissolved in MeOH (5 ml) and hydrogen chloride (1.579 ml, 6.32 mmol)(4 M in dioxane) was added. The mixture was heated at 75° C. in a sealed tube for 2 h. The reaction was cooled, unsealed, diluted with EtOAc and washed with sat. NaHCO$_3$ $_{(aq.)}$. The organic layer was dried over anhydrous MgSO$_4$, filtered and evaporated. The resulting residue was purified by silica gel MPLC (gradient elution, 30% to 100% EtOAc in hexanes) to afford Example R1.

was purged with nitrogen for 5 min. The mixture was then sealed in a vial with a pressure relief cap and heated at 80° C. for 16 h.

The reaction was cooled to RT, diluted with DCM, and filtered through a pad of celite. The filtrate was concentrated to leave a residue which was purified by silica gel chromatography (gradient elution with 0% to 75% EtOAc in hexanes) to yield Intermediate S1.

Step 2

TFA (15 ml, 195 mmol) was added to a stirred, room temperature mixture of Intermediate S1 (270 mg, 0.465 mmol) in DCM (10 ml) and water (6 ml, 333 mmol) and the mixture was stirred at room temperature for 48 h. The reaction was concentrated and the residue was dissolved in MeOH and purified by reversed-phase column chromatography (Analogix 150 g SF40 C18 column), gradient eluting with 0% to 100% MeCN in water with 0.1% TFA to give Example S1.

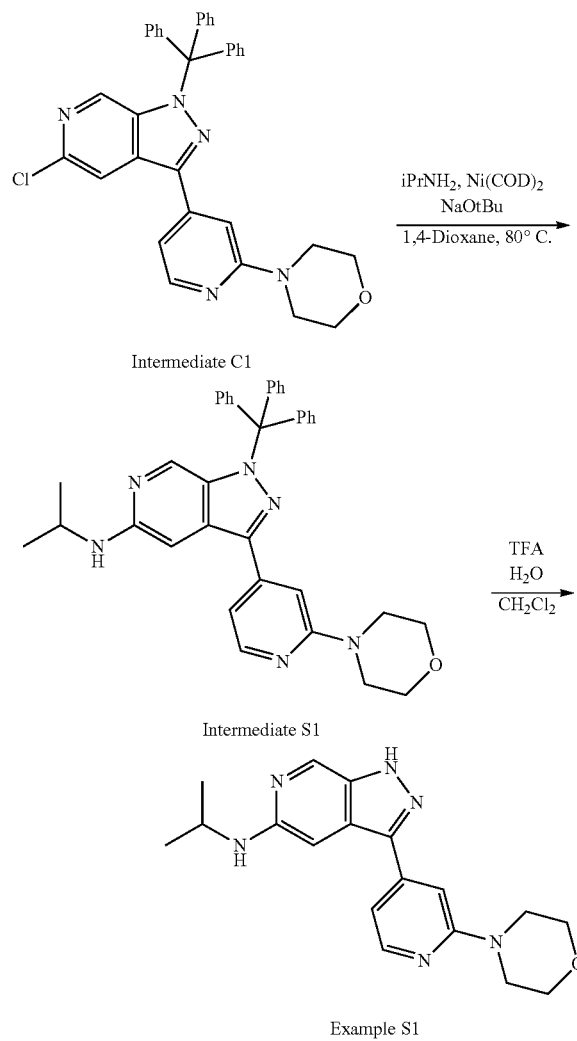

Scheme S

Intermediate C1

Intermediate S1

Example S1

Step 1

A stirred mixture of Intermediate C1 (400 mg, 0.717 mmol), isopropylamine (185 μl, 2.150 mmol), sodium tert-butoxide (310 mg, 3.23 mmol), 1,3-bis(2,6-diisopropylphenyl)-imidazolidinium-chloride (61.2 mg, 0.143 mmol) and Ni(COD)$_2$ (19.71 mg, 0.072 mmol) in 1,4-dioxane (4565 μl)

TABLE S1

Utilizing a method similar to that outlined in Scheme S and the requisite amine, the following compounds were prepared:

| Ex | Structure | Cond. | RT (min) | m/z | IC$_{50}$ (nM) |
|---|---|---|---|---|---|
| S2 | 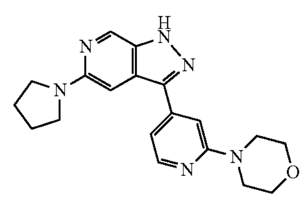 [SMILES: c1cc(-c2n[nH]c3cnc(N4CCCC4)cc23)cc(N2CCOCC2)n1] | A | 1.69 | 351 | 272 |
| S3 | 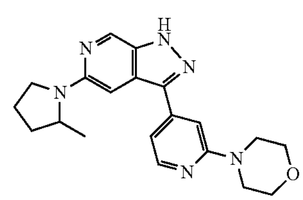 [SMILES: CC1CCCN1c1cc2c(-c3ccnc(N4CCOCC4)c3)n[nH]c2cn1] | A | 1.77 | 365 | 121 |

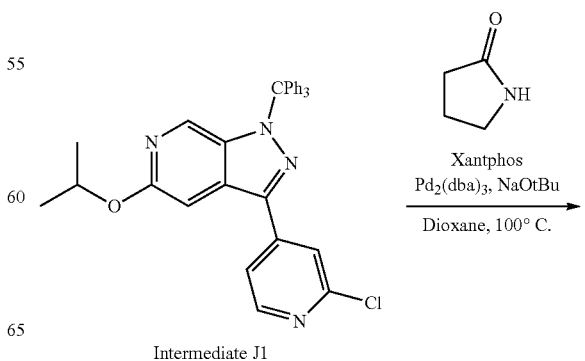

Scheme T

Intermediate J1

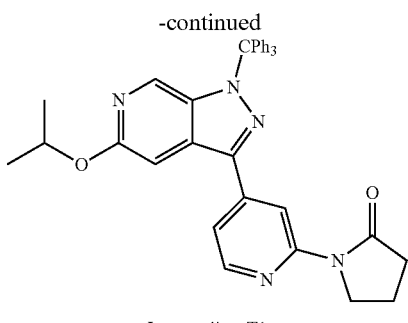

Intermediate T1

TABLE T1

Utilizing a method similar to that outlined in Scheme T and oxazolidin-2-one in place of pyrrolidin-2-one, the following compound was prepared:

| Ex | Structure | Cond. | RT (min) | m/z | IC$_{50}$ (nM) |
|---|---|---|---|---|---|
| T2 | 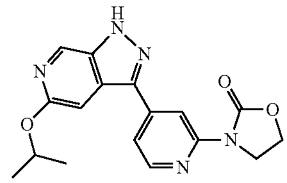 [SMILES: CC(C)Oc1cc2c(-c3ccnc(N4CCOC4=O)c3)n[nH]c2cn1] | A | 2.45 | 340 | 102 |

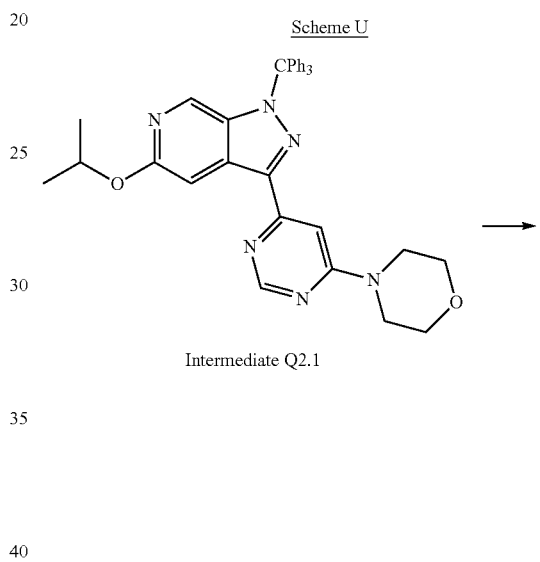

Scheme U

Intermediate Q2.1

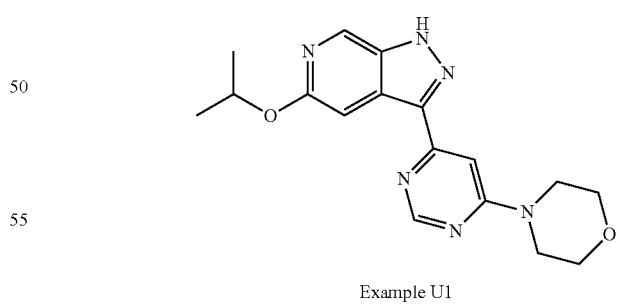

Example T1

Example U1

Step 1

Intermediate J1 (220 mg, 0.414 mmol), pyrrolidin-2-one (0.064 mL, 0.829 mmol), 4,5-bis(diphenylphosphino)-9,9-dimethylxanthene (36 mg, 0.062 mmol), cesium carbonate (472 mg, 1.45 mmol) and Pd$_2$(dba)$_3$ (19 mg, 0.021 mmol) were combined with 1,4-dioxane (1 mL) in a glass vial. The solution was purged with N$_2$, sealed and heated at 100° C. for 18 h. The reaction was cooled to room temperature and unsealed. The reaction mixture was filtered and the filtrate was concentrated. The crude residue was subjected to PTLC on silica gel using 30% EtOAc in hexanes to afford Intermediate T1.

Step 2

Utilizing a method similar to that outlined in Step 2 of Scheme S, Intermediate T1 was deprotected, then purified via PTLC on silica gel using 5% MeOH in dichloromethane to afford Example T1.

To a solution of Intermediate Q2.1 (110 mg, 0.19 mmol) in CH$_2$Cl$_2$ (10 ml) was added triethysilane (0.7 mL, 4.38 mmol) followed by TFA (1.4 mL, 18.2 mmol). The resulting mixture was stirred for 2 hours. The reaction was evaporated, and the resulting residue was purified by C18 reversed phase MPLC (30 g C18 column, gradient elution from 0% to 100% MeCN in water) to afford Example U1.

TABLE U
Utilizing a method similar to that outlined in Scheme U and the requisite trityl-protected material, the following compounds were prepared:
| Ex | Structure | Cond. | LCMS RT (min) | m/z | IC$_{50}$ (nM) |
|---|---|---|---|---|---|
| U2 | 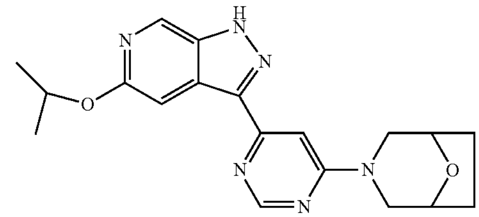 [SMILES: CC(C)Oc1cc2c(-c3cc(N4CC5CCC(C4)O5)ncn3)n[nH]c2cn1] | A | 1.95 | 367 | 194 |
| U3 | 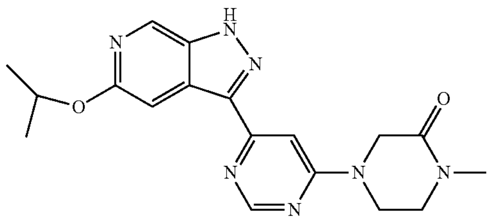 [SMILES: CC(C)Oc1cc2c(-c3cc(N4CCN(C)C(=O)C4)ncn3)n[nH]c2cn1] | A | 1.79 | 368 | 58.6 |
| U4 | 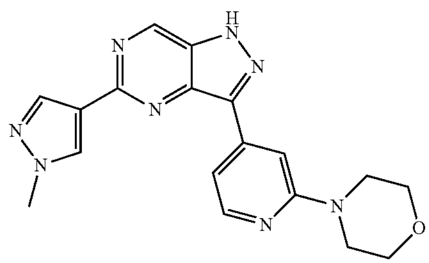 [SMILES: Cn1cc(-c2ncc3[nH]nc(-c4ccnc(N5CCOCC5)c4)c3n2)cn1] | A | 1.764 | 363 | 27.72 |
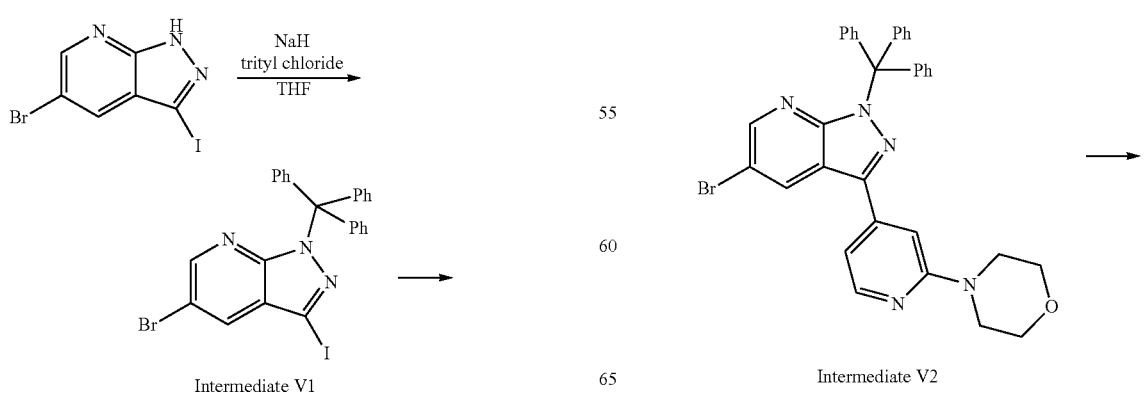
Scheme V -continued

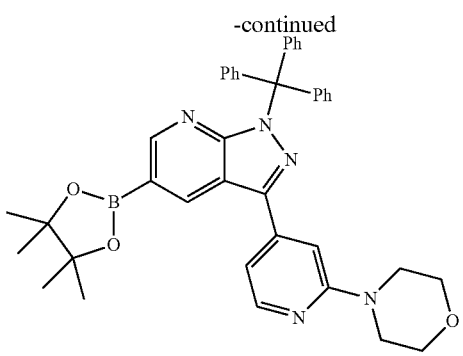

Intermediate V3

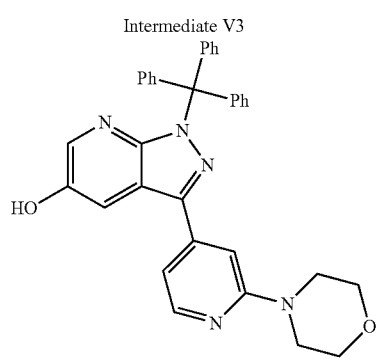

Intermediate V4

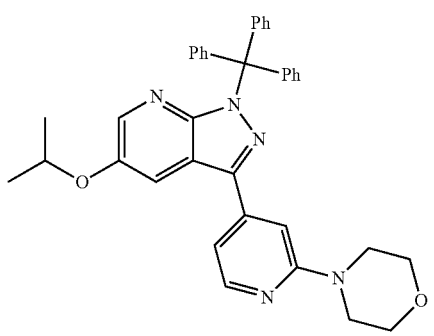

Intermediate V5

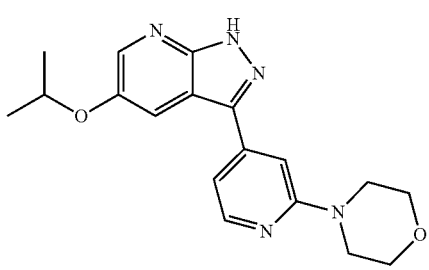

Example V1

Step 1

A solution of 5-bromo-3-iodo-1H-pyrazolo[3,4-b]pyridine (7.5 g, 23.2 mmol) in THF (80 mL) was cooled to 0° C. and then treated with NaH (60% suspension in mineral oil, 1.3 g, 32.4 mmol) in 5 portions. The mixture was stirred for 10 min. Trityl chloride (7.75 g, 27.8 mmol) was added and the resulting mixture was allowed to warm to RT slowly. The reaction was stirred overnight at room temperature. The reaction was partitioned between ethyl acetate and brine. The layers were separated and the organic layer was dried, filtered and evaporated. The crude residue was purified by silica column chromatography to afford Intermediate V1. Additional product was isolated from the column by flushing with methanol in dichloromethane.

Step 2

Intermediate V1 (2.5 g, 4.42 mmol), (2-morpholinopyridin-4-yl)boronic acid (1.10 g, 5.30 mmol) and 2M $K_3PO_{4\ (aq.)}$ (6.62 mL, 13.25 mmol) were stirred in 50 ml of DME and purged with nitrogen for 10 min. Then 1,1'-bis(diphenylphosphino)ferrocene-palladium(II)dichloride dichloromethane complex (361 mg, 0.442 mmol) was added and the mixture was heated at 90° C. for 17 hours. The reaction was cooled to room temperature and diluted with EtOAc. The resulting solution was filtered through Celite. The filtrate was evaporated and the resulting residue was purified by silica gel chromatography (80 g, column, gradient elution with hexane 100% to 50% ethylacetate/hexane over 30 min) to afford Intermediate V2.

Step 3

A solution of Intermediate V2 (1.11 g, 1.84 mmol) in 11 ml of 1,4-dioxane was degassed with $N_2$ for 5 min. To this solution was added bis(pinacolato)diboron (982 mg, 3.87 mmol), potassium acetate (1.09 g, 11.05 mmol) and 1,1'-bis(diphenylphosphino)ferrocene-palladium(II)dichloride dichloromethane complex (451 mg, 0.553 mmol). The resulting mixture was heated at 110° C. in a sealed vial for 1.5 hours. The reaction was cooled, unsealed and diluted with EtOAc. The mixture was filtered through a pad of silica gel and the filtrate was evaporated to afford a crude residue. The resulting residue was purified by silica gel column chromatography to afford Intermediate V3.

Step 4

Acetic acid (0.49 ml, 8.54 mmol) was added to a solution of Intermediate V4 (1.11 g, 1.71 mmol) in THF (7 ml). Hydrogen peroxide (30% aqueous, 1.013 g, 8.94 mmol) was added and the reaction was stirred at room temperature for 4 h. Triethylamine (1.19 ml, 8.54 mmol) was added and the resulting mixture was stirred for 45 min. The mixture was evaporated and the resulting residue was purified by silica gel column chromatography (MPLC, 24 gram silica) to afford Intermediate V4.

Step 5

A combination of Intermediate V4 (300 mg, 0.56 mmol), cesium carbonate (453 mg, 1.39 mmol) and 2-iodopropane (425 mg, 2.50 mmol) in DMF (2 mL) was stirred for 36 h at room temperature. The mixture was then partitioned between EtOAc and brine. The layers were separated and the organic layer was washed twice with brine, dried and concentrated. The resulting residue was subjected to silica gel chromatography to afford Intermediate V5.

Step 6

Trifluoroacetic acid (7 mL) was added to a solution of Intermediate V5 (284 mg, 0.488 mmol) in $CH_2Cl_2$ (7 mL). The reaction was stirred overnight. Trifluoroacetic acid (3 mL) was added and the reaction was stirred for 4 h more. The reaction was concentrated in vacuo. The residue was partitioned between $CH_2Cl_2$ and saturated aqueous $NaHCO_3$. The organic layer was dried and subjected to silica gel chromatography (gradient elution, 0% to 10% MeOH in $CH_2Cl_2$) to afford Example V1.

Scheme W

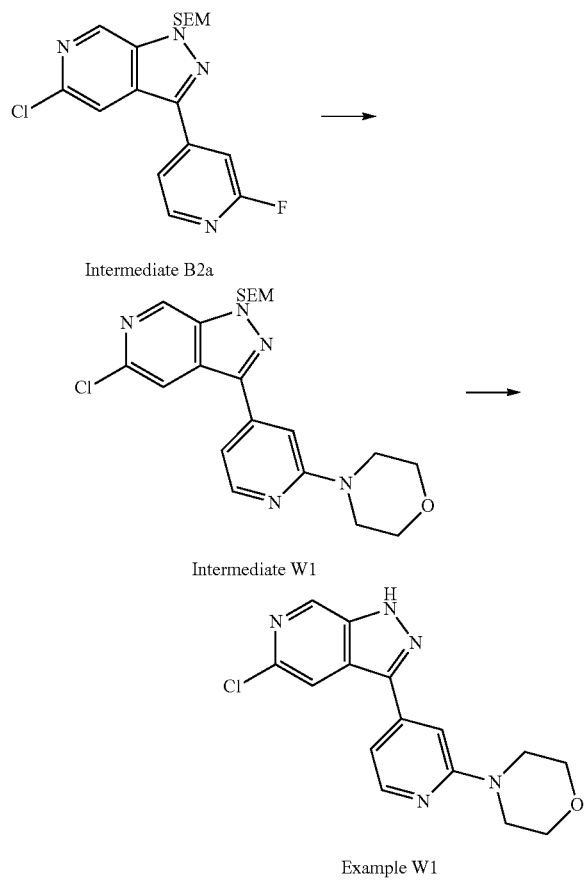

Intermediate B2a

Intermediate W1

Example W1

Step 1

A solution of Intermediate B2a (150 mg, 0.396 mmol) in morpholine (0.8 mL) was sealed in a reaction vessel and heated at 160° C. for 2 h. The reaction was then cooled, unsealed and partitioned between dichloromethane and water. The layers were separated and the organic layer was concentrated to yield a residue, which was subjected to silica gel chromatography (gradient elution, 0% to 3% MeOH in $CH_2Cl_2$) to afford Intermediate W1.

Step 2

A solution of Intermediate W1 (30 mg, 0.067 mmol) in $CH_2Cl_2$ (0.67 mL) was treated with TFA (0.25 mL) and stirred overnight at room temperature. The reaction was quenched with 10% $Na_2CO_3$ $_{(aq.)}$ and was then treated with conc. ammonium hydroxide. After stirring for 10 min, the mixture was extracted with $CH_2Cl_2$. The organic layer was concentrated and subjected to silica gel chromatography (gradient elution, 0% to 5% MeOH in $CH_2Cl_2$) to afford Example W1.

TABLE W1

Utilizing a method similar to that described in Step 1 of Scheme W and the appropriate starting material, the following intermediates were prepared:

| Starting Material | Intermediate Number | Intermediate Structure |
|---|---|---|
| [structure with SEM, pyridine, F] | Intermediate W1.1 | [structure with SEM, pyridine, morpholine] |
| [structure with SEM, pyridine, F] | Intermediate W1.2 | [structure with SEM, pyridine, morpholine] |

Scheme X

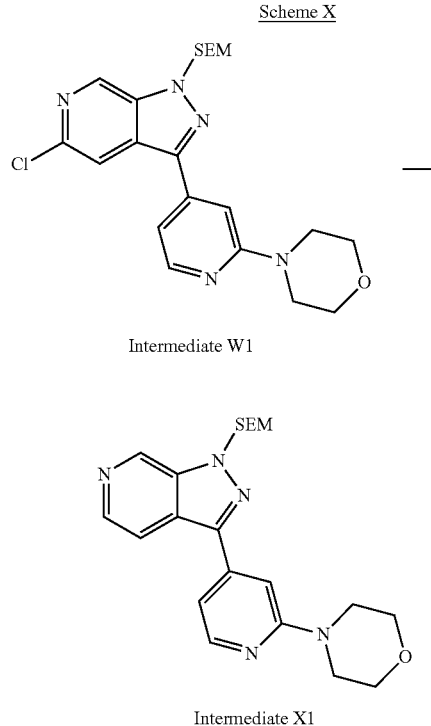

Intermediate W1

Intermediate X1

Example X1

Step 1

Intermediate W1 (150 mg, 0.34 mmol) was dissolved in MeOH (3.4 mL) and palladium on carbon (20 mg) was added. The reaction mixture was purged with hydrogen and a balloon filled with hydrogen was affixed to the top of the flask. The reaction was stirred overnight. The reaction was filtered through Celite and the filter pad was washed with MeOH. The combined filtrates were concentrated and the resulting residue was subjected to silica gel MPLC (gradient elution 0% to 10% MeOH in $CH_2Cl_2$) to afford Intermediate X1.

Step 2

A solution of Intermediate X1 (90 mg, 0.219 mmol) in $CH_2Cl_2$ (1.64 mL) was treated with TFA (0.55 mL) and stirred overnight at room temperature. The reaction was concentrated in vacuo. The resulting residue was dissolved in MeOH (2 mL) and was treated with conc. ammonium hydroxide. (1 mL). After stirring for 1 h, the methanol was evaporated off in vacuo and the remaining aqueous layer was extracted with $CH_2Cl_2$. The organic layer was concentrated and subjected to silica gel chromatography (gradient elution, 0% to 5% MeOH in $CH_2Cl_2$) to afford Example X1.

TABLE X1

Utilizing a method similar to that described in Scheme X, Step 2 and the appropriate SEM-protected Intermediate, the following examples were prepared:

| Ex | Structure | LCMS Cond. | RT (min) | m/z | $IC_{50}$ (nM) |
|---|---|---|---|---|---|
| X2 | (structure) | B | 0.8 | 282 | 220 |
| X3 | (structure) | B | 0.91 | 282 | 73 |

Scheme Y

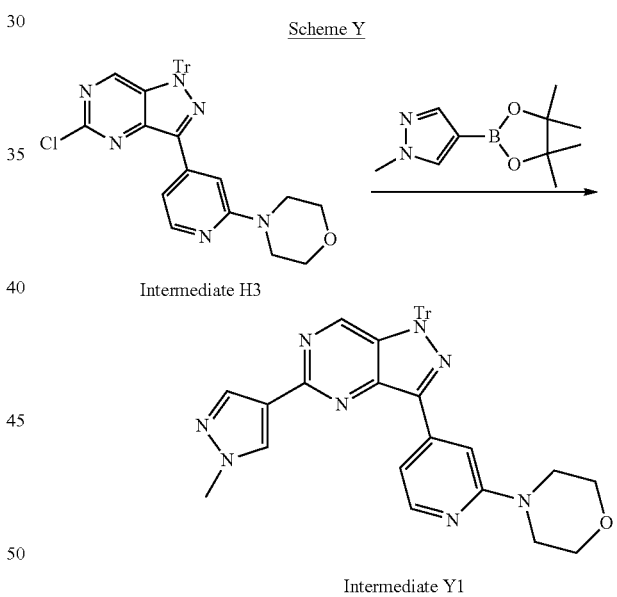

Intermediate H3

Intermediate Y1

To a degassed solution of Intermediate H3 (70 mg, 0.125 mmol), 1-methyl-4-(4,4,5,5-tetramethyl-1,3,2-dioxaborolan-2-yl)-1H-pyrazole (52.1 mg, 0.250 mmol) and chloro(2-dicyclohexylphosphino-2',4',6'-triisopropyl-1,1'-biphenyl)[2-(2-aminoethyl)phenyl)]palladium(II) MTBE adduct (10.35 mg, 0.013 mmol) in DMA (5 mL) at rt, was added degassed 2M aqueous potassium phosphate tribasic (0.125 mL, 0.250 mmol). The reaction was capped and heated at 80° C. for 30 min. The reaction was then cooled down and partitioned between EtOAc and water. The layers were separated and the organic layer was concentrated. The resulting residue was purified via silica gel chromatography [ISCO MPLC, gradient elution, 0%-10% MeOH (with 2N $NH_3$) in DCM] which furnished Intermediate Y1.

Scheme Z

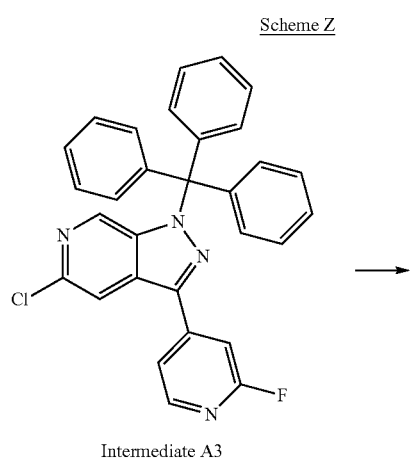

Intermediate A3

Example Z1

A mixture of Intermediate A3 (350 mg, 0.713 mmol), imidazole (243 mg, 3.56 mmol) and cesium carbonate (2323 mg, 7.13 mmol) in DMF (2 mL) was heated at 150° C. ON. The reaction was cooled to room temperature, diluted with DCM, filtered through Celite, then concentrated. The residue was purified via reversed-phased C18 MPLC [ISCO, gradient elution, 0%-100% water (TFA) in acetonitrile (TFA)] which furnished Example Z1.

Scheme AA

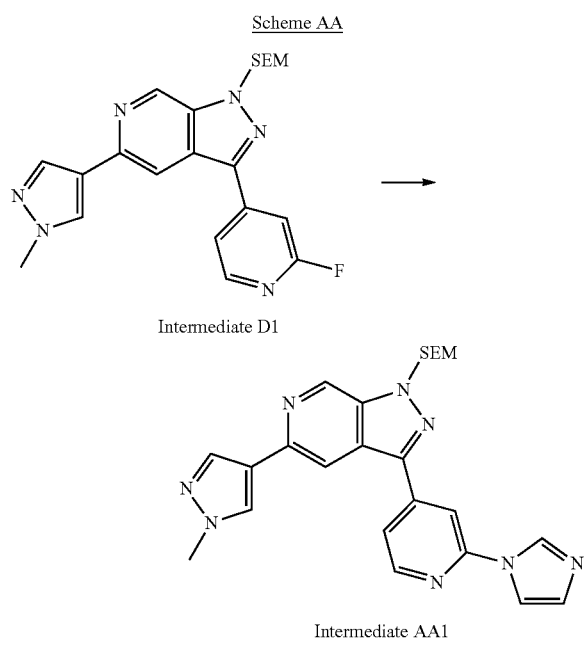 [SMILES: Cn1cc(-c2cc3c(-c4ccnc(F)c4)nn(COCC[Si](C)(C)C)c3cn2)cn1 ; Cn1cc(-c2cc3c(-c4ccnc(-n5ccnc5)c4)nn(COCC[Si](C)(C)C)c3cn2)cn1]

Intermediate D1

Intermediate AA1

Utilizing a method similar to that described in Scheme Z, and substituting Intermediate D1 for Intermediate A3, Intermediate AA1 was prepared.

Scheme AB

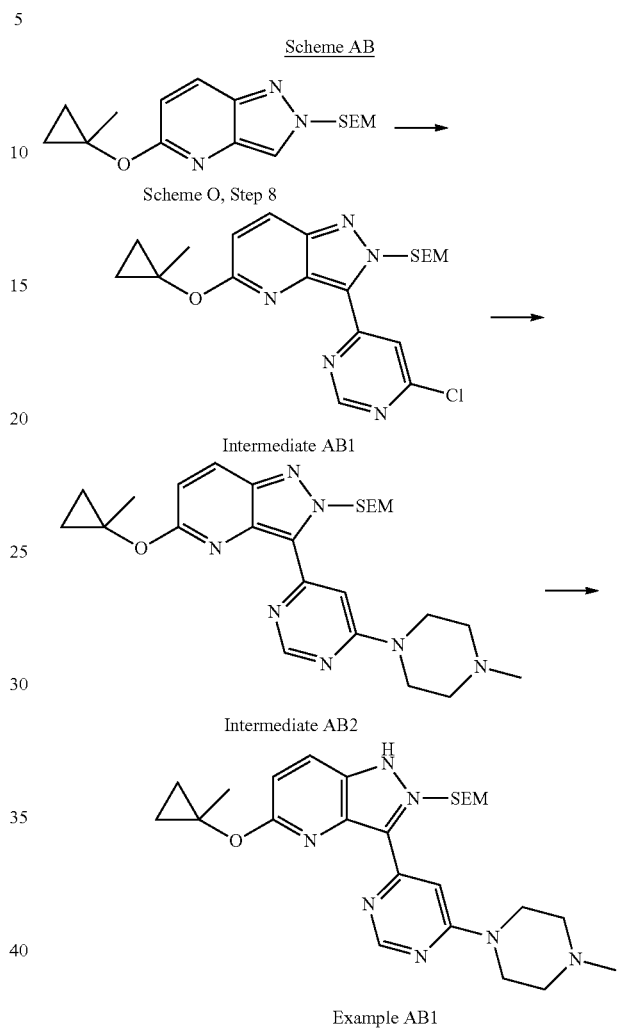

Scheme O, Step 8

Intermediate AB1

Intermediate AB2

Example AB1

Step 1

A solution of the intermediate prepared in Step 8 of Scheme O (500 mg, 1.565 mmol) in THF (3.1 mL) was cooled to −78° C. using a dry ice/acetone bath. A solution of 1.6M n-butyllithium (1272 μl, 2.035 mmol) in hexanes was added. The resulting mixture was stirred at −78° C. for 15 min and then raised to −20° C. for 5 min. The mixture was then cooled to −78° C. and a solution of 0.5 M zinc chloride in THF (4695 μl, 2.348 mmol, freshly prepared from fused zinc chloride) was added. The mixture was raised to −20° C. and stirred for 10 min. The solution turned red/brown in color. A mixture of freshly sublimed 4,6-dichloropyrimidine (350 mg, 2.348 mmol) and tetrakis(triphenylphosphine)palladium(0) (90 mg, 0.078 mmol) were added. The cold bath was removed and the mixture was stirred at room temperature for 20 h. The reaction mixture was quenched using saturated aqueous $NH_4Cl$ and extracted with DCM (×3). The organic layers were combined, dried over anhydrous $MgSO_4$, filtered, and concentrated. The crude residue was subjected to silica gel chromatography (gradient elution, 0% to 25% EtOAc in hexanes) to afford Intermediate AB1.

Step 2

Intermediate AB1 (30 mg, 0.069 mmol) was dissolved in DMSO (0.46 mL) and triethylamine (48.4 µl, 0.347 mmol) and 1-methylpiperazine (12.34 µl, 0.111 mmol) were added. The reaction was sealed in a vial and heated at 100° C. for 22 h. The reaction was cooled to room temperature and unsealed. The reaction was partitioned between EtOAc and water. The layers were separated and the aqueous layer was extracted twice with EtOAc. The combined organic layers were washed with brine, dried over anhydrous MgSO$_4$, filtered, and concentrated to afford Intermediate AB2, which was used in the next step without further purification.

Step 3

Utilizing a method similar to that outlined in Step 10 of Scheme O, Intermediate AB2 was converted to Example AB1.

Scheme AC

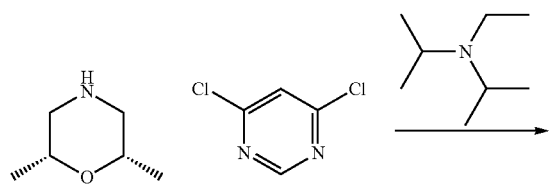

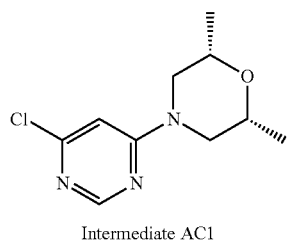

Intermediate AC1

A solution of 4,6-dichloropyrimidine (750 mg, 5.03 mmol) in t-BuOH (10.1 mL) was treated with cis-2,6-dimethylmorpholine (609 mg, 5.29 mmol). The reaction mixture was cooled to 0° C. using an ice bath. Hunig's Base (1.055 mL, 6.04 mmol) was added. The reaction was slowly warmed to room temperature. The reaction was then heated at 80° C. for 16 h. The reaction was then cooled to room temperature. The mixture was concentrated and the resulting residue was subjected to silica gel chromatography (ISCO MPLC, 40 g silica column, gradient elution, 0% to 40% EtOAc in hexanes to afford Intermediate AC1.

TABLE AD

LRRK2 Km LanthaScreen™ results and LCMS data for analogs prepared are listed below.

| Ex | Structure | LCMS Cond. | RT (min) | m/z | IC$_{50}$ (nM) |
|---|---|---|---|---|---|
| W1 | 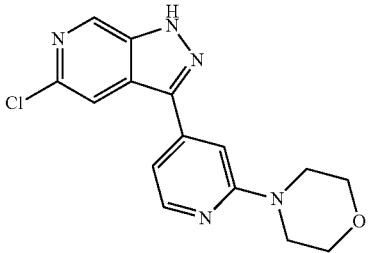 [SMILES: Clc1cc2c(-c3ccnc(N4CCOCC4)c3)n[nH]c2cn1] | B | 1.36 | 316 | 58 |
| X1 | 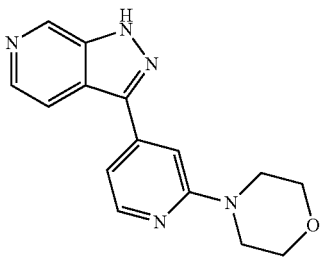 [SMILES: c1cc2c(-c3ccnc(N4CCOCC4)c3)n[nH]c2cn1] | B | 0.81 | 282 | 42 |
| B1 | 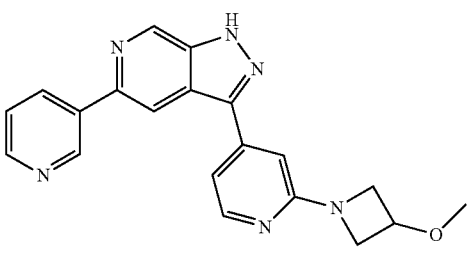 [SMILES: COC1CN(c2cc(-c3n[nH]c4cnc(-c5cccnc5)cc34)ccn2)C1] | A | 1.66 | 359 | 7.3 |

TABLE AD-continued

LRRK2 Km LanthaScreen ™ results and LCMS data for analogs prepared are listed below.

| Ex | Structure | Cond. | LCMS RT (min) | m/z | IC$_{50}$ (nM) |
|----|-----------|-------|---------------|-----|----------------|
| F1 | 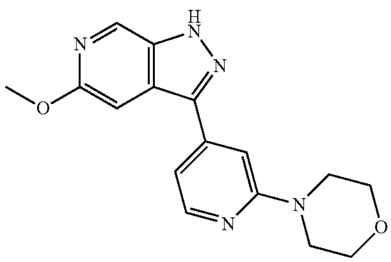 [SMILES: COc1cc2c(-c3ccnc(N4CCOCC4)c3)n[nH]c2cn1] | A | 1.78 | 312 | 52.46 |
| A1 | 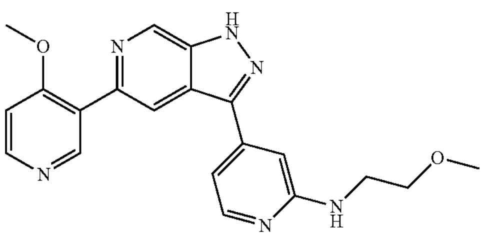 [SMILES: COCCNc1cc(-c2n[nH]c3cnc(-c4cnccc4OC)cc23)ccn1] | A | 1.67 | 377 | 0.60 |
| C1 | 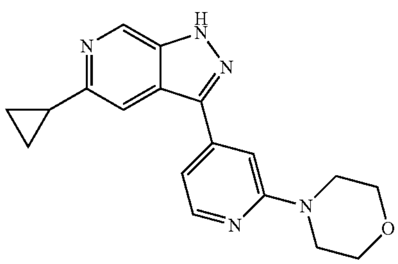 [SMILES: c1cc(-c2n[nH]c3cnc(C4CC4)cc23)cc(N2CCOCC2)n1] | A | 1.62 | 322 | 53 |
| Z1 | 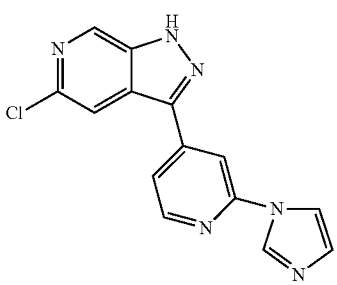 [SMILES: Clc1cc2c(-c3ccnc(-n4ccnc4)c3)n[nH]c2cn1] | A | 1.75 | 297 | 1085 |
| S1 | 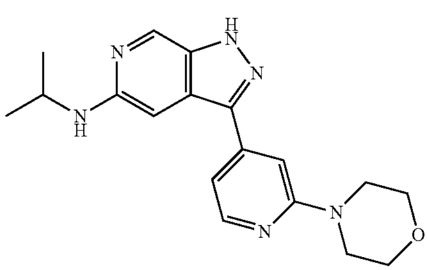 [SMILES: CC(C)Nc1cc2c(-c3ccnc(N4CCOCC4)c3)n[nH]c2cn1] | A | 1.66 | 339 | 81 |

TABLE AD-continued

LRRK2 Km LanthaScreen™ results and LCMS data for analogs prepared are listed below.

| Ex | Structure | Cond. | RT (min) | m/z | IC$_{50}$ (nM) |
|---|---|---|---|---|---|
| E1 | | A | 1.62 | 399 | 97.82 |
| T1 | | A | 2.40 | 338 | 87 |
| Q1 | | A | 1.91 | 418 | 54.4 |
| U1 | | A | 1.90 | 341 | 76 |
| R1 | | C | 0.99 | 352 | 1.56 |

TABLE AD-continued

LRRK2 Km LanthaScreen™ results and LCMS data for analogs prepared are listed below.

| Ex | Structure | Cond. | LCMS RT (min) | m/z | IC$_{50}$ (nM) |
|---|---|---|---|---|---|
| P1 | 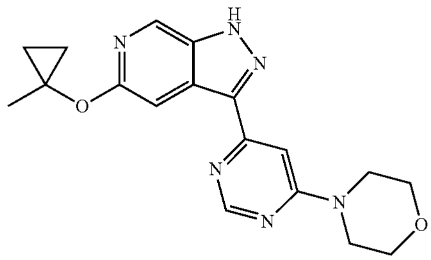 [SMILES: CC1(Oc2cc3c(-c4cc(N5CCOCC5)ncn4)n[nH]c3cn2)CC1] | E | 0.78 | 353 | 2.1 |
| V1 | 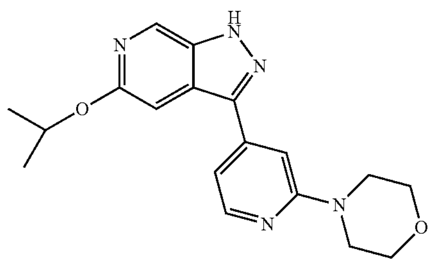 [SMILES: CC(C)Oc1cc2c(-c3ccnc(N4CCOCC4)c3)n[nH]c2cn1] | A | 1.82 | 340 | 15.5 |
| AB1 | 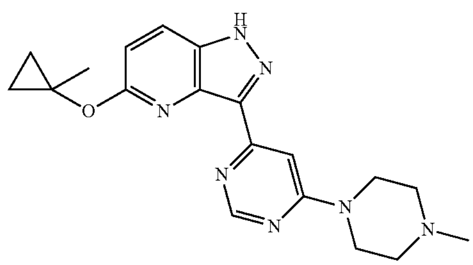 [SMILES: CN1CCN(c2cc(-c3n[nH]c4ccc(OC5(C)CC5)nc34)ncn2)CC1] | G | 0.78 | 366 | 593 |
| O1 | 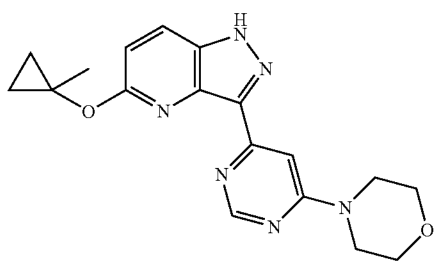 [SMILES: CC1(Oc2ccc3[nH]nc(-c4cc(N5CCOCC5)ncn4)c3n2)CC1] | G | 0.81 | 353 | 313 |

LCMS Conditions

Condition A: Agilent 6140 Quadruple Easy Access LC/MS; Column: Agilent Zorbax SB-C18, 3.0×50 mm, 1.8 μm; Solvent A: Water with 0.1% TFA; Solvent B: acetonitrile with 0.1% TFA; Flow Rate: 1 mL/min; Dual wavelength UV Detection at 220 nm and 254 nm; Gradient: 10% Solvent B to 95% Solvent B over 1.5 min., isocratic at 95% Solvent B for 1.2 min., gradient to 10% Solvent B over 0.1 min., isocratic at 10% Solvent B for 0.8 min.

Method B: Mobile Phase: A: 95% water, 5% ACN (0.05% TFA); B: ACN (0.05% TFA); Gradient: 94:6 to 2:98 (A:B) over 3.65 min; 2:98 (A:B) for 0.3 min; 2:98 to 94:6 (A:B) over 0.03 min; 94:6 (A:B) 0.02 min. Flow rate: 1.0 ml/min; Column: YMC pro C18 (2.0×20 mm, 5 μM)

Condition C: Column: SUPELCO Ascentis Express C18, 3×50 mm, 2.7 um, Mobile phase: A: Water (0.05% TFA) B: Acetonitrile (0.05% TFA), UV: 200-400 nm

| [Gradient Table] | | | |
|---|---|---|---|
| Time(min) | Flow Rate | % A | % B |
| Initial | 1.25 | 90 | 10 |
| 0.8 | 1.25 | 1 | 99 |
| 1.99 | 1.25 | 1 | 99 |
| 2.00 | 1.25 | 90 | 10 |

Condition D: Waters Acquity UPLC/MS, Electrospray positive ion mode; Column: Waters Acquity UPLC BEH C18, 2.1×50 mm, 1.7 micron; Gradient elution 5:95 to 100:0

MeCN (0.1% NH$_4$OH): water (0.1% NH$_4$OH) over 1.4 min 0.8 mL/min; UV: 220 nm.

Condition E: Reverse HPLC on a 19×100 mm, Waters XBridge C18 column, 5μ particle size, linear gradient, standard 17% ACN/H$_2$O to 52% ACN/H$_2$O buffering with 0.16% Ammonium Hydroxide @ flow rate 50 mL/min over 5.0 min Condition F: Reverse HPLC on a 19×100 mm, Waters XBridge C18 column, 5μ particle size, linear gradient, standard 7% ACN/H$_2$O to 42% ACN/H$_2$O buffering with 0.16% Ammonium Hydroxide @ flow rate 50 mL/min over 5.0 min Condition G: Reverse HPLC on a 19×100 mm, Waters XBridge C18 column, 4 L particle size, linear gradient, standard 10% ACN/H$_2$O to 45% ACN/H$_2$O buffering with 0.16% Ammonium Hydroxide @ flow rate 50 mL/min over 5.0 min Biological Assays The data presented for the Km ATP LanthaScreen™ Assay represents mean IC$_{50}$ values based on several test results and may have reasonable deviations depending on the specific conditions and reagents used. Reagents for the LRRK2 Km ATP LanthaScreen™ Assay were purchased from Life Technologies Corporation.

LRRK2 Km ATP LanthaScreen™ Assay a) 400 nl of a 1:2.15 serial dilution of test compound (98 μM top assay concentration) is spotted via Labcyte Echo to certain wells in a 384 well black, untreated plate. Control wells contain 400 nl of either DMSO or 400 nl of a known inhibitor in DMSO.

b) 10 μl of a 2.5 nM LRRK2 (G2019S mutation, GST-LRRK2 (amino acids 970-2527)) enzyme solution in 1× assay buffer (50 mM Tris pH 8.5, 10 mM MgCl$_2$, 0.01% Brij-35, 1 mM EGTA, 2 mM DTT, 0.05 mM NaVO$_4$) is added to all wells.

c) A 30 minute room temperature incubation is followed by addition of 10 μl of 800 nM fluorescein labeled LRRKtide peptide substrate and 186 μM ATP solution in 1× assay buffer to all wells.

d) After a 60 minute room temperature incubation, 20 μl of TR-FRET Dilution Buffer (Invitrogen PV3756B) containing 4 nM Tb-labeled anti-phospho LRRKtide antibody and 20 mM EDTA is added to all wells.

e) Plates are incubated at room temperature for 1 hour and read on an Envision™ multi-mode plate reader with LanthaScreen™ settings. Results are analysed using Assay Data Analyzer.

What is claimed:

1. A compound of the formula: I:

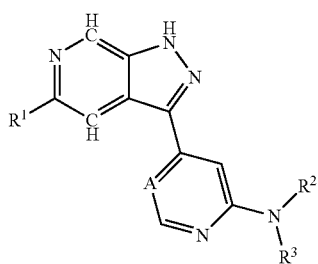

wherein R$^1$ is selected from the group consisting of:
a) hydrogen,
b) halo,
c) cyano,
d) hydroxyl,
e) C$_{2-6}$ alkenyl, which is optionally substituted with one to three substitutents independently selected from the group consisting of halo, cyano and R$^5$;
f) OC$_{2-6}$ alkenyl, which is optionally substituted with one to three substitutents independently selected from the group consisting of halo, cyano and R$^5$;
g) R$^5$,
h) OR$^5$,
i) aryl, wherein said aryl is optionally substituted with one to three substituents independently selected from the group consisting of:
  halo,
  cyano,
  hydroxyl,
  oxo,
  C$_{1-3}$ alkyl, which is optionally substituted with one to four substituents independently selected from the group consisting of hydroxyl, halo, cyano, heterocyclyl, OC$_{1-3}$ alkyl and NR$^c$R$^d$,
  OC$_{1-3}$ alkyl, which is optionally substituted with one to four substituents independently selected from the group consisting of hydroxyl, halo, cyano, heterocyclyl, OC$_{1-3}$ alkyl, NR$^c$R$^d$, aryl and heteroaryl,
  C$_{3-8}$ cycloalkyl, which optionally substituted with one to four substituents independently selected from the group consisting of hydroxyl, halo, cyano, heterocyclyl, OC$_{1-3}$ alkyl and NR$^c$R$^d$,
  aryl, which is optionally substituted with one to four substituents independently selected from the group consisting of hydroxyl, halo, cyano, heterocyclyl, OC$_{1-3}$ alkyl, S(O)$_m$NR$^c$R$^d$, C(O)NR$^c$R$^d$ and NR$^c$R$^d$,
  heteroaryl, which is optionally substituted with one to four substituents independently selected from the group consisting of hydroxyl, halo, cyano, heterocyclyl, OC$_{1-3}$ alkyl, S(O)$_m$NR$^c$R$^d$, C(O)NR$^c$R$^d$ and NR$^c$R$^d$,
  heterocyclyl, which is optionally substituted with one to four substituents independently selected from the group consisting of hydroxyl, halo, cyano, OC$_{1-3}$ alkyl and NR$^c$R$^d$, and
  C$_{4-8}$ cycloalken, which is optionally substituted with one to four substituents independently selected from the group consisting of hydroxyl, halo, cyano, heterocyclyl, OC$_{1-3}$ alkyl and NR$^c$R$^d$,
j) S(O)$_m$R$^5$,
k) S(O)$_m$R$^7$,
l) (C=O)R$^7$,
m) (C=O)R$^5$,
n) (C=O)OR$^5$,
o) NR$^c$R$^d$ and p) 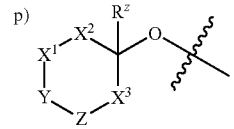

X$^1$, X$^2$ and X$^3$ are each independently selected from the group consisting of a bond or CR$^e$R$^f$;
Y is O, CR$^a$R$^b$ or NR$^c$;
Z is O, CR$^a$R$^b$ or NR$^c$;
R$^z$ is selected from the group consisting of hydrogen and C$_{1-3}$ alkyl, which is optionally substituted with one to three substituents independently selected from the group consisting of halo, hydroxyl, cyano, NH($C_{1-3}$ alkyl), N($C_{1-3}$ alkyl)$_2$, O$C_{1-6}$ alkyl and $C_{3-8}$ cycloalkyl;

A is CH or N;

$R^2$ is selected from the group consisting of hydrogen and $C_{1-6}$ alkyl, which is optionally substituted with one to three substituents independently selected from the group consisting of:
a) halo,
b) cyano,
c) $R^5$,
d) $R^7$,
e) O$R^5$ and
f) N$R^cR^d$;

$R^3$ is selected from the group consisting of:
a) hydrogen,
b) $C_{1-6}$ alkyl, which is optionally substituted with one to three substituents independently selected from the group consisting of halo, cyano, O$R^5$ and N$R^cR^d$,
c) $C_{3-8}$ cycloalkyl, which is optionally substituted with one to three substituents independently selected from the group consisting of halo, cyano, O$R^5$ and N$R^cR^d$,
d) heterocyclyl, which is optionally substituted with one to three substituents independently selected from the group consisting of halo, cyano, oxo, $R^5$, O$R^5$ and N$R^cR^d$,
e) heteroaryl, which is optionally substituted with one to three substituents independently selected from the group consisting of halo, cyano, oxo, $R^5$, O$R^5$ and N$R^cR^d$;
f) $C_{4-8}$ cycloalkenyl, which is optionally substituted with one to three substituents independently selected from the group consisting of halo, cyano, O$R^5$ and N$R^cR^d$,
g) (C=O)$R^7$,
h) (C=O)$R^5$,
i) S(O)$_m$$R^5$ and
j) S(O)$_m$$R^7$;

or $R^2$ and $R^3$ can be taken together with the atoms to which they are attached to form a 3 to 8 membered heterocyclic or heteroaryl ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
a) halo,
b) oxo,
c) cyano,
d) O$R^5$,
e) N$R^cR^d$,
f) SO$_3$H,
g) S(O)$_m$$R^5$,
h) S(O)$_m$$R^7$
i) $R^5$,
j) $R^6$,
k) $R^7$,
l) (C=O)$R^5$,
m) (C=O)O$R^5$,
n) (C=O)$R^7$ and
o) (C=O)N$R^cR^d$;

$R^5$ is selected from the group consisting of hydrogen and $C_{1-6}$ alkyl, which is optionally substituted with one to three substituents independently selected from the group consisting of:
a) halo,
b) hydroxyl,
c) O$C_{1-6}$ alkyl,
d) N$R^cR^d$,
e) (C=O)N$R^cR^d$,
f) S(O)$_m$$R^8$,
g) S(O)$_m$$R^7$,
h) $R^7$ and
i) O$R^7$;

$R^6$ is $C_{1-6}$ alkyl, which is optionally substituted with one to three substituents independently selected from the group consisting of halo and hydroxyl;

or $R^5$ and $R^6$ can be taken together with the atoms to which they are attached to form a 4 to 8 membered heterocyclic, 3 to 8 membered carbocyclic, aryl or heteroaryl ring, wherein said heterocyclic and heteroaryl rings may contain from one to three heteroatoms selected from N, O and S, wherein said heterocyclic, carbocyclic, aryl and heteroaryl rings are optionally substituted with one to three substituents independently selected from the group consisting of:
a) halo,
b) oxo,
c) cyano,
d) hydroxyl,
e) $C_{1-3}$ alkyl, which is optionally substituted with one to three halo,
f) $C_{3-8}$ cycloalkyl,
g) O$C_{1-3}$ alkyl, which is optionally substituted with one to three halo, and
h) O$C_{3-8}$ cycloalkyl;

$R^7$ is selected from the group consisting of $C_{4-8}$ heterocyclyl, $C_{3-8}$ cycloalkyl, $C_{4-8}$ cycloalkenyl, aryl and heteroaryl, wherein said heterocyclyl, cycloalkyl, cycloalkenyl, aryl and heteroaryl groups are optionally substituted with one to three substituents independently selected from the group consisting of:
a) halo,
b) cyano,
c) hydroxyl,
d) oxo,
e) $C_{1-3}$ alkyl, which is optionally substituted with one to four substituents independently selected from the group consisting of hydroxyl, halo, cyano, heterocyclyl, O$C_{1-3}$ alkyl and N$R^cR^d$,
f) O$C_{1-3}$ alkyl, which is optionally substituted with one to four substituents independently selected from the group consisting of hydroxyl, halo, cyano, heterocyclyl, O$C_{1-3}$ alkyl, N$R^cR^d$, aryl and heteroaryl,
g) $C_{3-8}$ cycloalkyl, which is optionally substituted with one to four substituents independently selected from the group consisting of hydroxyl, halo, cyano, heterocyclyl, O$C_{1-3}$ alkyl and N$R^cR^d$,
h) aryl, which is optionally substituted with one to four substituents independently selected from the group consisting of hydroxyl, halo, cyano, heterocyclyl, O$C_{1-3}$ alkyl, S(O)$_m$N$R^cR^d$, C(O)N$R^cR^d$ and N$R^cR^d$,
i) heteroaryl, which is optionally substituted with one to four substituents independently selected from the group consisting of hydroxyl, halo, cyano, heterocyclyl, O$C_{1-3}$ alkyl, S(O)$_m$N$R^cR^d$, C(O)N$R^cR^d$ and N$R^cR^d$,
j) heterocyclyl, which is optionally substituted with one to four substituents independently selected from the group consisting of hydroxyl, halo, cyano, O$C_{1-3}$ alkyl and N$R^cR^d$,
k) $C_{4-8}$ cycloalkenyl, which is optionally substituted with one to four substituents independently selected from the group consisting of hydroxyl, halo, cyano, heterocyclyl, $OC_{1-3}$ alkyl and $NR^cR^d$;

$R^8$ is hydrogen or $C_{1-6}$ alkyl, which is optionally substituted with one to three substituents independently selected from the group consisting of:
a) halo,
b) cyano,
c) hydroxyl,
d) $OC_{1-3}$ alkyl, which is optionally substituted with one to four substituents independently selected from the group consisting of hydroxyl, halo and $NR^cR^d$, and
e) $C_{3-8}$ cycloalkyl;

$R^a$ is selected from the group consisting of hydrogen and $C_{1-6}$ alkyl;

$R^b$ is selected from the group consisting of hydrogen and $C_{1-6}$ alkyl;

$R^c$ is selected from the group consisting of:
a) hydrogen,
b) $C_{1-3}$ alkyl, which is optionally substituted with one to three substituents independently selected from the group consisting of halo, hydroxyl, cyano, heteroaryl, aryl, $NH(C_{1-3}$ alkyl), $N(C_{1-3}$ alkyl)$_2$, $OC_{1-6}$ alkyl and $C_{3-8}$ cycloalkyl;

$R^d$ is selected from the group consisting of:
a) hydrogen,
b) $C_{3-8}$ cycloalkyl,
c) $C_{3-6}$ heterocyclyl,
d) $C_{1-3}$ alkyl,
e) $(C=O)C_{1-3}$ alkyl,
f) aryl and
g) heteroaryl;

wherein said cycloalkyl, heterocyclyl, alkyl, aryl and heteroaryl groups are each optionally substituted with one to three substituents independently selected from the group consisting of halo, hydroxyl, cyano, $R^8$, $SO_2R^8$, $OC_{1-6}$ alkyl and $C_{3-8}$ cycloalkyl;

or $R^c$ and $R^d$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of halo, cyano, hydroxyl, $C_{1-3}$ alkyl and $OC_{1-3}$ alkyl;

$R^e$ is selected from the group consisting of hydrogen and $C_{1-3}$ alkyl;

$R^f$ is selected from the group consisting of hydrogen and $C_{1-3}$ alkyl;

m is an integer from zero to two;

or a pharmaceutically acceptable salt thereof.

2. The compound of claim 1 wherein $R^1$ is selected from the group consisting of:
$R^5$, $OR^5$, $R^7$ and

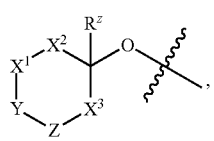

or a pharmaceutically acceptable salt thereof.

3. The compound of claim 2 wherein $R^1$ is selected from the group consisting of:
$OR^5$ and

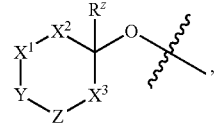

or a pharmaceutically acceptable salt thereof.

4. The compound of claim 3 wherein $R^1$ is selected from the group consisting of: $OC_{1-3}$ alkyl, $OC_{3-5}$ cycloalkyl, $OC_{4-6}$ heterocyclyl, and aryl, wherein said cycloalkyl, heterocyclyl, and aryl groups are optionally substituted with one to three substituents independently selected from the group consisting of halo, hydroxyl, $C_{1-3}$ alkyl and $OC_{1-3}$ alkyl, or a pharmaceutically acceptable salt thereof.

5. The compound of claim 4 wherein $R^2$ and $R^3$ can be taken together with the atoms to which they are attached to form a 3 to 8 membered heterocyclic or heteroaryl ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
a) halo,
b) oxo,
c) cyano,
d) $OR^5$,
e) $NR^cR^d$,
f) $SO_3H$,
g) $S(O)_mR^5$,
h) $S(O)_mR^7$
i) $R^5$,
j) $R^6$,
k) $R^7$,
l) $(C=O)R^5$,
m) $(C=O)OR^5$,
n) $(C=O)R^7$ and
o) $(C=O)NR^cR^d$;

or a pharmaceutically acceptable salt thereof.

6. The compound of claim 5 wherein $R^2$ and $R^3$ can be taken together with the atoms to which they are attached to form a 6 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
a) halo,
b) oxo,
c) $OR^5$,
d) $NR^cR^d$,
e) $S(O)_mR^5$,
f) $S(O)_mR^7$,
g) $R^5$,
h) $R^6$,
i) $R^7$,
j) $(C=O)R^5$,
k) $(C=O)OR^5$ and
l) $(C=O)R^7$, or a pharmaceutically acceptable salt thereof.

7. A compound selected from:
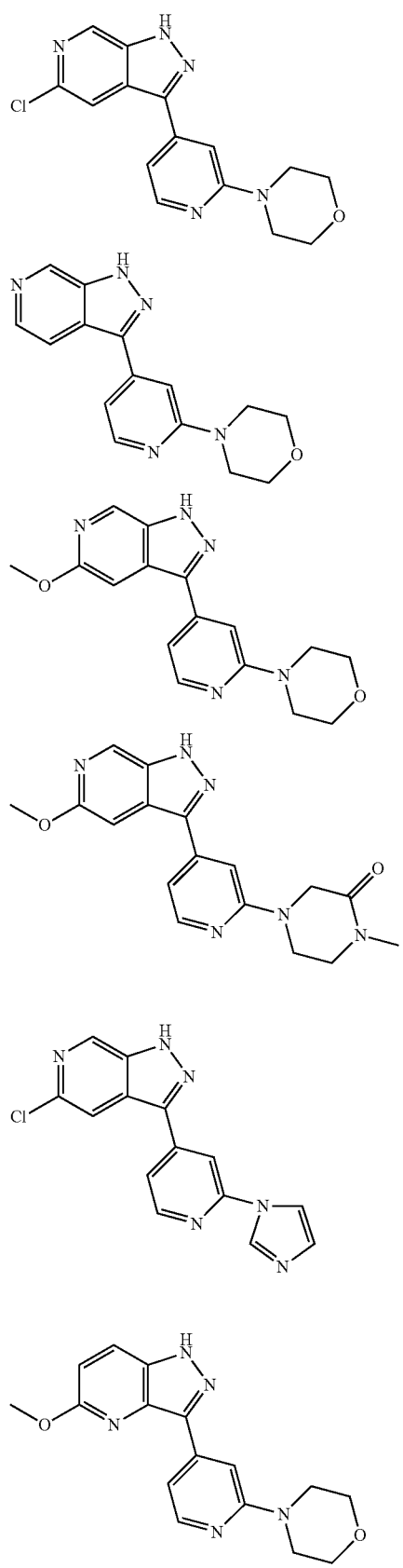
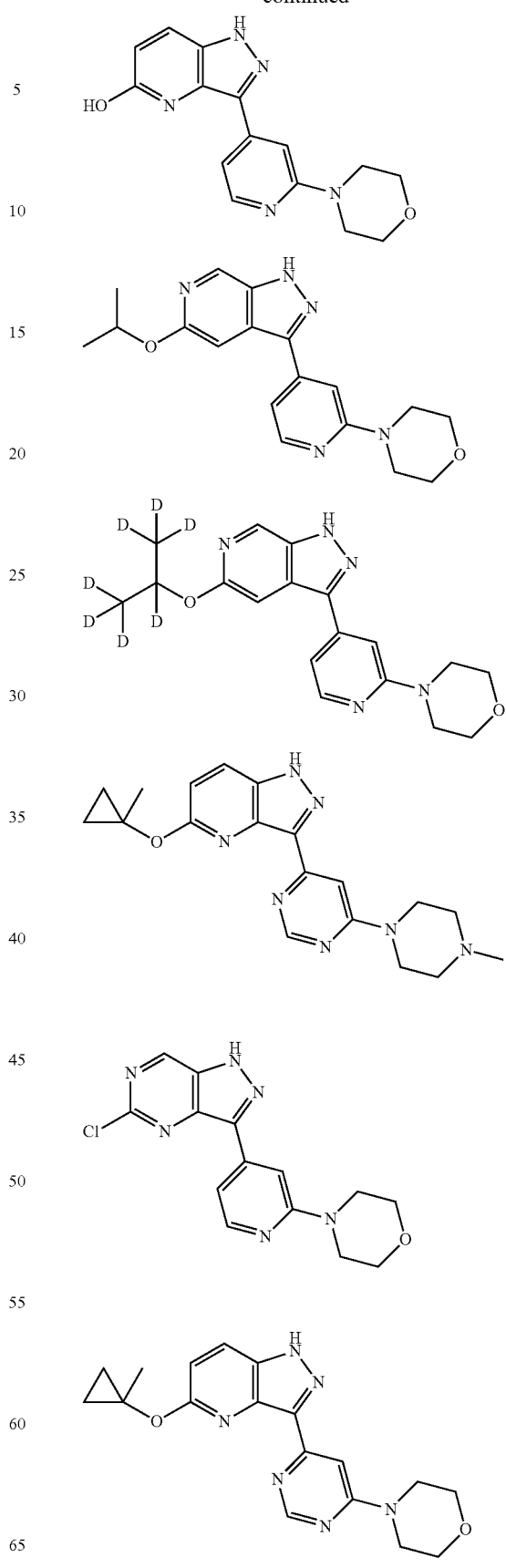

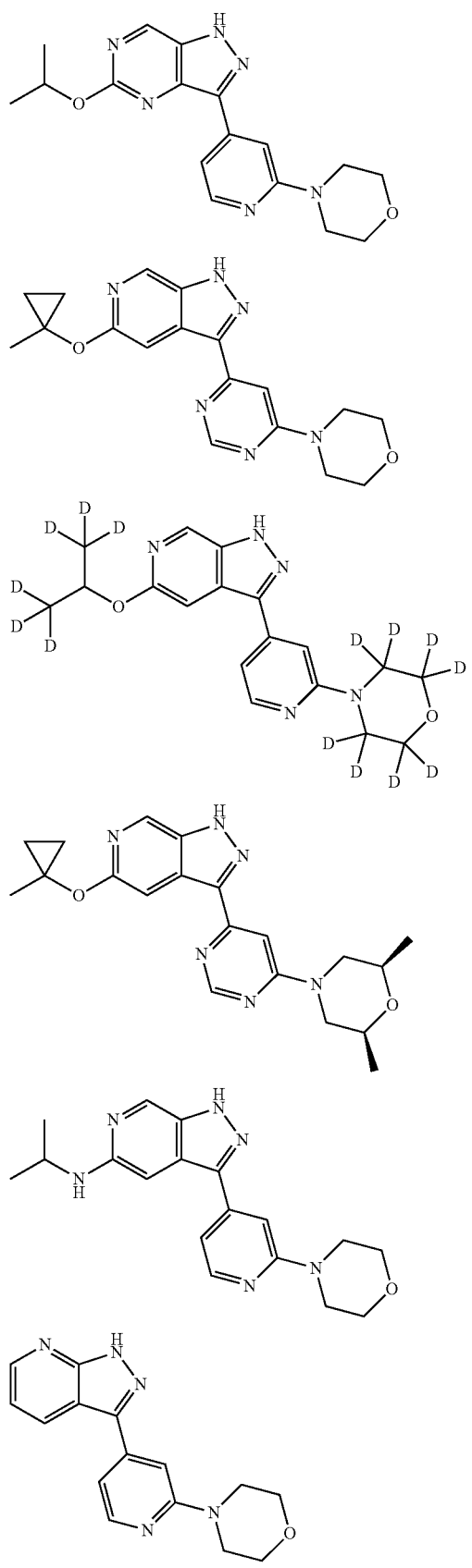
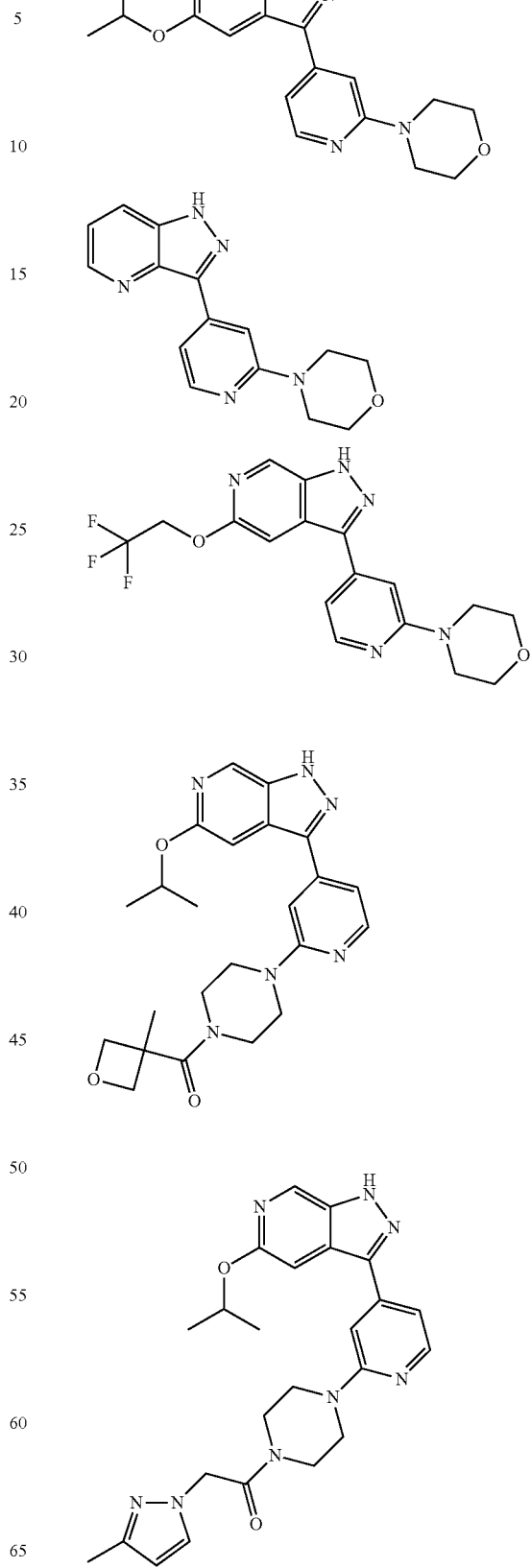

161
-continued
162
-continued
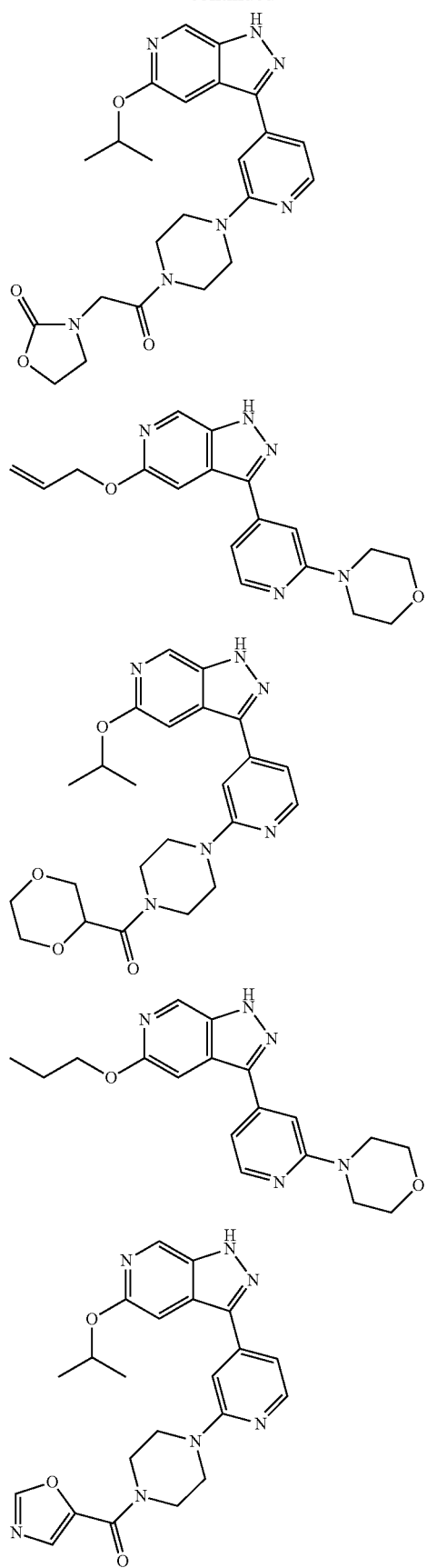
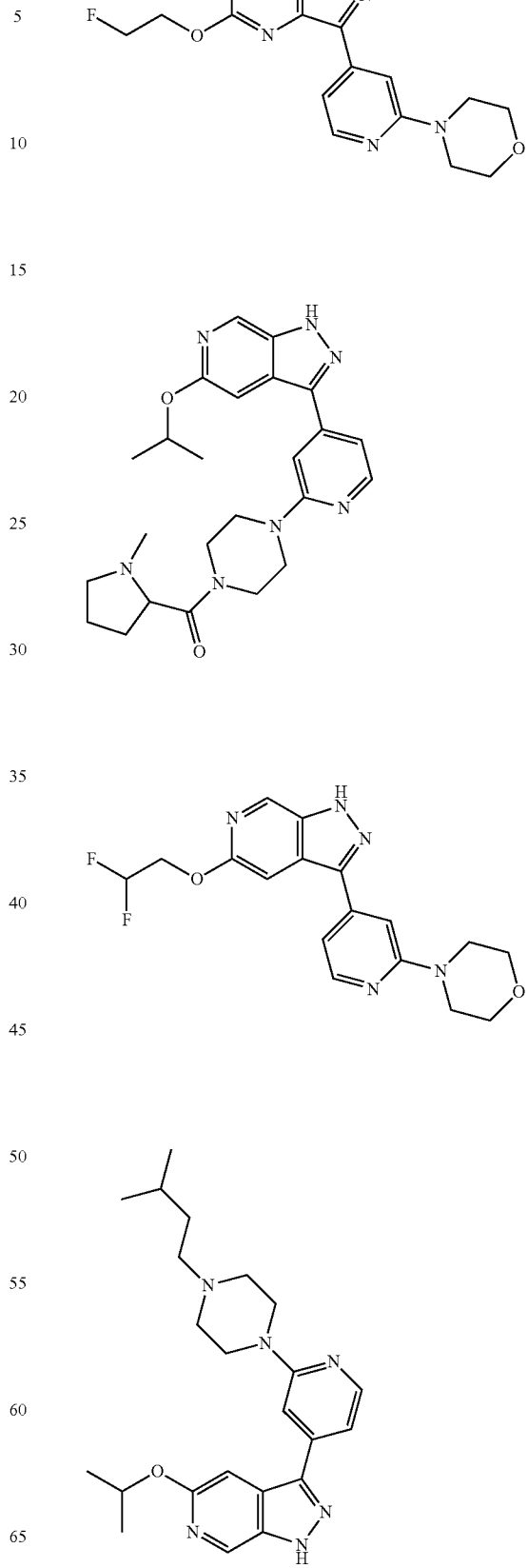

163
-continued
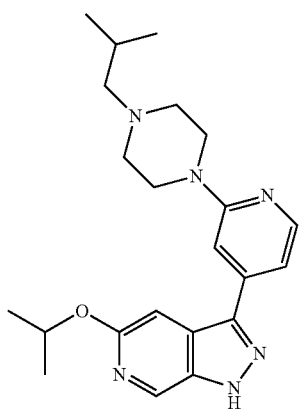
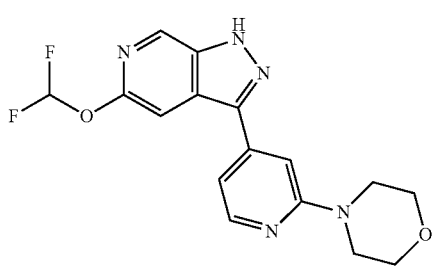
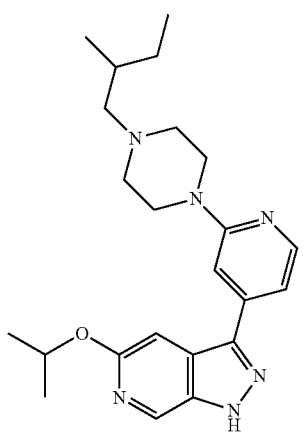
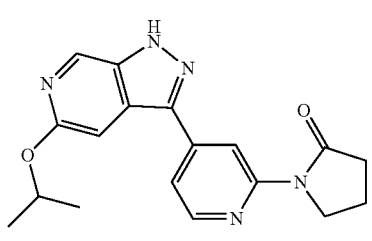
164
-continued
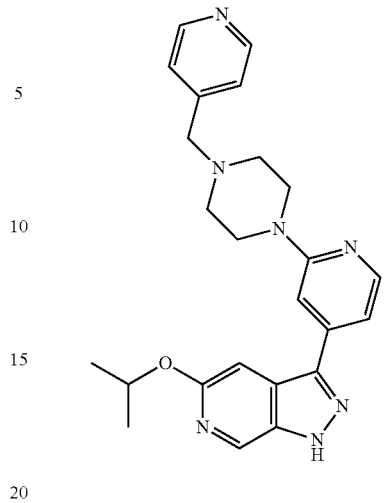
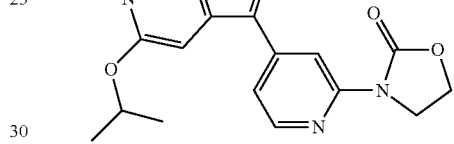
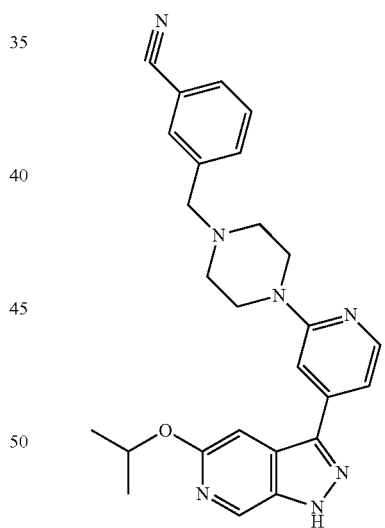
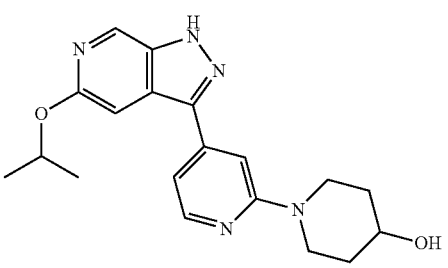

165
-continued
166
-continued
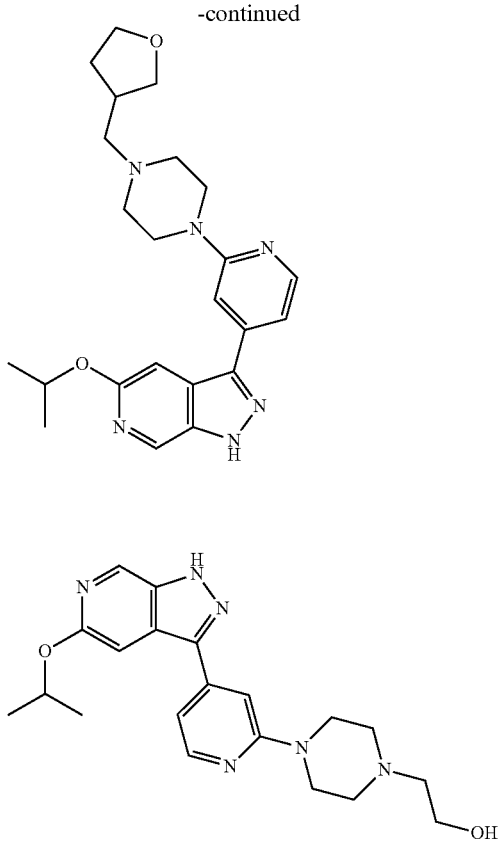
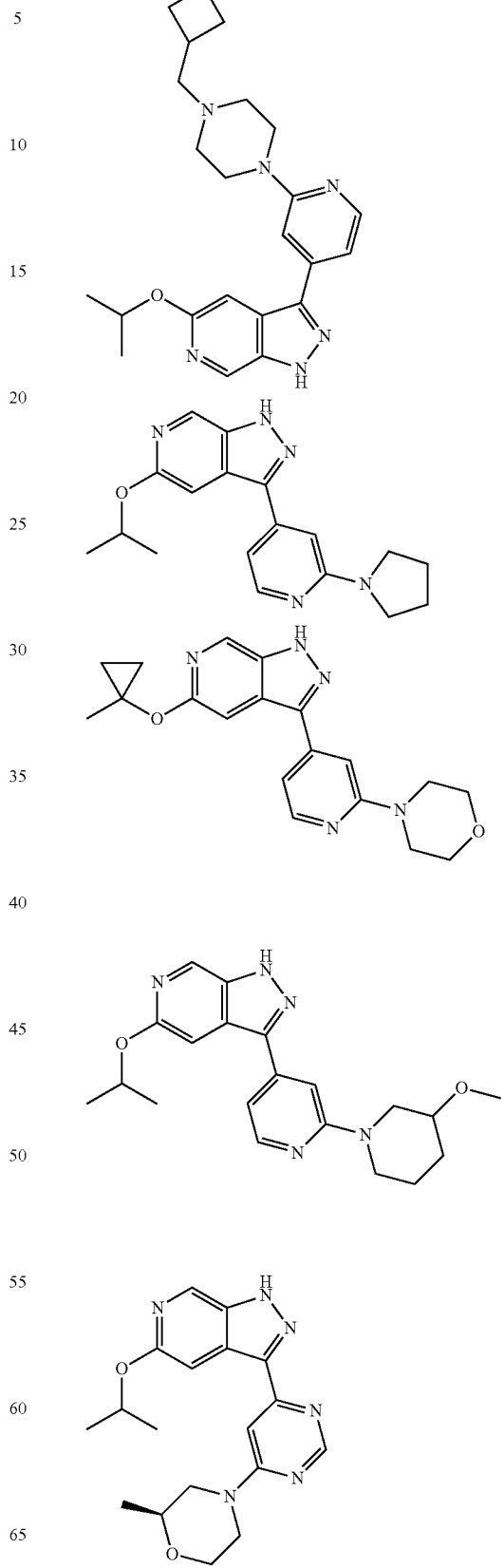

167
-continued
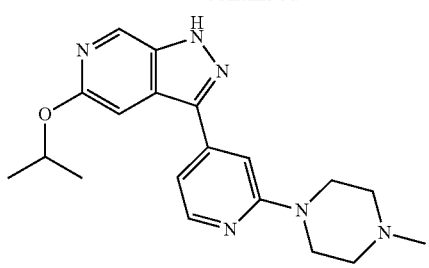
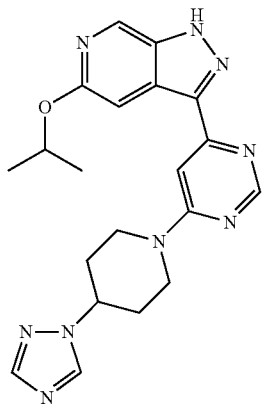
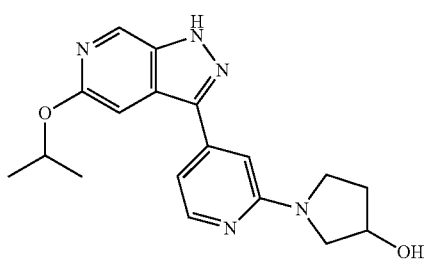
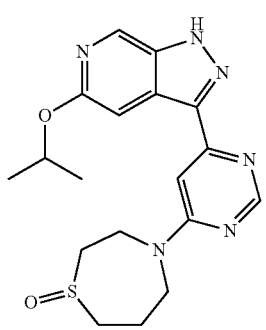
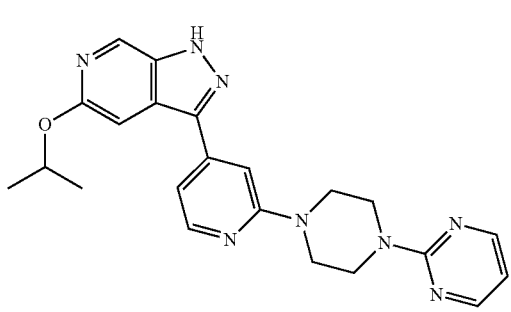
168
-continued
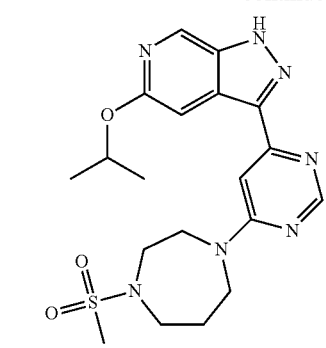
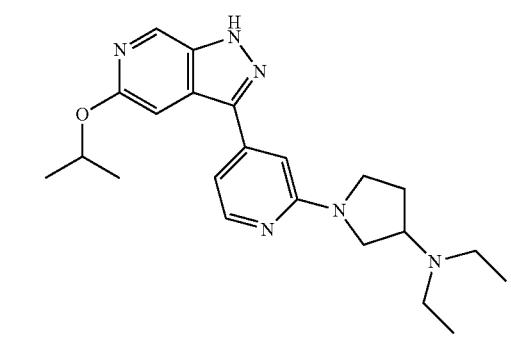
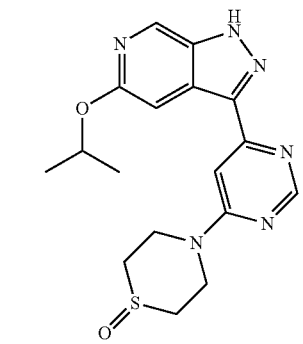
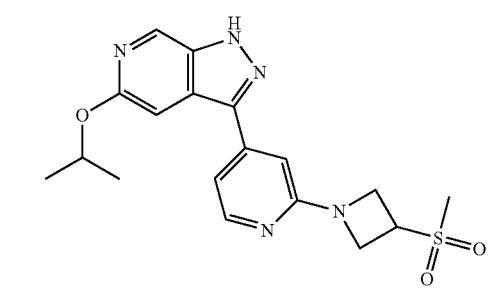
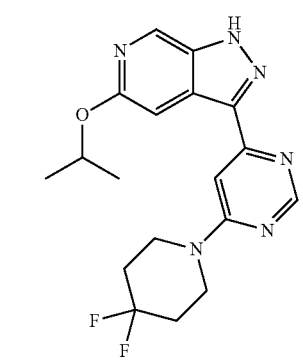

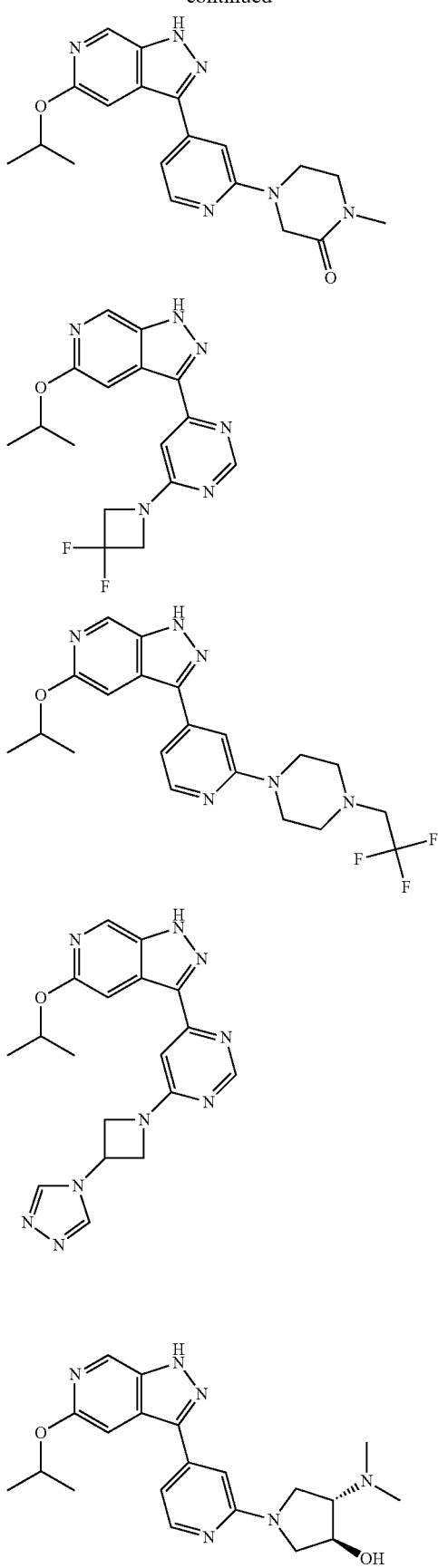

-continued
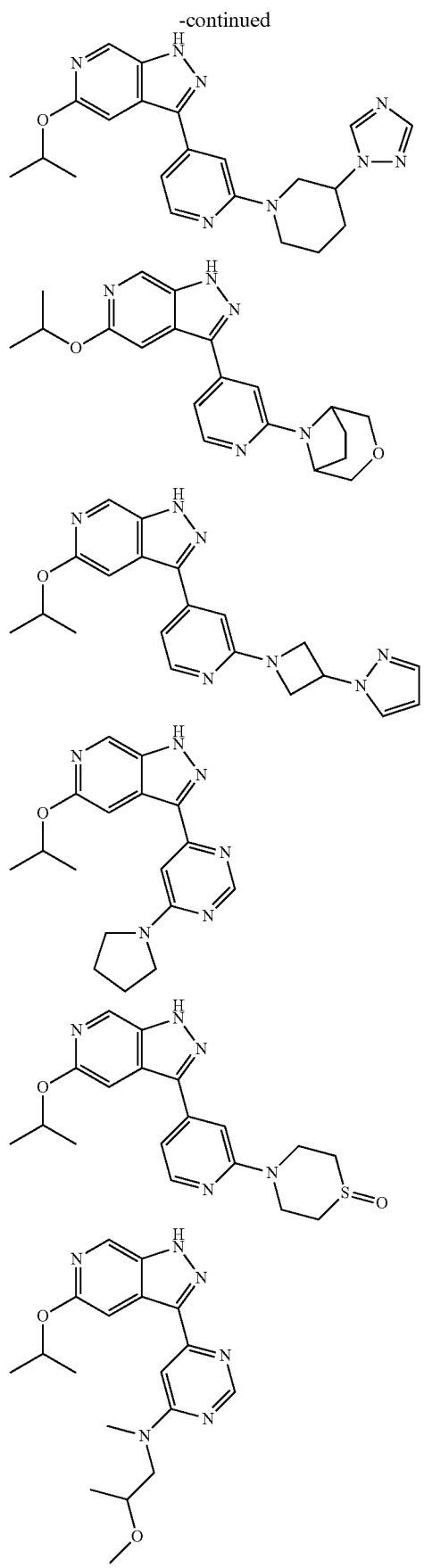
-continued
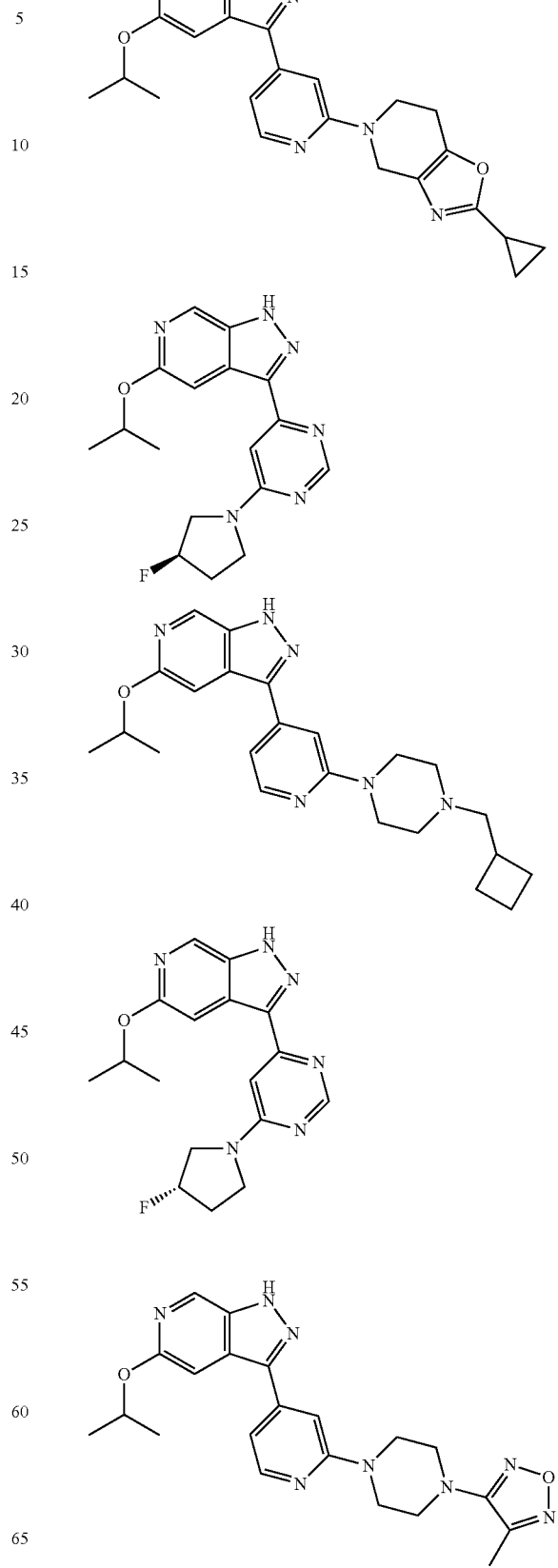

173
-continued
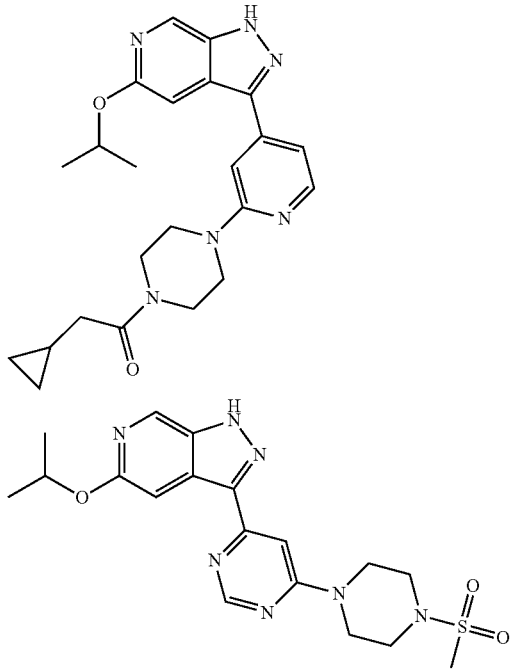
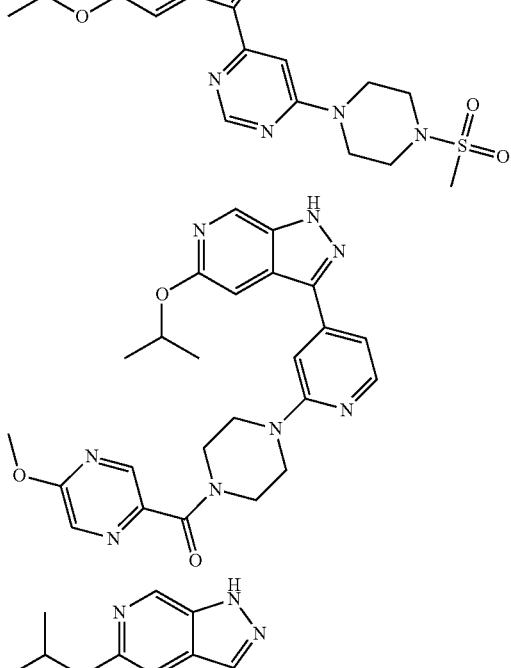
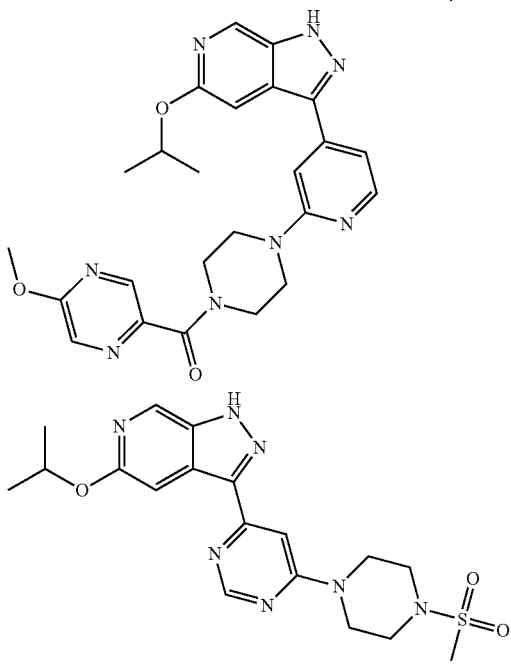
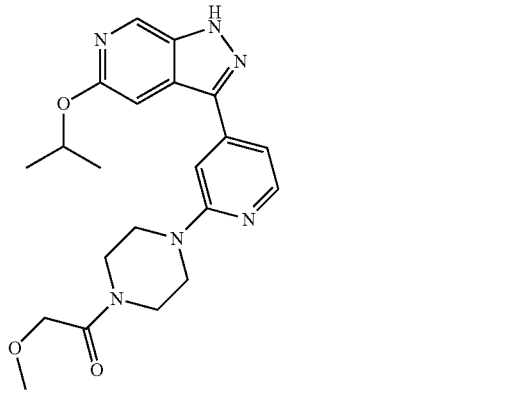
174
-continued
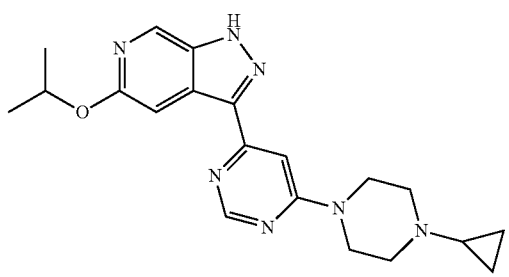
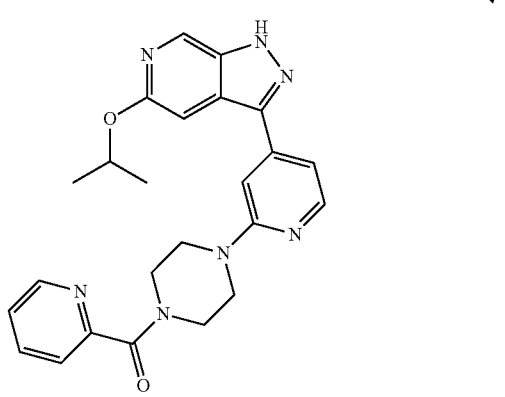
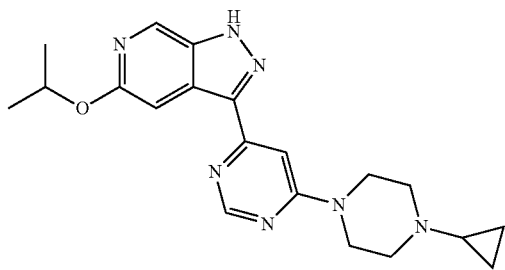
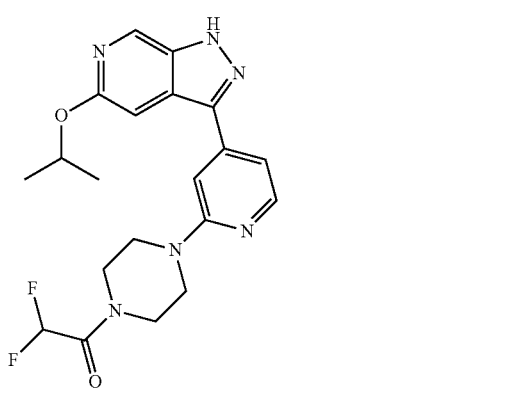
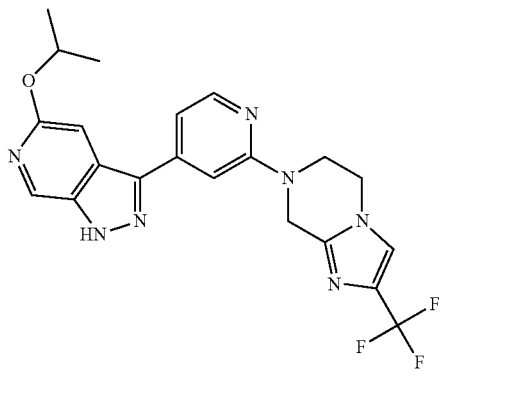

175
-continued
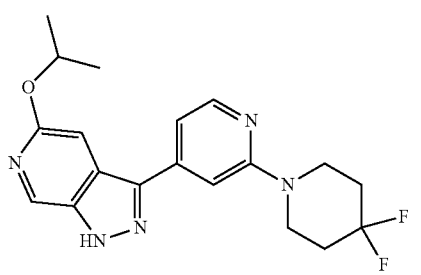
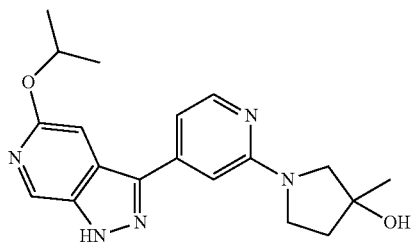
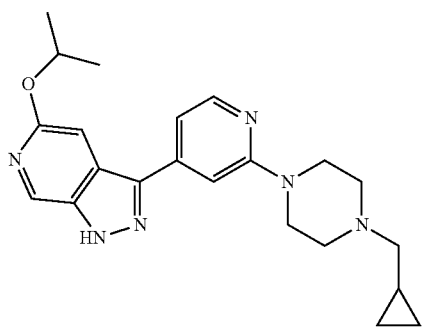
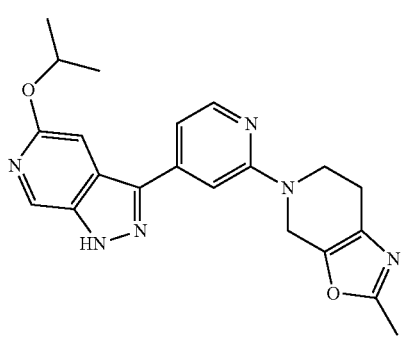
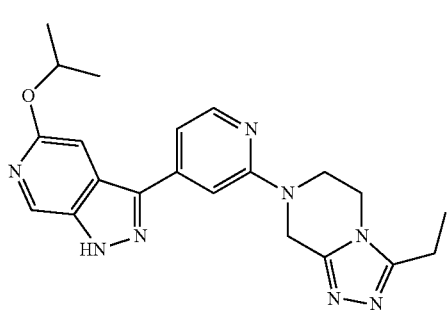
176
-continued
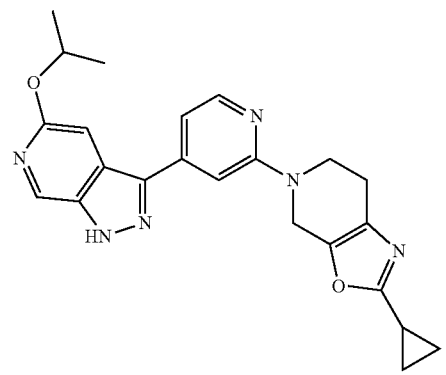
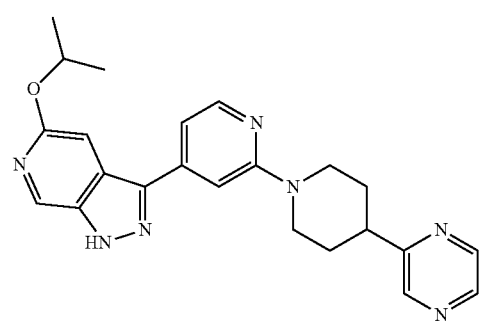
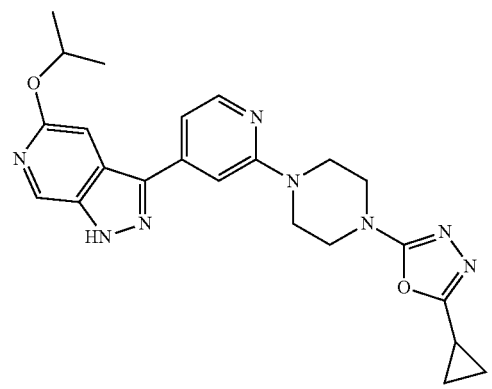
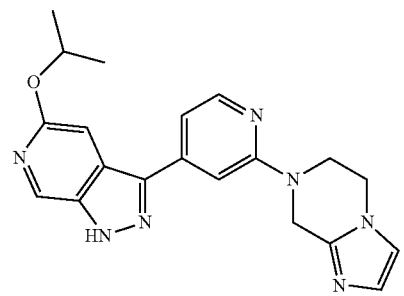
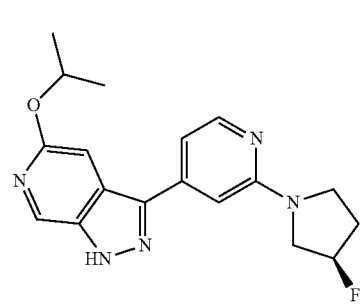

177
-continued
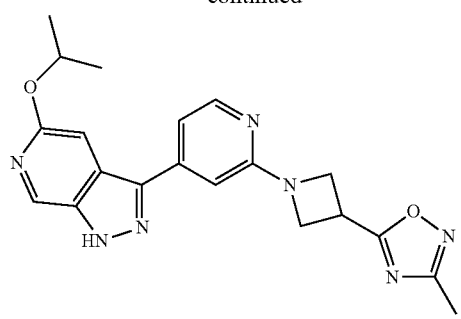
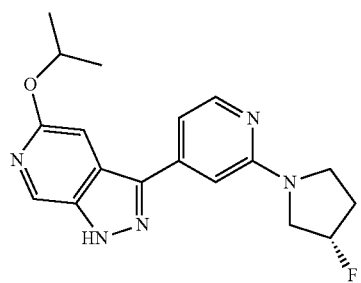
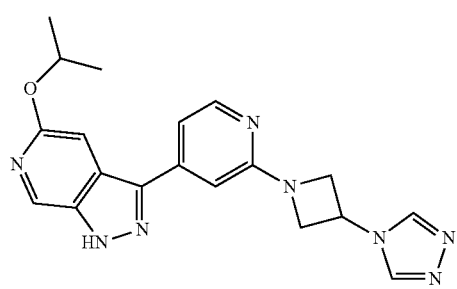
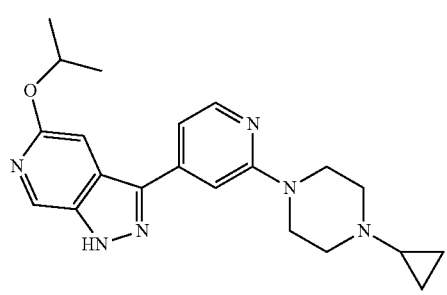
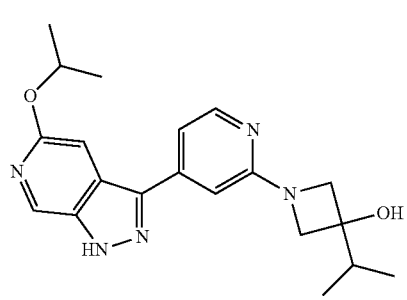
178
-continued
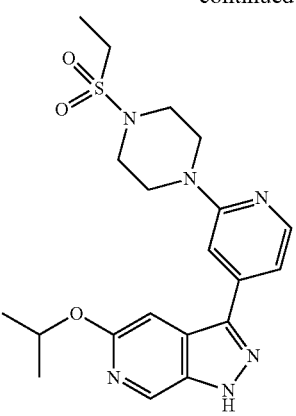
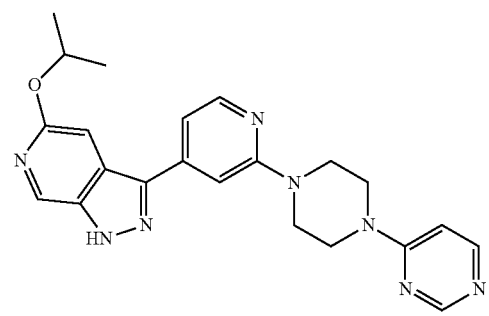
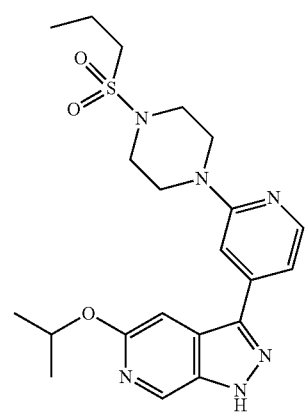
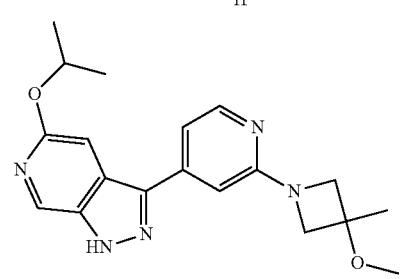
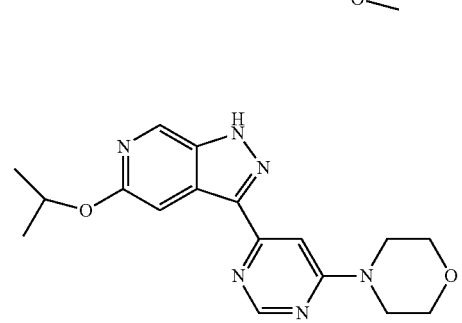

179
-continued
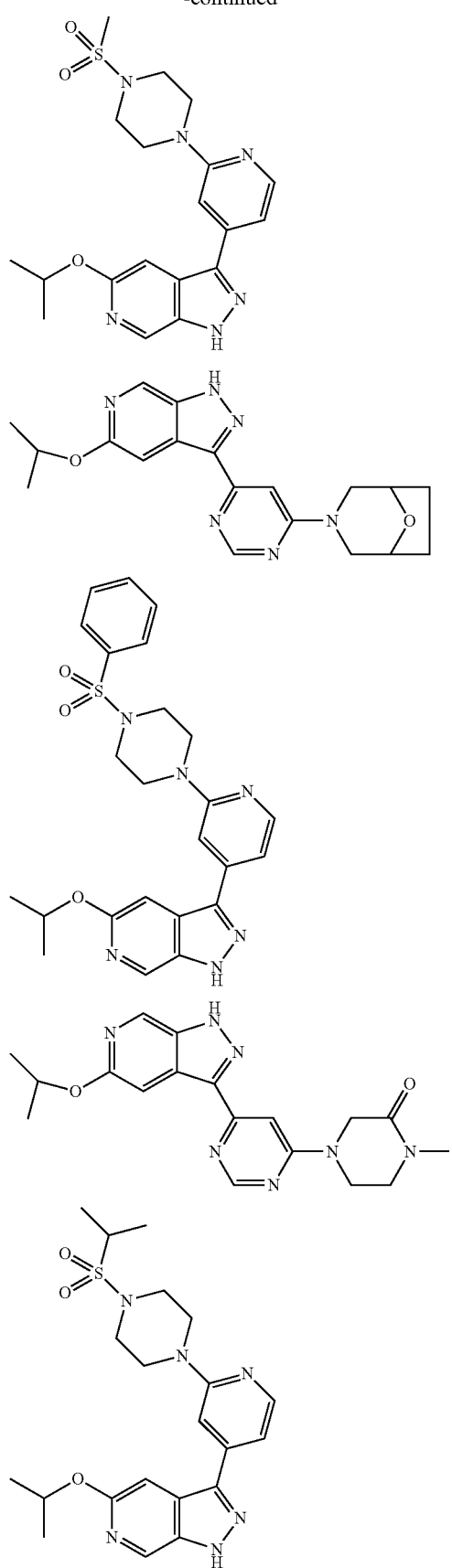
180
-continued
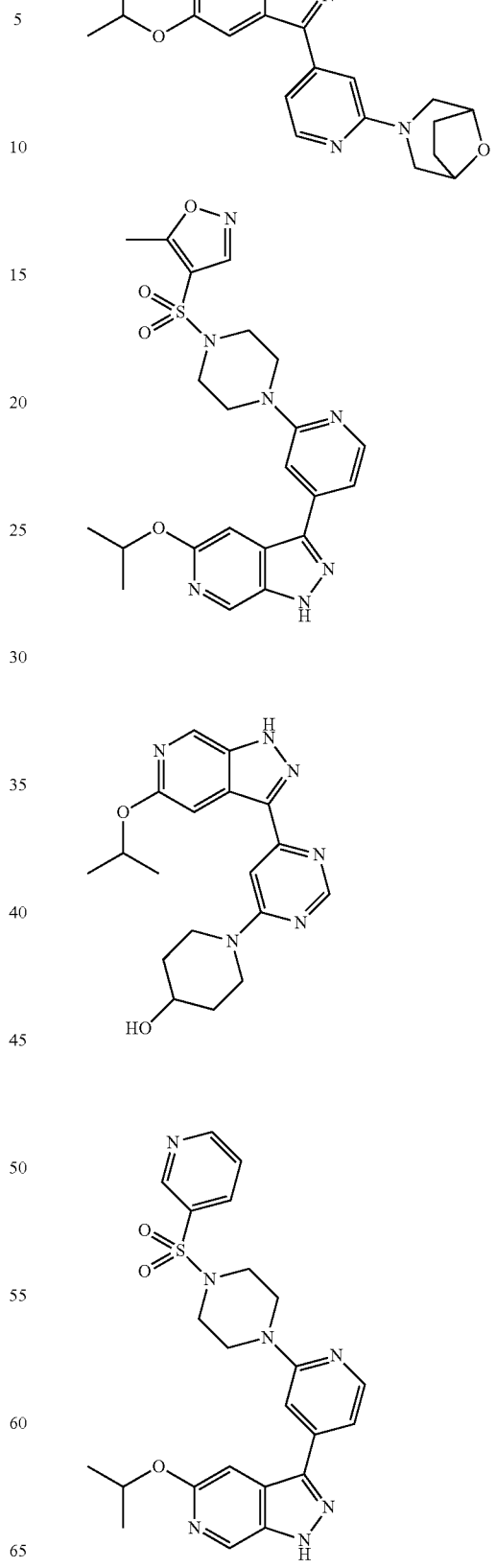

181
-continued
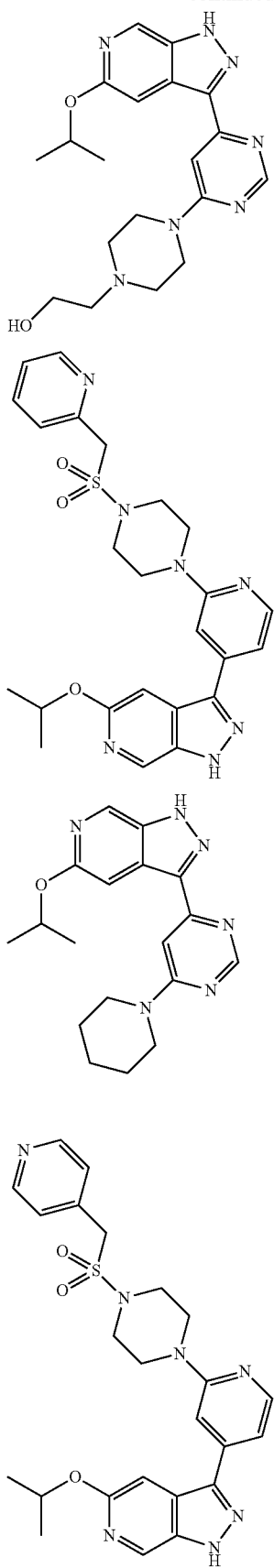
182
-continued
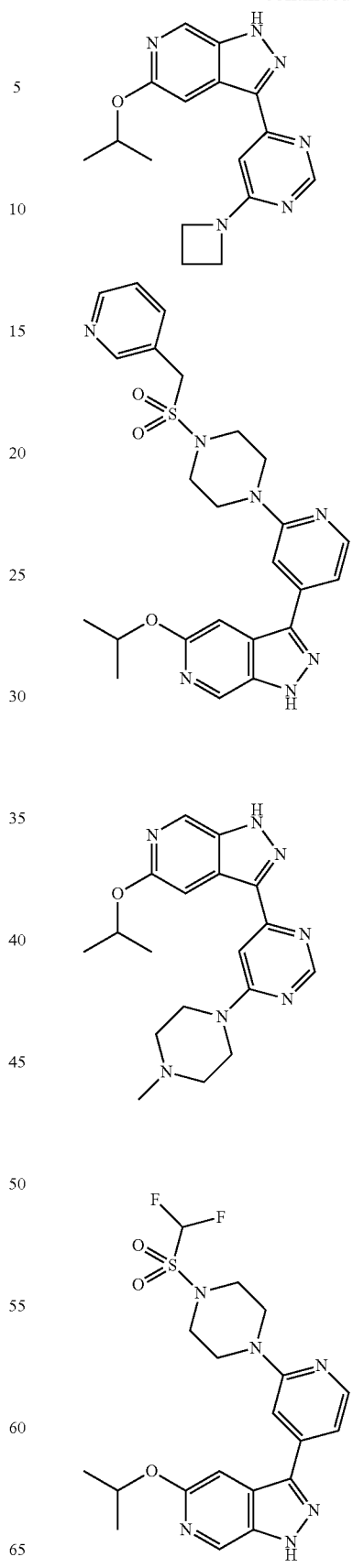

183
-continued

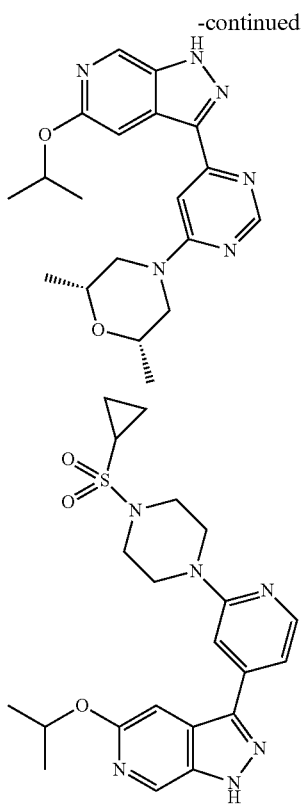

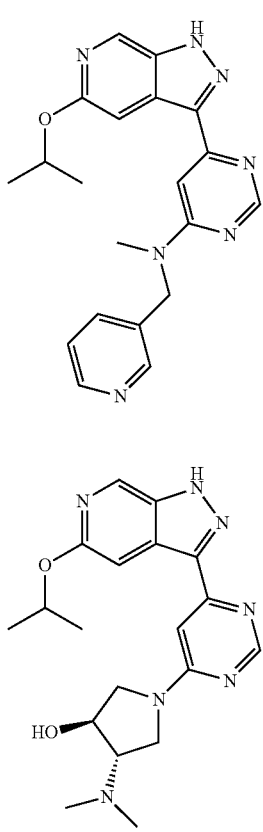

184
-continued

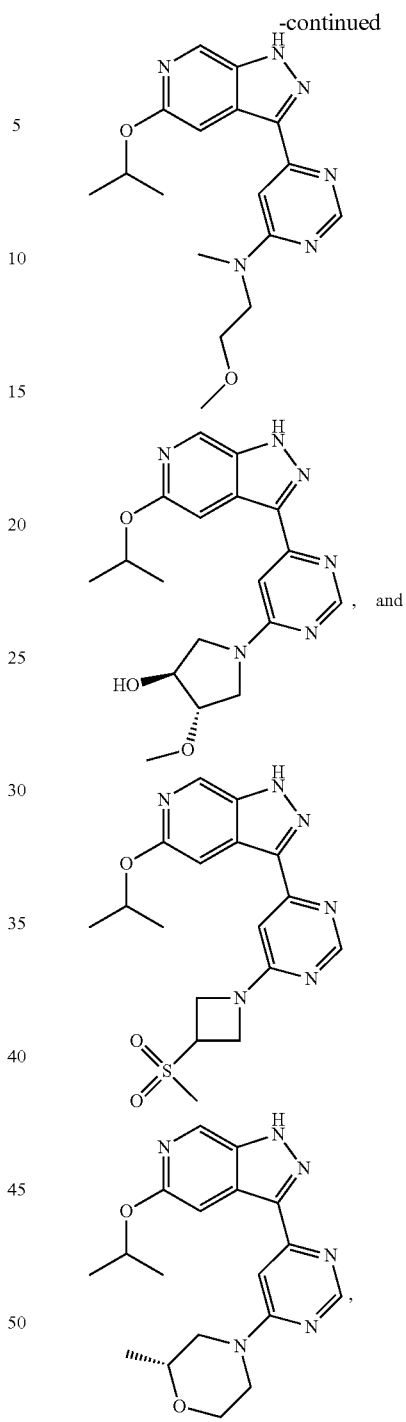

or a pharmaceutically acceptable salt thereof.

8. A pharmaceutical composition comprising a compound of claim 1, and a pharmaceutically acceptable carrier.

9. A method of treating, controlling, ameliorating, or reducing the risk of Parkinson's Disease in a patient in need thereof, comprising administering to said patient an effective amount of a compound according to claim 1, or a pharmaceutically acceptable salt thereof, optionally together with a pharmaceutically acceptable carrier.

* * * * *